(12) United States Patent
Bechtel et al.

(10) Patent No.: US 8,356,036 B2
(45) Date of Patent: *Jan. 15, 2013

(54) KNOWLEDGE DISCOVERY TOOL EXTRACTION AND INTEGRATION

(75) Inventors: Michael E. Bechtel, Plainfield, IL (US); Sanjay Mathur, Redwood City, CA (US); Jordi Arago, Barcelona (ES)

(73) Assignee: Accenture Global Services, Schaffhause (CH)

( * ) Notice: Subject to any disclaimer, the term of this patent is extended or adjusted under 35 U.S.C. 154(b) by 1117 days.

This patent is subject to a terminal disclaimer.

(21) Appl. No.: 12/070,457

(22) Filed: Feb. 19, 2008

(65) Prior Publication Data

US 2008/0147590 A1 Jun. 19, 2008

Related U.S. Application Data

(60) Division of application No. 11/127,778, filed on May 11, 2005, now abandoned, which is a continuation-in-part of application No. 11/051,733, filed on Feb. 4, 2005, now abandoned.

(51) Int. Cl.
*G06F 17/30* (2006.01)

(52) U.S. Cl. .......................................... 707/748
(58) Field of Classification Search ..................... None
See application file for complete search history.

(56) References Cited

U.S. PATENT DOCUMENTS

| | | |
|---|---|---|
| 5,265,065 A | 11/1993 | Turtle |
| 5,276,805 A | 1/1994 | Hamaguchi |
| 5,499,334 A | 3/1996 | Staab |
| 5,506,984 A | 4/1996 | Miller |
| 5,535,325 A | 7/1996 | Cattell et al. |
| 5,590,250 A | 12/1996 | Lamping et al. |
| 5,608,900 A | 3/1997 | Dockter et al. |
| 5,619,632 A | 4/1997 | Lamping et al. |
| 5,644,740 A | 7/1997 | Kiuchi et al. |
| 5,659,724 A | 8/1997 | Borgida et al. |
| 5,745,895 A | 4/1998 | Bingham et al. |
| 5,768,578 A | 6/1998 | Kirk et al. |
| 5,794,257 A | 8/1998 | Liu et al. |
| 5,801,702 A | 9/1998 | Dolan et al. |
| 5,949,968 A | 9/1999 | Gentile |
| 5,953,723 A | 9/1999 | Linoff et al. |
| 5,956,688 A | 9/1999 | Kokubo et al. |
| 5,960,430 A | 9/1999 | Haimowitz et al. |
| 5,965,688 A | 10/1999 | Davies |

(Continued)

FOREIGN PATENT DOCUMENTS

EP 0 902 380 A2 3/1999

(Continued)

OTHER PUBLICATIONS

Ponniah, Data Warehousing Fundamentals: A comprehensive Guide for IT Professionals, Sep. 11, 2001, Wiley-Interscience Publisher selected page(s).*

(Continued)

*Primary Examiner* — Neveen Abel Jalil
*Assistant Examiner* — Kevin L Young

(57) ABSTRACT

A method for integrating a data item into a knowledge model is provided. The method may include retrieving the data item from a data source, determining if the data item has been previously integrated into the knowledge model, and integrating the data element into the knowledge model if the data item has not been previously integrated.

20 Claims, 47 Drawing Sheets

U.S. PATENT DOCUMENTS

| | | | |
|---|---|---|---|
| 5,983,218 A | 11/1999 | Syeda-Mahmood | |
| 5,995,959 A | 11/1999 | Friedman et al. | |
| 5,995,961 A | 11/1999 | Levy et al. | |
| 5,999,940 A * | 12/1999 | Ranger | 1/1 |
| 6,012,055 A | 1/2000 | Campbell et al. | |
| 6,018,735 A | 1/2000 | Hunter | |
| 6,031,537 A | 2/2000 | Hugh | |
| 6,035,300 A | 3/2000 | Cason et al. | |
| 6,037,944 A | 3/2000 | Hugh | |
| 6,038,668 A | 3/2000 | Chipman et al. | |
| 6,052,693 A | 4/2000 | Smith et al. | |
| 6,073,138 A | 6/2000 | de l'Etraz et al. | |
| 6,134,559 A | 10/2000 | Brumme et al. | |
| 6,141,662 A | 10/2000 | Jeyachandran | |
| 6,166,736 A | 12/2000 | Hugh | |
| 6,166,739 A | 12/2000 | Hugh | |
| 6,233,571 B1 | 5/2001 | Egger et al. | |
| 6,236,994 B1 | 5/2001 | Swartz et al. | |
| 6,256,032 B1 | 7/2001 | Hugh | |
| 6,289,353 B1 | 9/2001 | Hazelhurst et al. | |
| 6,324,541 B1 | 11/2001 | de l'Etraz et al. | |
| 6,330,007 B1 | 12/2001 | Isreal et al. | |
| 6,356,897 B1 | 3/2002 | Gusack | |
| 6,397,231 B1 | 5/2002 | Salisbury et al. | |
| 6,418,448 B1 | 7/2002 | Sarkar | |
| 6,425,525 B1 | 7/2002 | Swaminathan et al. | |
| 6,434,556 B1 | 8/2002 | Levin et al. | |
| 6,434,558 B1 | 8/2002 | Macleod et al. | |
| 6,442,545 B1 | 8/2002 | Feldman et al. | |
| 6,446,061 B1 | 9/2002 | Doerre et al. | |
| 6,446,076 B1 | 9/2002 | Burkey et al. | |
| 6,460,034 B1 | 10/2002 | Wical | |
| 6,487,545 B1 | 11/2002 | Wical | |
| 6,499,026 B1 | 12/2002 | Rivette et al. | |
| 6,564,209 B1 | 5/2003 | Dempski et al. | |
| 6,567,814 B1 | 5/2003 | Bankier et al. | |
| 6,581,058 B1 | 6/2003 | Fayyad et al. | |
| 6,582,474 B2 | 6/2003 | LaMarca et al. | |
| 6,684,205 B1 | 1/2004 | Modha et al. | |
| 6,684,388 B1 | 1/2004 | Gupta et al. | |
| 6,721,726 B1 | 4/2004 | Swaminathan et al. | |
| 6,727,927 B1 | 4/2004 | Dempski et al. | |
| 6,826,559 B1 | 11/2004 | Ponte | |
| 6,840,442 B2 | 1/2005 | Swaminathan et al. | |
| 6,900,807 B1 | 5/2005 | Liongosari et al. | |
| 6,957,205 B1 | 10/2005 | Liongosari | |
| 6,996,774 B2 | 2/2006 | Liongosari et al. | |
| 7,000,032 B2 | 2/2006 | Kloba et al. | |
| 7,031,961 B2 | 4/2006 | Pitkow et al. | |
| 7,047,236 B2 | 5/2006 | Conroy et al. | |
| 7,099,854 B2 | 8/2006 | Liongosari | |
| 7,240,051 B2 | 7/2007 | Imaichi et al. | |
| 7,321,886 B2 | 1/2008 | Swaminathan et al. | |
| 7,350,138 B1 | 3/2008 | Swaminathan et al. | |
| 7,383,269 B2 | 6/2008 | Swaminathan et al. | |
| 7,499,046 B1 | 3/2009 | Wright et al. | |
| 7,502,770 B2 | 3/2009 | Hillis et al. | |
| 7,689,585 B2 | 3/2010 | Zeng et al. | |
| 7,904,411 B2 | 3/2011 | Bechtel et al. | |
| 2002/0007284 A1 | 1/2002 | Schurenberg et al. | |
| 2002/0046296 A1* | 4/2002 | Kloba et al. | 709/248 |
| 2002/0065856 A1 | 5/2002 | Kisiel | |
| 2002/0194201 A1* | 12/2002 | Wilbanks et al. | 707/104.1 |
| 2003/0115191 A1* | 6/2003 | Copperman et al. | 707/3 |
| 2003/0120639 A1 | 6/2003 | Potok et al. | |
| 2003/0131007 A1 | 7/2003 | Schirmer et al. | |
| 2003/0182310 A1 | 9/2003 | Charnock et al. | |
| 2003/0195877 A1 | 10/2003 | Ford et al. | |
| 2003/0212673 A1 | 11/2003 | Kadayam et al. | |
| 2004/0015486 A1 | 1/2004 | Liang et al. | |
| 2004/0030688 A1* | 2/2004 | Aridor et al. | 707/3 |
| 2004/0090472 A1 | 5/2004 | Risch et al. | |
| 2004/0122689 A1 | 6/2004 | Dailey et al. | |
| 2004/0186824 A1 | 9/2004 | Delic et al. | |
| 2004/0186842 A1 | 9/2004 | Wesemann | |
| 2004/0267729 A1 | 12/2004 | Swaminathan et al. | |
| 2005/0043940 A1 | 2/2005 | Elder | |
| 2005/0060287 A1 | 3/2005 | Hellman et al. | |
| 2005/0060643 A1 | 3/2005 | Glass et al. | |
| 2005/0065930 A1 | 3/2005 | Swaminathan et al. | |
| 2005/0108200 A1 | 5/2005 | Meik et al. | |
| 2005/0149538 A1* | 7/2005 | Singh et al. | 707/100 |
| 2006/0053151 A1 | 3/2006 | Gardner et al. | |
| 2006/0074833 A1 | 4/2006 | Gardner et al. | |
| 2006/0074836 A1 | 4/2006 | Gardner et al. | |
| 2006/0106847 A1 | 5/2006 | Eckardt et al. | |
| 2006/0179024 A1 | 8/2006 | Bechtel et al. | |
| 2006/0179025 A1 | 8/2006 | Bechtel et al. | |
| 2006/0179026 A1 | 8/2006 | Bechtel et al. | |
| 2006/0179027 A1 | 8/2006 | Bechtel et al. | |
| 2006/0179067 A1 | 8/2006 | Bechtel et al. | |
| 2006/0179069 A1 | 8/2006 | Bechtel et al. | |
| 2007/0156677 A1 | 7/2007 | Szabo | |
| 2008/0040347 A1 | 2/2008 | Potok et al. | |
| 2008/0147590 A1 | 6/2008 | Bechtel et al. | |
| 2008/0281841 A1 | 11/2008 | Swaminathan et al. | |
| 2009/0019391 A1 | 1/2009 | Bechtel et al. | |

FOREIGN PATENT DOCUMENTS

| | | |
|---|---|---|
| EP | 0 950 964 A2 | 10/1999 |
| EP | 0 902 380 A3 | 11/1999 |
| EP | 0 950 964 A3 | 11/1999 |
| EP | 1039265 A1 | 9/2000 |
| EP | 1667034 A2 | 6/2006 |
| EP | 1667034 A3 | 2/2007 |
| WO | WO 97/38376 A2 | 10/1997 |
| WO | WO 97/38376 A3 | 12/1997 |
| WO | WO 98/57277 A1 | 12/1998 |
| WO | WO 01/37120 A2 | 5/2001 |
| WO | WO 02/21259 A1 | 3/2002 |
| WO | WO 02/071273 A2 | 9/2002 |
| WO | WO 03/069506 A3 | 8/2003 |
| WO | WO 02/071273 A3 | 11/2003 |
| WO | WO 03/069506 A2 | 6/2004 |

OTHER PUBLICATIONS

U.S. Appl. No. 09/521,235, filed Mar. 8, 2000, Swaminathan.

Angeles et al., "Detection and Resolution of Data Inconsistencies, and Data Quality Criteria," Quatic Proceeeings 2004, pp. 1-7, XP002392215.

Alani, H., "TGVizTab: An Ontology Visualisation Extension for Protoègè," Proceedings of Knowledge Capture, Workshop on Visualization Information in Knowledge Engineering, Sanibel Island, FL, 2003, pp. 1-6; XP002392603.

Andrews, Keith, Ph.D., "Techniques from the field of Information Visualisation and their Potential Application to the AURIS Project," *Information Visualisation for AURIS*, Aug. 16, 2000, pp. i, ii and 1-19; © Keith Andrews.

Feldman, R., Aumann, Y., Finkelstein-Landau, M., Hurvitz, E., Regev, Y., and Yaroshevich, A., "A Comparative Study of Information Extraction Strategies," 2002, pp. 1-12; XP-002378981.

Fluit et al., "Spectacle", *Towards the Semantic Web: Ontology-driven Knowledge Management*, 2003, © John Wiley & Sons, Ltd., pp. 145-159; ISBN-0-470-84867-7; XP-002380464.

Green, S. J., "Building Hypertext Links by Computing Semantic Similarity" IEEE Transactions on Knowledge and Data Engineering, vol. 11, No. 5, Sep. 1999, pp. 713-730; XP-002317545.

Kellogg, R. B., Subhas, M., "Text to hypertext: Can Clustering Solve the Problem in Digital Libraries?" Proceedings of 1st ACM International Conference on Digital Libraries, Mar. 20, 1996, pp. 144-150; © 1996 ACM 0-89791-830-4/96/03; XP-002317546.

Lamping, John, Rao, R., and Pirolli, P., "A Focus+Context Technique Based on Hyperbolic Geometry for Visualizing Large Hierarchies," to *Xerox Palo Alto Research Center*, printed Mar. 7, 2002; © ACM.

Liongosari, Edy, Dempski, K.; and Swaminathan, K.S., "In Search of a New Generation of Knowledge Management Applications," in *ACM SIGGRROUP Bulletin*, pp. 1-4, (Jul. 1999).

Nguyen, Quang Vinh, and Huang, Mao Lin, "A Combined Visualization of Multiple Relational Structures in Shared Collaborative Workspaces," 2004 Proceedings of the IEEE Sixth International Symposium on Multimedia Software Engineering (ISMSE'04), Miami, FL, Dec. 13, 2004, Piscataway, NJ, IEEE, Dec. 13, 2004, pp. 388-395; © 2004 IEEE; 0-7695-227-3/04.

Rennison, Earl, "Galaxy of News: An Approach to Visualizing and Understanding Expansive News Landscapes," in *UIST '94*, pp. 3-12, Nov. 2-4, 1994; © 1994 ACM 0-89791-657-3/94/0011.

Sheth A., and Avant, D., "Semantic Visualization: Interfaces for exploring and exploiting ontology, knowledgebase, heterogeneous content and complex relationships," NASA Virtual Iron Bird Workshop Mar. 31 and Apr. 2, CA, Apr. 2004, pp. 1-9; © Authors or their employers; XP-002380429.

Sheth, A. Bertram, C., Avant, D., Hammond, B., Kochut, K., and Warke, Y., "Semantic Content Management for Enterprises and the Web," Submitted for review for IEEE Internet Computing, 2002, pp. 1-19; XP-002379806.

Sheth, A., Aleman-Meza, B., Arpinar, I.B., Halaschek, C., Ramakrishnan, C., Clemens, B., Warke, Y., Avant, D., Arpinar, F.S., Anyanwu, K. and Kochut, K., "Semantic Association Identification and Knowledge Discovery for National Security Applications," © To authors or their employers until publication, Jan. 31, 2004, pp. 1-16; to appear in Special Issue of Journal of Database Management on Database Technology for Enhancing National Security, 16(1) 33-53, Jan.-Mar. 2005; XP-002378976.

Anokhin, P. et al., "Fusionplex: Resolution of Data Inconsistencies in the Integration of Heterogeneous Information Sources," Jan. 20, 2004, pp. 1-31, XP002392285.

Gertz, M., "Managing Data Quality and Integrity in Federated Databases," 2nd Annual IPIP TC-11 WG11.5 Working Conference on Integrity and Internal Control in Information Systems, Nov. 1998, pp. 1-19, © IFIP 1996, Published by Chapman & Hall, XP002392339.

Jennings, M., "Enterprise Architecture View: Fingerprinting Data Warehouse Data," DM Review, Jan. 2003, pp. 1-4, XP002379520.

Naumann, F., "From Databases to Information Systems Information Quality Makes the Difference," Proceedings of the International Conference on Information Quality, 2001, pp. 1- 17.

Seligman, L. et al., "XML's Impact on Databases and Data Sharing," Computer, IEEE Service Center, Los Alamitos, CA, vol. 34, No. 6, Jun. 2001, . pp. 59-67, © 2001 IEEE XP001103951.

Sheth, A. et al., "Managing Semantic Content for the Web," IEEE Internet Computing, IEEE Service Center, New York, NY, Jul. 2002, pp. 80-87, © 2002 IEEE.

Thuraisingham, B. et al., "Data quality: developments and directions," Integrity, Internal Control and Security in Information Systems. Connecting Governance and Technology. IPIP TC11/WG11.5 Fourth Working Conference on Integrity and International Control in Information Systems, Kluwer Academic Publishers, Norwell, MA, USA, 2002, pp. 97-102, XP008067100.

Berendt, B., Hotho, A., Mladenic, D., van Someren, M., Spiliopoulou, M., & Stumme, G. (2004). A roadmap for Web Mining: From Web to Semantic Web. In Web Mining: From Web to Semantic Web URI = citeseer.ist.psu.edu/762860.html.

Paulraj Ponniah "Data Warehousing Fundamentals: A Comprehensive Guide for IT Professionals" 2001 © 2001 John Wiley & Sons, Inc. pp. 257-289, ISBN-0-47-41254-6.

Hammond, B., Sheth, A., Kochut, K., "Semantic Enhancement Engine: A Modular Document Enhancement Platform for Semantic Applications Over Heterogeneous Content," To appear in *Real World Semantic Web Applications*, 2002, pp. 1-22; To appear in Real World Semantic Web Applications, IOS Press, 2002; XP-002379024.

Storey, M.A., Musen, M., Silva, J., Best, C., Ernst, N., Fergerson, R., Noy, N., "Jambalaya: Interactive visualization to enhance ontology authoring and knowledge acquisition in Protègè," 2001; XP-002372638.

Sullivan, Dan, "Document Warehousing and Text Mining: Chapter 8: Loading and Transforming Documents", 2001, John Wiley & Sons; XP-002317590.

Andrews, K., "Visualising Cyberspace: Information Visualisation in the Harmony Internet Browser," pp. 97-104, Proc. of First IEEE Symposium on Information Visualization, Atlanta, GA, Oct. 1995.

Baecker, H.D., "Garbage Collection for Virtual Memory Computer Systems," pp. 981-986, Comm. of the ACM, vol. 15, No. 11, Nov. 1972 © 1972, Association for Computing Machinery, Inc.

Carr, L., Hill, G., DeRoure, D., Hall, W., Davis, H., Computer Networks and ISDN Systems 28 (1996) 1027-1036, Open Information Services;.

Date, C.J., "An Introduction to Database Systems," pp. 38-39, 48-52, 491-493, 792-797; vol. I, Fifth Ed., Addison-Wesley System Programming Series, © 1990 Addison-Wesley Publishing Co., Inc.

Delany, P., and Landow, G.P., "Hypermedia and Literary Studies," pp. 60-61, 71-72, 74-75, 99, 290-291; The MIT Press, Cambridge Mass. and London, England, 1991.

Findler, N.V., "Associative Networks: Representation and Use of Knowledge by Computers," pp. xv-xvi, 51-54, 62-63, 179-180; Academic Press, New York, 1979.

Halasz, F.G., Moran, T.P., Trigg, R.H., "NoteCards in a Nutshell," pp. 45-51, Proceedings of CHI'87, © 1987 ACM.

Hara, Y., Keller, A.M., Rathmann, P.K., Wiederhold, G., "Implementing Hypertext Database Relationships through Aggregations and Exceptions," pp. 1-4, Stanford Technical Report, 1991.

Ichimura, S. and Matsushita, Y., "Another Dimension to Hypermedia Access," pp. 63-72, Hypertext '93 Proceedings, © ACM 1993.

Kumar, H.P., Plaisant, C., Shneiderman, B., "Browsing Hierarchical Data with Multi-Level Dynamic Queries and Pruning," pp. 1-6 of 24, and 22 of 24; Int. Jour. Human-Computer Stud., 1996, 46(1); URL: ftp://ftp.cs.umd.edu/pub/hcil/Reports-Abstracts-Bibliography/3474.

N. Lavrac and I. Mozetic, "Second generation knowledge acquisition methods and their application to medicine," Deep Models for Medical Knowledge Engineering, E. Keravnou Editor, © 1992 Elsevier Science Publishers BV.

M. Lee and K. Foong, "A Knowledge Acquisition Framework for an Intelligent Decision-Support System," Proceedings of the 1994 Second Australian and New Zealand Conference on Brisbane, QLD, Australia, 29 Nov. 29-Dec. 2, 1994, pp. 432-436, XP010136758.

Mackinlay, J., "Automating the Design of Graphical Presentations of Relational Information," ACM, pp. 110-141, ACM Transactions on Graphics, vol. 5, No. 2, Apr. 1986.

Miriyala, K., Hornick, S.W., Tamassia, R., "An Incremental Approach to Aesthetic Graph Layout," Proc. 6th Int. Workshop on Computer-Aided Software Engineering, CASE '93, 1993.

Mukherjea, S., Foley, J.D., "Visualizing the World-Wide Web with the Navigational View Builder," Computer Networks & ISDN System, Special Issue on 3rd Int. Conf. on the World-Wide Web '95, Apr. 1995, Darmstadt, Germany.

Poulovassilis, A. and Levene, M., "A Nested-Graph Model for the Representation and Manipulation of Complex Objects," pp. 35-68, ACM Transactions on Information Systems, vol. 12, No. 1, Jan. 1994.

Robertson, G.G., Mackinlay, J.D., Card, S.K., "Cone Trees: Animated 3D Visualizations of Hierarchical Information," pp. 189-193, Proc. Conf. Human Factors in Computing Systems (CHI'91) © ACM 1991.

Roth, S.F., Kolojejchick, J., Mattis, J., Goldstein, J., "Interactive Graphic Design Using Automatic Presentation Knowledge," pp. 112-117 & p. 476, Proc. of CHI'94 Conf. Boston, Apr. 1994 © 1994 ACM.

Schneiderman, B., "Designing the user interface: Strategies for effective human-computer interaction," Reading, Addison Wesley, US, 1992, pp. 519-521, 526, XP-002210867.

Screenshots from Visio 4.0 for Microsoft Windows, © 1991-1995 Vision Corporation.

Swaminathan, K., "RA: A Memory Organization to Model the Evolution of Scientific Knowledge," pp. 23-30, 62-79, COINS Technical Report 90-80, Sep. 1990.

A. Voss, K. Nakata, M. Juhnke, "Concept Indexing," Group 99 Phoenix, Arizona, USA, Nov. 14-17, 1999, Copyright ACM 1999, pp. 1-10, XP002255123.

Wang, B., Hitchcock, P., Holden, T., "Linking Object Oriented Database and Hypertext to Support Software Documentation," pp. 149-156, ACM SIGDOC '92, Proc. 10th Ann. Int. Conf. on Systems Documentation, © ACM 1992.

"VisAnt User Manual"[Online] Oct. 24, 2004, pp. 1-39, XP002392602 Retrieved from the Internet: URL:http://visant.bu.edu/vmanual/Manual_main.htm.

Boukhelifa, Nadia et al.: "A Coordination Model for Exploratory Multi-View Visualization", CMV Proc. Coordinated and Multiple Views in Exploratory Visualization, pp. 76, 2003.

Guo, Diansheng et al.: "Multivariate Analysis and Geovisualization with an Integrated Geographic Knowledge Discovery Approach", Cartography and Geographic Information Science, vol. 32, No. 2, 2005, pp. 113-132.

Guo, D.,M. Gahegan, and A. MacEachren "An Integrated Environment for High-Dimensional Geographic Data Mining," Oct. 2004; The Third International Conference on Geographic Information Science, Adelphi, MD, USA, pp. 107-110.

Fabrikant, Sara Irina, et al., "The Distance—Similarity Metaphor in Network-Display Specifications", Cartography and Geographic Information Science, vol. 31, No. 4, .Copyrgt. 2004, pp. 237-252.

Sheth, Amit, et al., "Complex Relationships and knowledge Discovery Support in the InfoQuilt System", The VLDB Journal, vol. 12, .Copyrgt. 2003, pp. 2-27.

McDonald, Diane, "Web Services Technology Report", JISC TSW Report May 3-4, 2003, pp. 1-23.

Terveen, Loren, et al., "Constructing, Organizing and Visualizing Collections of Topically Related Web Resources", ACM Transactions on Computer-Human Interaction, vol. 6, No. 1, Mar. 1999, pp. 67-94.

Murata, Tsuyoshi, "Visualizing the Structure of Web Communities Based on Data Acquired from a Search Engine", IEEE Transactions on Industrial Electronics, vol. 50, No. 5, Oct. 2003, pp. 860-866.

Weiss, Ron, et al., "HyPursuit: a Hierarchical Network search Engine that exploits Content-Link Hypertext Clustering", Hypertext '96, Washington, DC, .Copyrgt. 1996, pp. 180-193.

Wang, Yitong, et al., "On Combining Link and Contents Information for Web Page Clustering", DEXA 2002, LNCS 2453, Springer-Verlag, Berlin, Germany, .Copyrgt. 2002, pp. 902-913.

Liu, Yew-Huey, et al., "Visualizing Document Classification: A Search Aid for the Digital Library", Journal of the American Society for Information Science, vol. 51, No. 3, .Copyrgt. 2000, pp. 216-227.

Morris, Steven, et al., "DIVA: A Visualization System for Exploring Document Databases for Technology Forecasting", Computers & Industrial Engineering, vol. 43, Issue 4, Sep. 2002, pp. 841-862.

Fabrikant, Sara Irina, "Visualizing Region and Scale in Information Spaces", ICC 2001, Beijing, China, Aug. 6-10, 2001, pp. 2522-2529.

Chung, Wingyan, et al., "Business Intelligence Explorer: A Knowledge Map Framework for Discovering Business Intelligence on the Web", HICSS 2003, Jan. 6-9, 2003, 10 pages.

Lang, K., et al., "XML, Metadata and Efficient Knowledge Discovery", Knowledge-Based Systems, vol. 13, Issue 5, Oct. 2000, pp. 321-331.

Chen, Hsinchun, et al., "Automatic Constructing of Networks of Concepts Characterizing Document Databases", IEEE Transactions on Systems, Man and Cybernetics, vol. 22, No. 5, Sep./Oct. 1992, pp. 885-902.

Hao, Ming, et al., "Visual Data Mining for Business Intelligence Applications", WAIM 2000, LNCS 1846, Springer-Verlag, Berlin, Germany, .Copyrgt. 2000, pp. 3-14.

Malinowski, Elzbieta, et al., "Representing Spatiality in a Conceptual Multidimensional Model", GIS '04, Washington, DC, Nov. 12-13, 2004, pp. 12-21.

Damianos, Laurie, et al., "MiTAP: A Case Study of Integrated Knowledge Discovery Tools", HICSS 2003, Jan. 6-9, 2003, 10 pages.

Bollacker, Kurt D., et al., "CiteSeer: An Autonomous Web Agent for Automatic Retrieval and Identification of Interesting Publications", Autonomous Agents 98, Minneapolis, MN, .Copyrgt. 1998, pp. 116-123.

Chen, Hsinchun, et al., "A Parallel Computing Approach to Creating Engineering Concept Spaces for Semantic Retrieval: The Illinois Digital Library Initiative Project", IEEE Transactions on Pattern Analysis and Machine Intelligence, vol. 18, No. 8, Aug. 1996, pp. 771-782.

Riva, Claudio, et al., "Combining Static and Dynamic Views for Architecture Reconstruction", CSMR '02, Budapest, Hungary, Mar. 11-13, 2002, pp. 47-55.

Bopf, Mike, et al., "An Architecture for Streamlining the Implementation of Biomedical Text/Image Databases on the Web", CBMS '04, Jun. 24-25, 2004, pp. 563-568.

Gansner, Emden R., et al., "An open graph visualization system and its applications to software engineering", Software—Practice and Experience, vol. 30, John Wiley & Sons, Ltd., .Copyrgt. 2000, pp. 1203-1233.

* cited by examiner

Fig. 22

Knowledge Discovery - Wizard

Step 3 of 12

Disease term:

pneumonia — 2414

Search     Default order

Disease

| Diseases Name |
|---|
| ☐ Peste-des-Petits-Ruminants |
| ☐ Severe Acute Respiratory Syndrome |
| ☐ Pneumonia, Progressive Interstitial, of Sheep |
| ☐ Bronchiolitis Obliterans |
| ☐ Bronchiolitis Obliterans Organizing Pneumonia |
| ☐ Lung Diseases, Interstitial |
| ☐ Pneumonia |
| ☐ Pleuropneumonia |
| ☐ Pneumonia, Aspiration |
| ☐ Pneumonia, Lipid |
| ☑ Pulmonary Eosinophilia |
| ☐ Silo Filler's Disease |
| ☐ Inappropriate ADH Syndrome |

2416

Select all     Clear all

<Back     Next>     Cancel

| Projects | |
|---|---|
| Total matches | Project name |
| 2 | Dys/Regulation of the Immune System in Autoimmunit |
| 2 | Three Periodical Therapies in Current & Non-Smoke |
| 1 | MOLECULAR MODULATION OF HSV VECTOR CNS INTERACTION |
| 1 | Adenosine in trauma and sepsis |
| 1 | MEDIATION OF IMMUNE COMPLEX INJURY |
| 1 | Estrogens, Paracrine Factors, and Endometrial Canc |

2448

| Literature | |
|---|---|
| Total matches | Literature title |
| 1 | The course of lung function in treated tropical pulmonary eosinophilia. |
| 1 | [Pulmonary eosinophilia] |
| 1 | Pulmonary eosinophilia (a clinico-pathological study of 60 cases). |
| 1 | Pulmonary eosinophilia associated with vasculitis and extra-vascular granulon |
| 1 | Spirometry in tropical pulmonary eosinophilia. |
| 1 | Tropical pulmonary eosinophilia. |

2450

Step 12 of 12

[<Back] [Show] [Cancel]

Master Filter

General Options | Journal Filter | Entity Filter | Publication Filter

☑ Only include the following phenotypes:

| Name |
|---|
| Babesiosis |
| Back Pain |
| Bacteremia |
| Bacterial Infections |
| Bacteroides Infections |

Edit List — 2614

☑ Only include the following organisms:

| Name |
|---|
| F. nucleatum |
| P236/smH4 isolate |
| faba bean |
| Faba bean phyllody phytoplasma |
| Fabrella tsuga |
| P38 group of mycoplasmas |
| Faboideae |

Edit List

Apply Filters    Cancel 2610
2612

Fig. 26C

KNOWLEDGE DISCOVERY TOOL EXTRACTION AND INTEGRATION

RELATED APPLICATIONS

The present patent document is a divisional of U.S. patent application Ser. No. 11/127,778, filed May 11, 2005, now abandoned which is a continuation-in-part of U.S. patent application Ser. No. 11/051,733 filed Feb. 4, 2005, now abandoned both of which are hereby incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © 2004, Accenture, All Rights Reserved.

BACKGROUND

1. Technical Field

The present invention relates generally to an improved method for obtaining, managing, and providing complex, detailed information stored in electronic form in a plurality of sources. The invention may find particular use in organizations that have a need to discover relationships among various pieces of information in a given field.

2. Background Information

With the advent of the Internet, the Information Age is upon us. Today, one can find vast amounts of information about any given field or topic at the touch of a button. This information may be available from myriad sources in a variety of commonly recognized formats, such as XML, flat-files, HTML, text, spreadsheets, presentations, diagrams, programming code, databases, etc. This information may also be kept in third-party proprietary formats.

Amid this apparent wealth of online information, people still have problems finding the information they need. Online information retrieval may have problems including those related to inappropriate user interface designs and to poor or inappropriate organization and structure of the information. Additionally, the storage of information online in the variety of formats described above also leads to retrieval problems.

The existence of a variety of information sources leads to many problems. First, there is a lack of a unified information space. An "information space" is the set of all sources of information that is available to a user at a given time or setting. When information is stored in many formats and at many sources, a user is forced to spend too much overhead on discovering and remembering where different information is located (e.g., web pages, online databases, etc). The user also spends a large amount of time remembering how to find information in each delivery mechanism. Thus, it is difficult for the user to remember where potentially relevant information might be, and the user is forced to jump between multiple different tools to find it.

The existence of a variety of information sources also leads to information discovery strategies that lack cohesion. Users must learn to use and remember a variety of metaphors, user interfaces, and searching techniques for each delivery mechanism and class of information. Other problems associated with large numbers of information sources include a lack of links between information sources, and poor delivery mechanisms that don't provide a global view of the information space.

To overcome these problems, knowledge discovery tools have been developed. These tools extract information from a plurality of data sources, integrate the information into a common data model, and provide a graphical user interface for viewing the information. While these types of systems have been useful for unifying the information space for a given domain, they still suffer from several limitations.

First, each of these data sources typically includes a large volume of files. Thus, collecting and integrating information from a particular data source consumes both time and resources. However, in order to truly represent the information space for a given domain, these tools must collect data from many data sources. Each data source added to the process becomes an additional strain on both resources and time. Moreover, this information must be processed repeatedly to ensure that the data model includes the most current information. Present systems will process a data source in its entirety each and every time an extraction and integration cycle take place. Accordingly, there is a need for a system that doesn't waste time and resources re-integrating information that has already been integrated into the data model.

Second, integrating information from a plurality of data sources also leads to problems in the consistency of the information contained in the data model. Information in the data model may be overwritten by less reliable data. For example, a particular person's name may be found in both a structured database maintained by the IRS and the text of an email. In present systems, the name sourced from the email may be used to overwrite the name obtained from the IRS if the email is integrated later. Because the information maintained by the IRS is inherently more reliable than the text of an email (because of both source credibility and structured data), there is a need for a system that takes into account the reliability of the information maintained by the data sources before integrating that information into the data model.

Third, the information integrated into the data model is inherently related as that information defines the information space for a given domain. Unfortunately, present systems do not fully realize these interrelationships. Typically, relationships between the data in the knowledge must be defined manually. Manually defining these relationships, however, is a time consuming and expensive process. While systems automatically incorporate those relationships maintained by a particular data source (for example, relationships defined by a database data source), these relationships only represent a fraction of the relationships present among the information contained in the data model. Accordingly, there is a need for a system automatically discovering and generating various types of relationships.

The present invention provides a robust technique for integrating, from a plurality of data sources, only the necessary, most reliable data into a data model, and automatically discovering inter-relationships among the various elements of the data model.

BRIEF SUMMARY

In one embodiment, a method for integrating a data item into a knowledge model is provided. The method may include retrieving the data item from a data source, determining if the data item has been previously integrated into the knowledge model, and integrating the data element into the knowledge model if the data item has not been previously integrated.

In another embodiment, a method of integrating a data item into a knowledge model including data collected from a plurality of data sources is provided. The method may include retrieving a data item from one of the plurality of data sources, the data item including a first type of information, determining a reliability value for the one of the plurality of data sources for the first type of information by either leveraging an existing reliability score indicative of a source's reliability or generating an independent reliability score indicative of a source's reliability, and integrating the data item and the reliability value into the knowledge model.

These and other embodiments and aspects of the invention are described with reference to the noted Figures and the below detailed description of the preferred embodiments.

BRIEF DESCRIPTION OF THE DRAWINGS

FIG. 22 is an exemplary screen shot of a search tool in accordance with an embodiment of the present invention;

FIGS. 24A-L are exemplary screen shots of a wizard service in accordance with an embodiment of the present invention;

FIGS. 26A-E are exemplary screen shots of a filters dialog in accordance with an embodiment of the present invention.

DETAILED DESCRIPTION OF THE DRAWINGS AND THE PRESENTLY PREFERRED EMBODIMENTS

Figure 1:
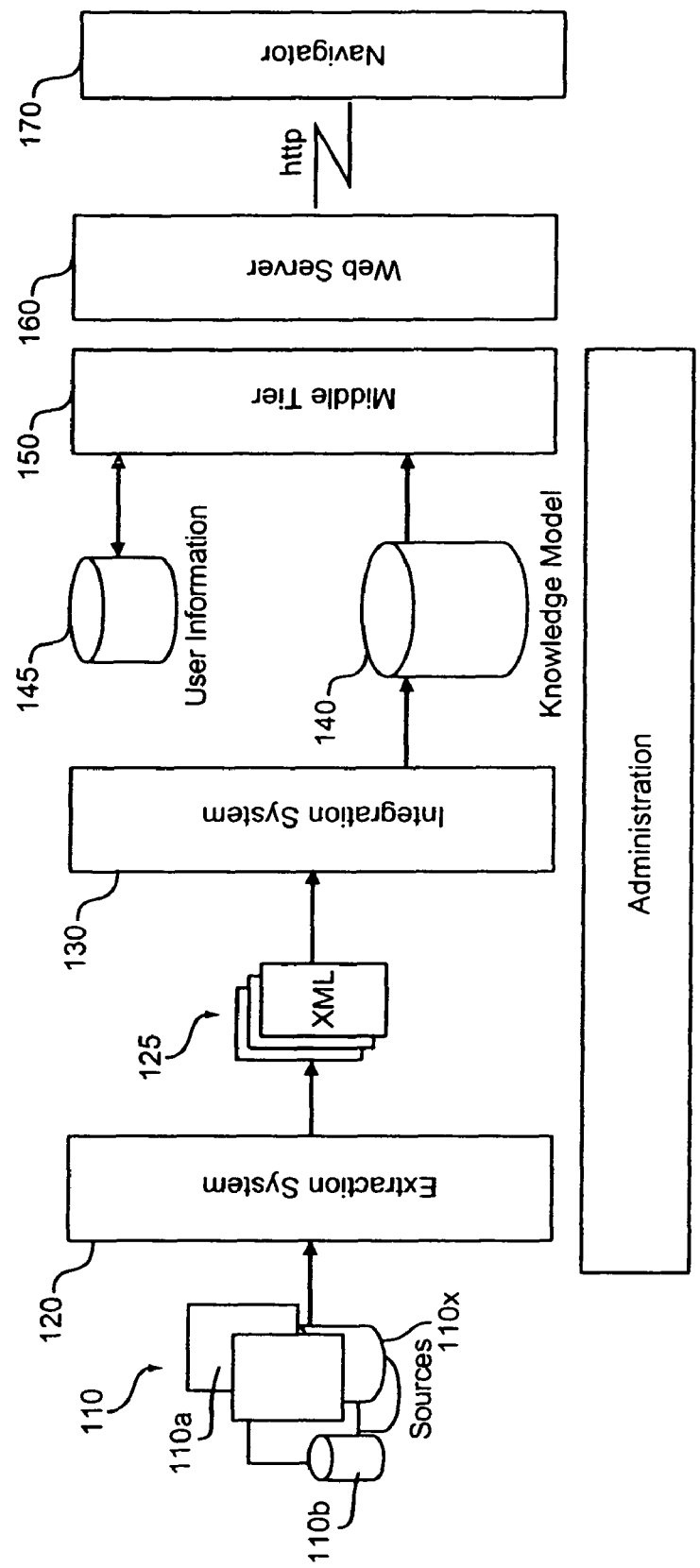
FIG. 1 is a diagram representative of an embodiment of a knowledge discovery tool in accordance with an embodiment of the present invention.

Referring now to the drawings, and particularly to FIG. 1, there is shown an embodiment of a knowledge discovery system 100 in accordance with the present invention. While the preferred embodiments disclosed herein contemplate a knowledge model based on an information space for pharmaceutical research and the information and data sources related thereto, the present invention is equally applicable for knowledge discovery for any information space defined in any type of data source. Examples of information spaces include software development, drug development, financial research, governmental data administration, and clinical trials, product development and testing etc.

The knowledge discovery system in the embodiment of FIG. 1 includes an extraction tool 120, an integration tool 130, a knowledge model 140, a user information database 145, a middle tier 150, and a web server 160. The extraction tool 120 extracts relevant information from a plurality of data sources 10a, 10b, and 110x. Optionally, the extraction tool 120 may convert the information into a common format 125, such as XML. Preferably, the extraction tool 120 is implemented using BIZTALK SERVER, provided by Microsoft Corporation of Redmond, Wash. Once relevant information is extracted, the integration tool 130 incorporates the information into the knowledge model 140. Preferably, the integration tool is implemented as a COM+ application, using the COMPONENT OBJECT MODEL software architecture provided by Microsoft Corporation of Redmond Wash. Finally, the middle tier 150 and optional web server 160 are provided to present the information contained in the knowledge model 140 via a navigator tool 170. Preferably, the middle tier is implemented using the .NET framework for Web services and component software provided by Microsoft Corporation of Redmond, Wash. Optionally, access to the knowledge model 140 via the navigator 170 may be restricted to registered users. User information may be stored in the user information database 145.

Figure 2A:
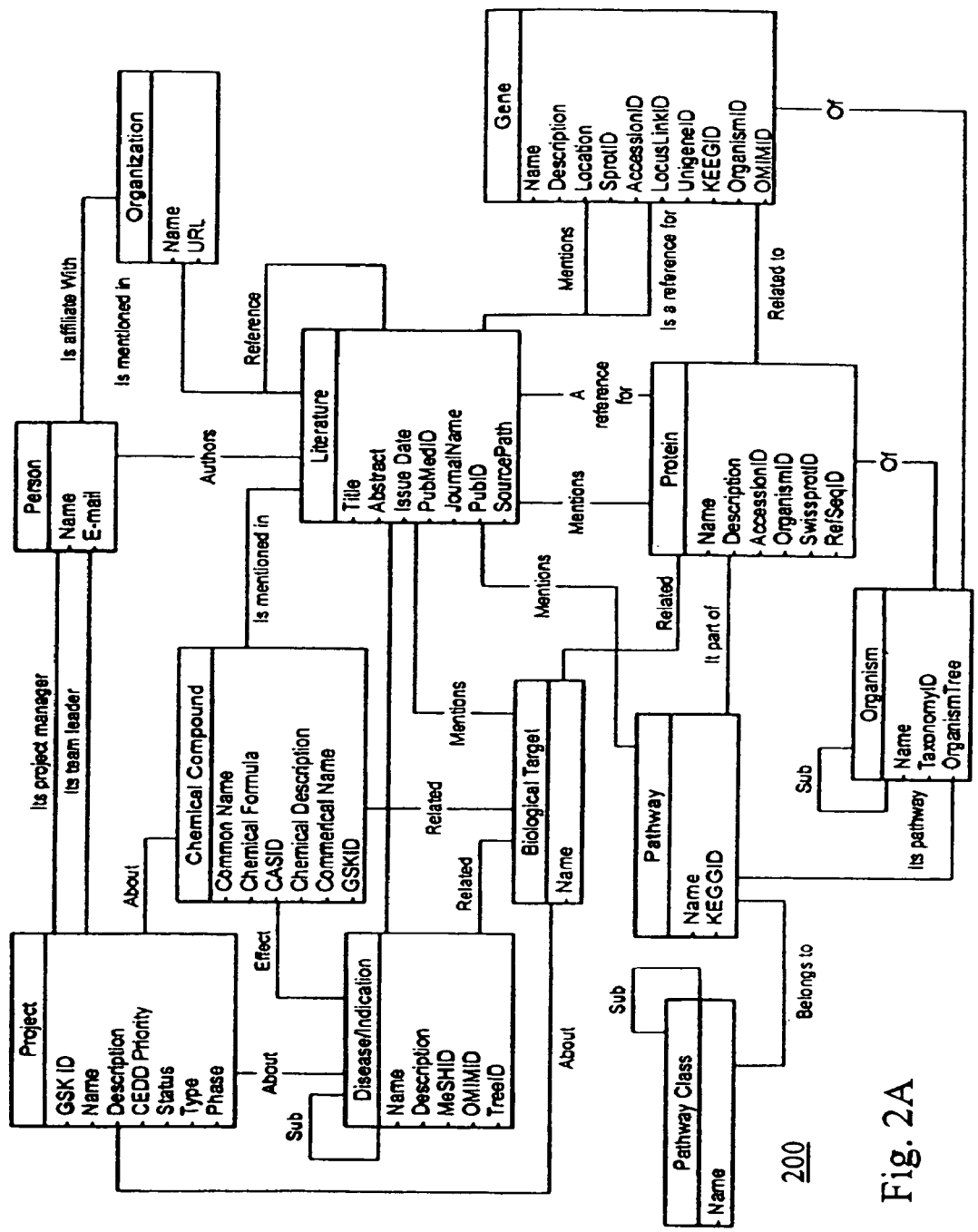
FIG. 2A is a diagram representative of tables of an exemplary knowledge model in accordance with an embodiment of the present invention.
Figure 2B:
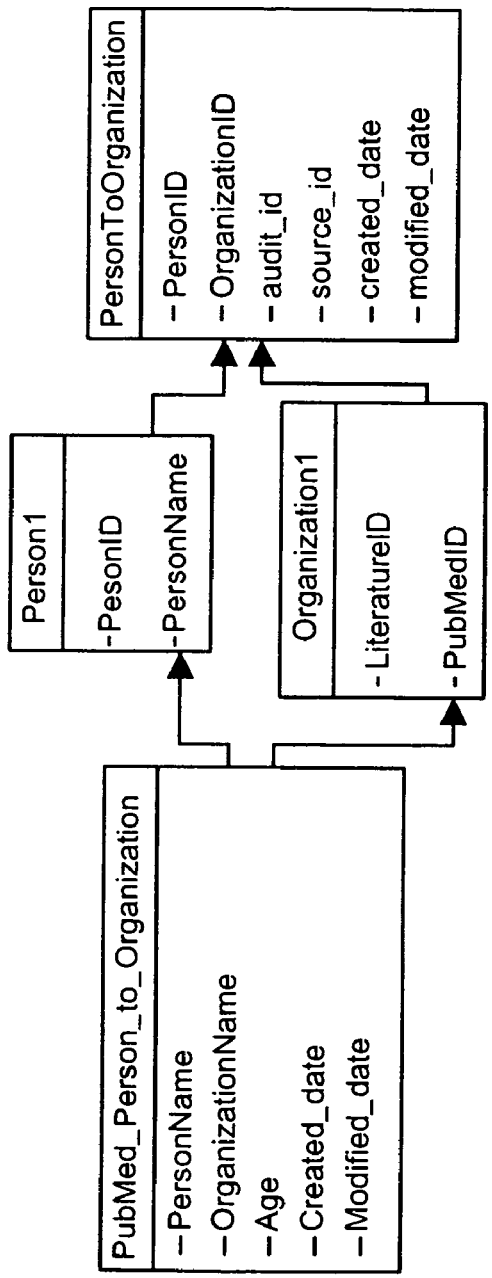
FIG. 2B is a diagram representative of a field-to-field relationship in accordance with an embodiment of the present invention.
Figure 2C:
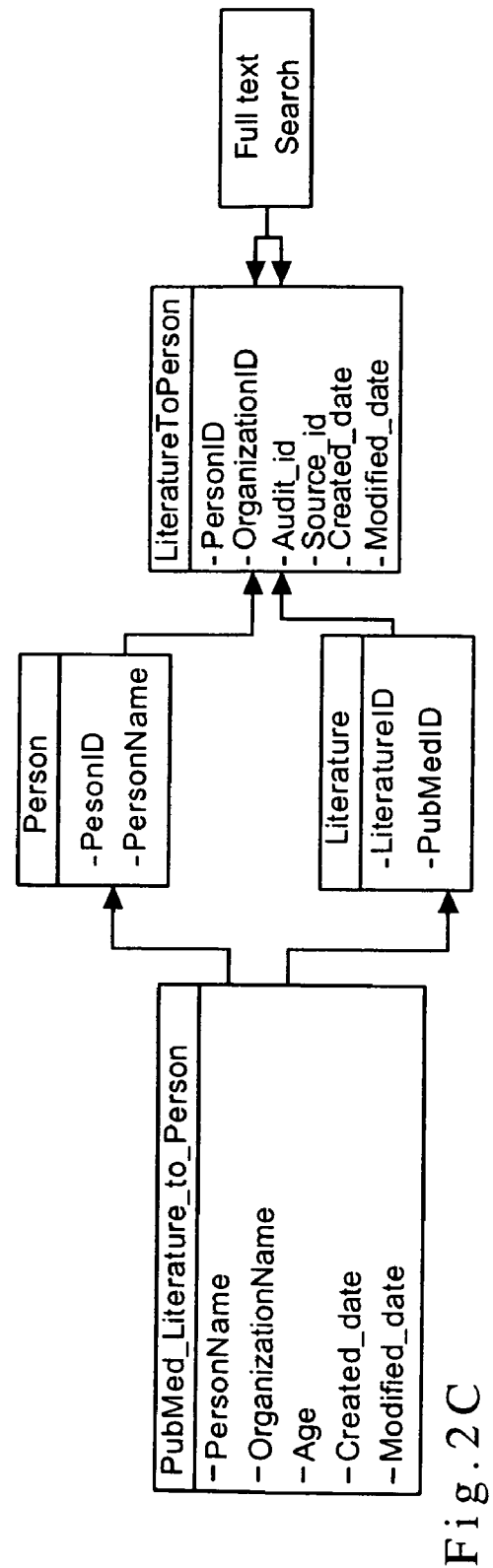
FIG. 2C a diagram representative of a field-to-text relationship in accordance with an embodiment of the present invention.

Referring now to FIGS. 2A-C, an exemplary knowledge model 140 for use in one embodiment of the knowledge discovery system 100 is shown. In the embodiment of FIGS. 2A-C, the knowledge model 140 defines an information space 200 for pharmaceutical research, and is represented by a relational database consisting of four distinct types of types. Entity tables define the content of the information space 200. In one embodiment, each entity table may include a name field (which may or may not be the primary key for that table) and attribute fields. Exemplary entity tables are shown in FIG. 2A.

Field-to-field relation tables define the relationships between the fields in the entity tables. In one embodiment, three types of field-to-field relationships exist. A name-to-name relationship relates two name fields from two entity tables. A name-to-attribute relationship relates the name of one entity to an attribute of another entity. An exemplary field-to-field relationship is shown in FIG. 2B. Finally, an attribute-to-attribute relationship relates the attribute of one entity to an attribute of another. Field-to-text relationships define the relationships between a fielded entity terms and the text of unstructured data. For example, the data model 140 may include a person table that defines people in the information space and a literature table that includes fields for various information about an article in the information space, but necessarily the text of the article. A text search of the article may be performed to determine if the person is mentioned in the article. An exemplary field-to-text relationship is shown in FIG. 2C. In one embodiment, each of the field-to-field relationship tables and the field-to-text relationship tables includes a field for the primary key of each entity referenced as well as managerial data, such as a date created field. The relationship tables are described in more detail below in reference to FIG. 5.

Figure 3:
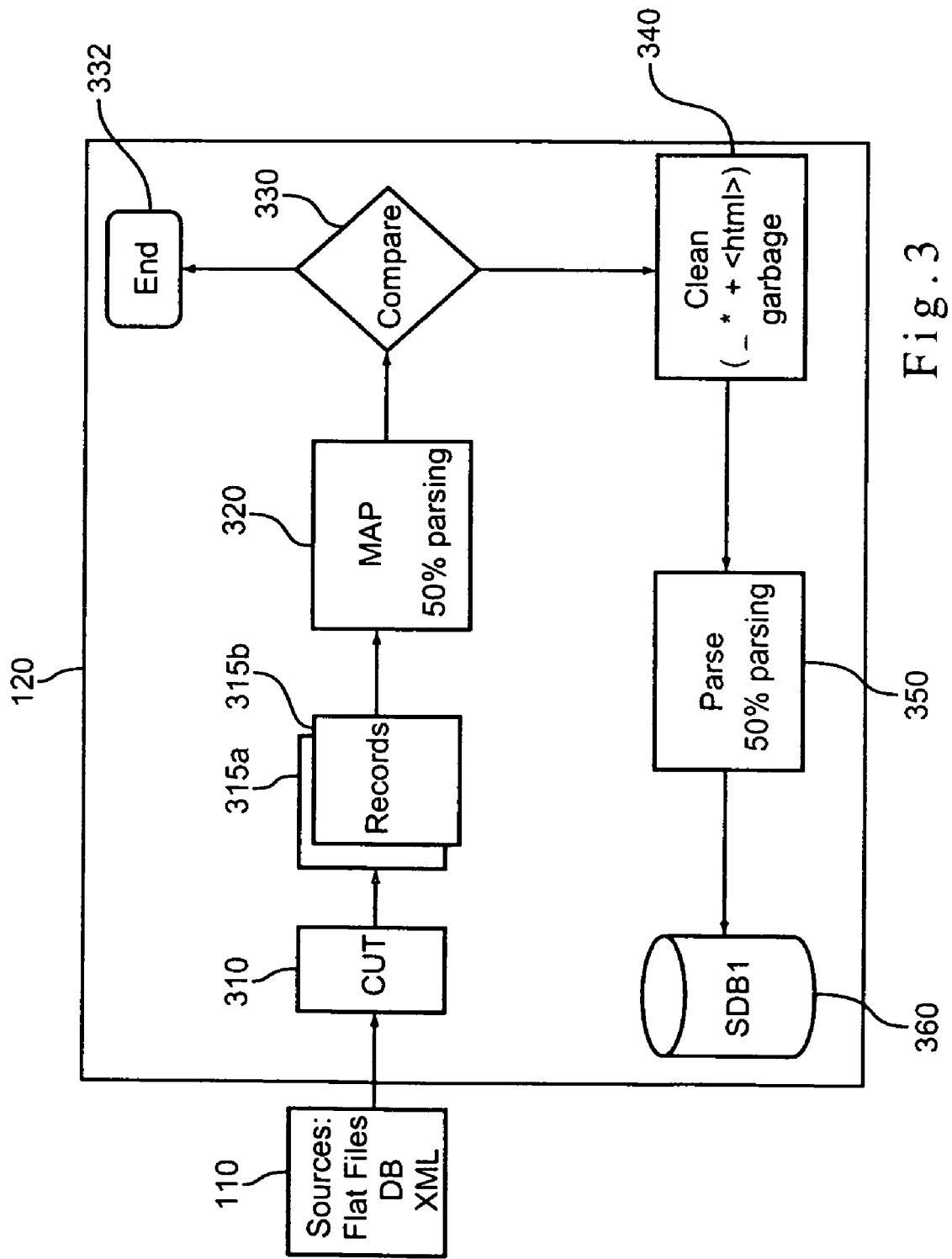
FIG. 3 is a diagram representative of an exemplary workflow for an extraction tool in accordance with an embodiment of the present invention.

Referring now to FIG. 3, an exemplary workflow for an extraction tool 120 in accordance with one embodiment is shown. Although the embodiment of FIG. 3 shows certain processes being performed by certain exemplary tools and components, it should be apparent to one of ordinary skill in the art that functions discussed below could be performed by any of the tools or components. In one embodiment, a plurality of data sources 110 is provided. As stated above, each data source may contain thousands of data items of stored in various types of files—XML, flat-files, HTML, text, spreadsheets, presentations, diagrams, programming code, databases, etc.—that include information belonging to the given domain. In the embodiment of FIG. 3, each data source 110 may contain documents of any type, created at any point in time. It should be apparent to one of ordinary skill in the art that other repository structures are contemplated by the present invention. For example, one data source may be provided containing every piece of information to be analyzed. In other embodiments, a plurality of data sources may be provided where each data source may contain only documents of certain types, created at discrete segments of time, or created at a certain geographical locations.

The extraction tool 120 extracts relevant information from the various data sources 110. Preferably, the extraction tool 120 is an asynchronous process that begins processing a file as soon as that file is retrieved from a data source 110. Alternatively, the extraction tool 120 may be implemented as a batch process. In one embodiment, each data source has an associated data source type. In one embodiment, each data source may be either an internal data source or an external data source. An internal data source is a data source that is internal to the organization utilizing the knowledge discovery system 100, whereas an external data source is a data source maintained by any other organization. Alternatively, or in addition to, the data source type may define the structure of the data source, such as the underlying directory structure of data source or the files contained therein. Additionally, the data source may be a simple data source consisting of a single directory, or a complex data source that may store metadata associated with each file kept in the data source. In one embodiment, the extraction tool 120 connects to each of the data sources 110 through data source adapters. An adapter acts as an Application Programming Interface, or API, to the repository. For complex data sources, the data source adapter may allow for the extraction of metadata associated with the information.

Exemplary data sources include PUBMED, a service of the National Library of Medicine that includes over 15 million citations for biomedical articles back to the 1950's, SWISS_PROT PROTEIN KNOWLEDGEBASE, which is an annotated protein sequence database established in 1986, the REFERENCE SEQUENCE (RefSeq) collection, which aims to provide a comprehensive, integrated, non-redundant set of sequences, including genomic DNA, transcript (RNA), and protein products, for major research organisms, KEGG, or the Kyoto Encyclopedia of Genes and Genomes, an ongoing project from Kyoto University, LOCUSLINK, a service of the National Library of Medicine that provides a single query interface to curated sequence and descriptive information about genetic loci, MESH, or Medical Subject Headings, the National Library of Medicine's controlled vocabulary thesaurus, OMIM, or Online Mendelian Inheritance in Man, a database catalog of human genes and genetic disorders, and NLM TAXONOMY, a searchable hierarchical index of names of all the organisms for which nucleotide or peptide sequences are to be found in certain data sources. Although each of these data sources constitutes a separate data source, the information in each data source has strong inter-relationships to information in others. Accordingly, the files stored in any particular data source 110 may include information relating the information therein. Referring to FIG. 2B, for example, the PUBMED data source 110 may include information 260 relating a particular person to an organization. This information can be used to determine a relationship definition 266 for a particular person 262 and organization 264 in the knowledge model 140. In one embodiment, a field-to-field relationship that has been determined from information obtained from a data source 110 is called a direct relationship. In one embodiment, all the field-to-field relationships are determined automatically using information from the data sources 110. In further embodiments, a file may include information relating information in itself to information in other data sources 110, or relating information in two separate data sources 110.

Optionally, the extraction tool 120 may include various parameters used to determine whether a document is relevant. These parameters may be predefined or configurable by a user. For example, a user may configure the extraction tool to only extract files from specified directories. It should be apparent to one of ordinary skill in the art that many other relevance parameters—for example, only certain file types or only files that have changed after a certain date—are contemplated by the present invention.

As stated above, the extraction process 120 retrieves files from the data sources 110. The original files may include large files that are of varying formats. In one embodiment, the extraction tool 120 includes a cut tool 310 that will split the original files into smaller records or documents 315a, 315b, etc. Preferably, the cut tool 310 will process the original files such that each record or document 315a, 315b includes one and only one data item. Alternatively, the cut tool 310 may generate records or documents 315a, 315b that include more than one data item. The original files may also include the information about all items in a single file, separating the information using delimiters. Exemplary delimiters include "///" or a blank line. A configuration file may be provided that details the delimiters used at a particular source. The configuration file may be used by the cut tool 310 to process the original files. In one embodiment, the cut tool 310 may include particularized processor application for processing a particular type of original file, such as an XML processor for cutting XML files or a text processor for manipulating text files. In one embodiment, these particularized processor applications are implemented as C# objects using the C# object-oriented programming language from Microsoft Corporation of Redmond, Wash.

Once the files are split into records or documents 315a, 315b, the extraction tool 120 preferably stores the records or documents 315a, 315b in a file system. Optionally, each record may include an identifier, such as an identifier used by the data source to identify the original file. Exemplary identifiers include a SWISS_PROT ID or a file name. Preferably, the extraction tool 120 also generates a global unique identifier for each record or document 315a, 315b. The global unique identifier is used for tracking purposes, as described below.

The extraction tool 120 may also be provided with a map tool 320. The map 320 functions to standardize the format of each record or document 315a, 315b. In one embodiment, the map tool 320 serves two functions. First, the map tool 320 may create a normalized specification for the records or documents 315a, 315b, such as a standardized XML specification. For example, records or documents 315a, 315b created from flat files may be transformed into xml files, while records or documents 315a, 315b created from XML files may be mapped to the standard XML specification. Second, the map tool 320 may remove information from the record or document 315a, 315b that is unnecessary to maintaining the knowledge model 140. In one embodiment, the map tool 320 outputs a single text string of XML.

Next, the compare tool 330 of the extraction tool 120 compares the records or documents 315a, 315b with those records or documents 315a, 315b that have already been integrated into the knowledge model so that only records or documents 315a, 315b that are new are further processed. As used herein, a new record or document 315a, 315b includes records or documents 315a, 315b that have been integrated into the knowledge model 140, but have since been modified. In other words, previously entered records or documents 315a and 315b may include only those records or documents that have been integrated into the knowledge model 140 and have not changed since their integration. In one embodiment, compare tool 330 will compute a value based on the record or document 315a, 315b. Preferably, the compare tool 330 uses a hash function to generate a hash value for each record or document 315a, 315b. The value may be based on any part of the record or document 315a, 315b, such as the identifier or the information contained therein.

Figure 4:
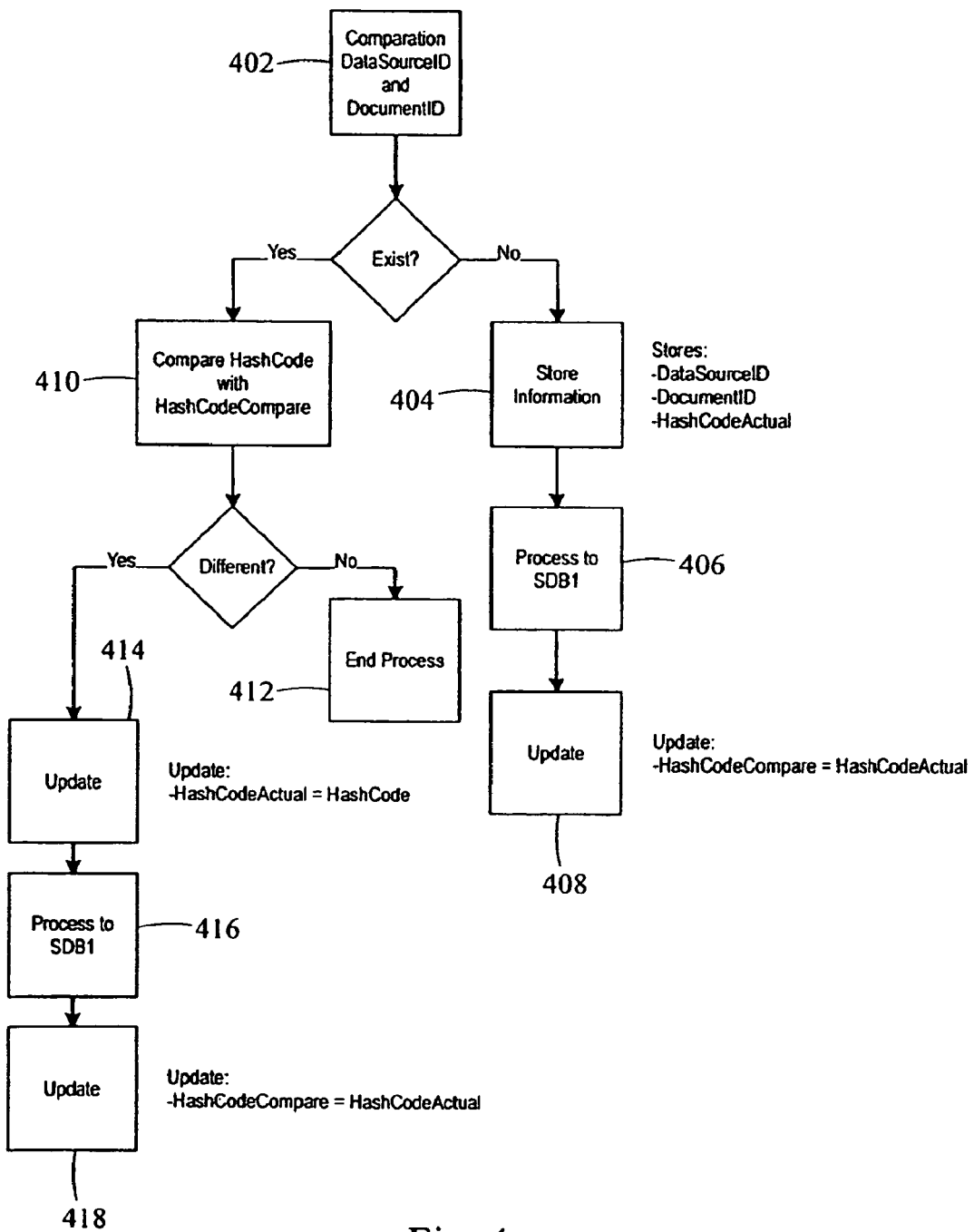
FIG. 4 is a diagram representative of an exemplary workflow for a compare tool in accordance with an embodiment of the present invention.

Referring now to FIG. 4, an exemplary workflow for a compare tool 330 is described in more detail. In the embodiment of FIG. 4, each record or document 315a, 315b has an associated identifier, DocumentID, as well as a data source identifier, DataSourceID, that identifies the data source from where the record or document 315a, 315b was retrieved. First, the compare tool generates a hash value, HashCode, for the current record or document 315a, 315b. Next, the compare tool 330 compares the DataSourceID and DocumentID for the current record or document 315a, 315b to a table of data for previously entered records or documents 315a, 315b at block 402. In the embodiment of FIG. 4, the table includes four items for each previously entered record or document 315a, 315b: a DataSourceID that identifies the data source; a DocumentID that identifies the record or document 315a, 315b; a first hash code value, HashCodeActual, that represents the hash code value for that record or document 315a, 315b before it is integrated into the knowledge model 140, and a second hash code value, HashCodeCompare, that represents the hash code value for that record or document 315a, 315b after it has been integrated into knowledge model 140. If no match is found in the table, this record or document 315a, 315b has never been previously integrated into the knowledge model. Accordingly, the compare tool 330 stores the current DataSourceID and Document ID in the table at block 404. Additionally, the HashCode will be stored as the HashCodeActual value for that record or document 315a, 315b. The extraction process 120 will continue to process the record or document 315a, 315b at block 406. Once the record or document 315a, 315b is integrated into the knowledge model 140, the HashCodeCompare value will be updated with the HashCodeActual value at block 408.

If a match is found in the table at block 402, the record or document 315a, 315b has been previously integrated into the knowledge model 140. The compare tool 330 next compares HashCodeActual to HashCodeCompare for the match. If two values are identical, the record or document 315a, 315b has not been modified since its last integration. Accordingly, the record or document 315a, 315b is not further processed as shown at block 412. If the values are different, the record or document 315a, 315b has been modified since its last integration. In this case, the compare tool 330 updates the HashCodeActual value with the current HashCode value at block 414. The extraction process 120 will continue to process the record or document 315a, 315b at block 416. Once the record or document 315a, 315b is integrated into the knowledge model 140, the HashCodeCompare value will be updated with the HashCodeActual value at block 418.

At this point, the only records or documents 315a, 315b to be processed are new records or documents 315a, 315b that have been properly formatted. However, the information contained therein may contain unnecessary information as a consequence of different data sources using different nomenclatures. For example, an attribute name may be preceded by an asterisk or dash. Alternatively, the record or document 315a, 315b may contain HTML tag information. In one embodiment, the extraction process 120 is provided with a clean tool 340 that removes this unnecessary information from the records or documents 315a, 315b.

Once the record or document 315a, 315b is cleaned, the parse tool 350 of the extraction tool 120 restructures the information of the record or document 315a, 315b. For example, if a record or document 315a, 315b includes an XML attribute tag containing multiple values separated by a delimiter, the parse tool 350 may each value into separate tags. Additionally, the parse tool 350 may unifies the different nomenclatures of the records or documents 315a, 315b so that the information from the different sources is coherent. For example, an Organism name may be listed under a first label in one data source 110 and a second label 110 in another data source. The parse tool 350 may standardize this information.

Finally, the extraction process 120 may store the record or document 315a, 315b to be integrated into the knowledge model. In the embodiment of FIG. 3, the record or document 315a, 315b is stored in a database 360. Alternatively, the record or document 315a, 315b may be stored in any manner that is apparent to one of ordinary skill in the art. In yet another embodiment, the record or document 315a, 315b is transmitted as part of a message to the integration process 130. Preferably, the extraction tool 120 stores the record or document 315a, 315b in a database 260 and sends a message that alerts the integration tool 130 that a new record or document 315a, 315b has been inserted. In one embodiment, the message may be a field in the database 260 which is polled by the integration tool 130.

Figure 5:
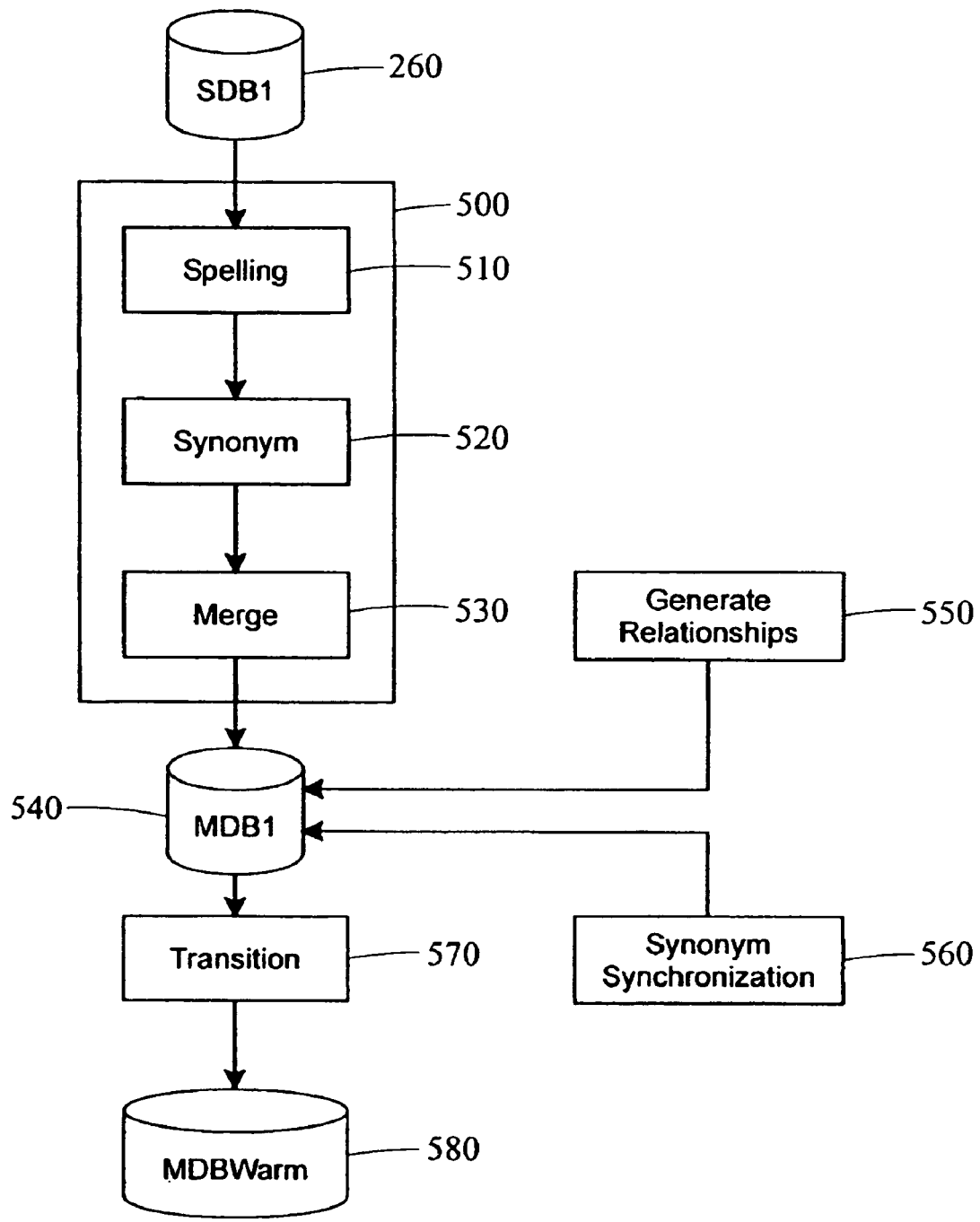
FIG. 5 is a diagram representative of an exemplary workflow for an integration tool in accordance with an embodiment of the present invention.

Referring now to FIG. 5, an exemplary workflow for the integration process 130 is shown. Preferably, the integration process is an automatic, asynchronous process that doesn't need the entire extraction process 120 to finish. For example, in the embodiment of FIG. 5, the integration process 130 may begin integrating a record or document 315a, 315b as soon as it is inserted into the database 360. This entry may be treated and integrated in an individual way and is passed through several components whose purpose is to integrate this source register into the knowledge model 140. The integration tool 130 provides the users with more complete and higher quality information than the data sources 110 alone.

In the embodiment of FIG. 5, the integration tool 130 only processes new records or documents 315a, 315b because the extraction tool 120 has removed those records or documents 315a, 315b that have not been updated since the prior integration. This greatly improves the performance of the integration tool 130, reducing the time necessary to complete the integration process. However, the integration tool 130 is equally capable of integrating any types of records or documents 315a, 315b, regardless of whether they have been integrated previously.

In one embodiment, the integration tool 130 may receive information to integrate in three ways. First, the integration tool 130 may receive information from the extraction tool 120. For example, the extraction tool 120 may process a record or document 315a, 315b from a data source, insert the record or document 315a, 315b into a database 360, and alert the integration tool 130 of the presence of the new information. In response, the integration tool 130 may retrieve the information from the database 360. Second, the integration tool 130 may receive information from a re-integration batch process. The re-integration batch process may build a message (of a similar format to those generated by the extraction process 130) that alerts the integration process 130 to the presence of a record or document 315a, 315b that could not be integrated into the knowledge model 140 during a previous attempt. Finally, custom applications may be developed to alert the integration tool 130 of information from particular data sources 110 that do not require the full functionality of the extraction tool 120. For example, an internal data source 110 may be provided that includes files that adhere to a particular structure designed to ease the integration process. It should be apparent to one of ordinary skill in the art that any method may be used to introduce a record or document 315a, 315b to the integration tool 130.

The integration tool 130 may be provided with an integrate tool 500. The integrate tool 500 performs four primary processes. First, the integrate tool may retrieve a record or document 315a, 315b from the database 360. Next, the integrate tool 500 may perform a spell check function 510 on the data included in the record or document 315a, 315b to ensure that misspellings in the original data source 110 files do not effect the integrity of the knowledge model 140. Similarly, the integrate tool 500 may perform a synonym function 520 to determine if the current term (as used in the record or document 315a, 315b) is a synonym for a preferred name. Finally, the integrate tool 500 may perform a merge function 530 that integrates the record or document 315a, 315b into a database 540. In one embodiment, the database 540 represents a un-optimized version of the knowledge model 140. A particular embodiment of the integrate tool 500 is discussed in more detail below in reference to FIGS. 9-13.

The integration tool 130 may also be provided with various batch-process tools to perform various functions on the information in the database 540. In the embodiment of FIG. 5, the integration tool 130 includes a relationship generation tool 550 that may be used to analyze the information in the database 540. The relationship generation tool 550 is discussed in more detail below in reference to FIG. 14. Similarly, a synonym synchronization tool 560 may run periodically to update the information in the database 540 in accordance with the most recent list of synonyms. Finally, a transition tool 570 may be provided to optimize the information in the database 540 to create the knowledge model 140. For example, the transition tool 570 may denormalize the information in the database 540, generate cross-over tables, build indices on clustered indices on the primary key columns of various tables of the database 540, and optimize the database 540 for queries and data retrieval tasks. In one embodiment, the transition tool 570 generates a database 580 that is replicated in a production environment as the knowledge model 140.

Figure 6:
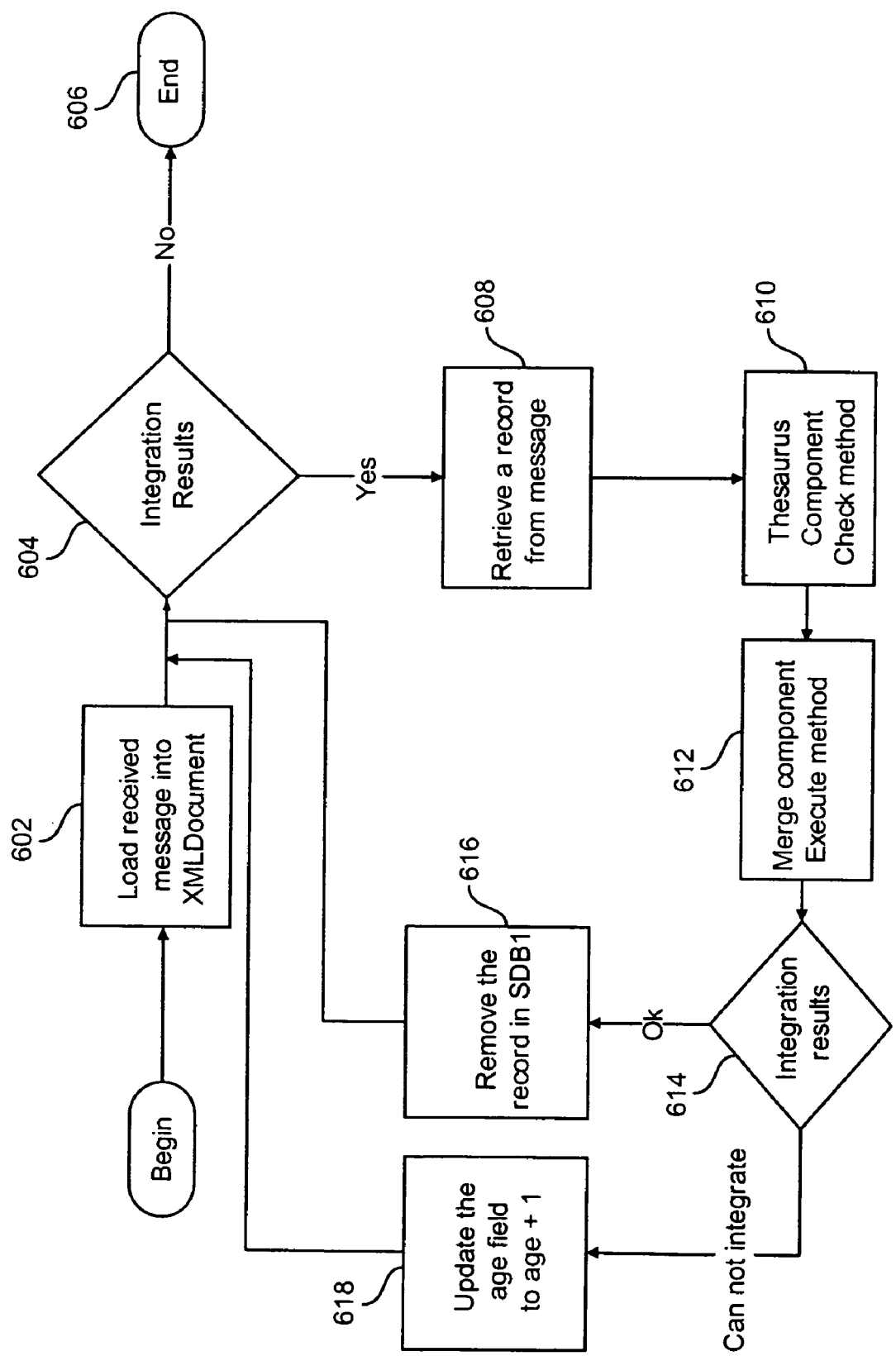
FIG. 6 is a diagram representative of an exemplary workflow for an integrate tool in accordance with an embodiment of the present invention.

Referring now to FIG. 6, the workflow for one embodiment of the integrate tool 500 is shown. As described above, the extraction tool 120 may send a message to the integrate tool 130 to inform the integration tool 130 that new entries in the database 360 need to be integrated into the knowledge model 140. The message may also indicate that the entries are from a particular data source 110. Initially, the integrate tool 500 creates an XMLDocument object. The XMLDocument object is a working version of a standard configuration file. In one embodiment, each data source has a standard configuration file in XML that acts as template for the integration tool 130. An exemplary configuration file is shown in Table 1. It should be apparent to one of ordinary skill in the art that various types of configuration files in other formats are contemplated by the present invention.

TABLE 1

Sample XML Data Source Configuration File

```
<DataSource Name="DataSourceName">
  <SDB1Table Name="SDB1TableName">
    <Thesaurus>
      <SDB1FieldThesaurus Name="FieldName"
      ThesaurusSP="ThesaurusSPName" SpellingSP
      ="SpellingSPName" />
      ...
    </Thesaurus>
    <LookUp SPName="SPName">
      < SDB1FieldLookUp Name="SDB1FieldName"
      GetIDSP="SPGetID"/>
      ...
    </LookUp>
    <Compare>
      <SDB1FieldCompare Name="SDB1FieldName"
      MDB1Field="MDB1FieldName">
      ...
    </Compare>
    <Insert SPName="StoredProcToInsert">
      <SDB1FieldInsert Name="SDB1FieldName"
      ConfidenceValue="ConfidenceValue"/>
      ...
    </Insert>
    <Update SPName="StoredProcToInsert">
```

TABLE 1-continued

Sample XML Data Source Configuration File

```
    <SDB1FieldUpdate Name="SDB1FieldName"
    ConfidenceValue="ConfidenceValue"
    Type="U/A" DB1FieldName="MDBFieldName"
    MDB1ConfidenceValue="MDB1ConfidenceField
    Name"/>
    ...
  </Update>
</ SDB1Table >
...
</DataSource>
```

As shown, the configuration file includes various attributes that are used in later stages of the integration process. The exemplary configuration file includes five attributes, a Thesaurus attribute, a LookUp attribute, a Compare attribute, an Insert attribute, and an Update attribute. The thesaurus attribute includes information in the record that need to be checked for spelling and/or synonyms. In particular, the thesaurus attributes define a field name to be checked and the values for that field name. This value will appear in ThesaurusSP and SpellingSP attributes if the value needs to be checked for synonyms or spelling, respectively. If both the value needs to be checked for both spelling and synonyms, it will appear in both attributes. The LookUp attribute defines each field in the database 360 and the name of a procedure that can be used to lookup the associated row in the knowledge model 140. The Compare attribute defines the field in the database 360 and its corresponding field in the knowledge model 140. The Insert attribute defines each field in the database 360 and its corresponding confidence value, as described below. Finally, the Update attribute defines each field in the database 360, its corresponding confidence level, the field type, and the corresponding field in the knowledge model 140 and its corresponding confidence value. In one embodiment, two field types are defined. An update type implies that the value of the field should be replaced in its entirety if a new record or document 315a, 315b is to replace an existing entry in the knowledge model 140. An append type implies that the information in the new record or document 315a, 315b should be appended to the current information.

As stated above, each field includes an associated confidence value. The confidence value is used score the reliability of the data sources 110 for each field of the knowledge model 140. For example, multiple data sources 110 may include information for one field of the knowledge model 140. To resolve this conflict, the confidence value is used to determine which data source is more reliable for a given field. The confidence value may reflect an internal view of the reliability of the data sources 110 (i.e. the view of the system developers or the organization utilizing the knowledge discovery system 100) or may reflect an external view of reliability (i.e. the use of a third party reliability standard). In one embodiment, the confidence value is a numerical value from 1-20 where the confidence value increases with the reliability of the data source 110. In one embodiment, each of the plurality of data sources 110 is ranked from 1 to N for each field of the knowledge model, where N is the number of data sources 110. Alternatively, multiple data sources 110 may be equally reliable and therefore have the same confidence value. In such an embodiment, the integration tool 130 may chose the most recent record or document 315a, 315b as controlling. Alternatively, the integration tool 130 may only replace a field if the confidence value of the new record or document 315a, 315b is greater than the current entry.

In one embodiment, a confidence value configuration file is provided. The confidence value configuration file may define a confidence value for each field of the knowledge model 140 and for all data sources 110. Alternatively, a separate confidence value configuration file may be provided for each data source 110. It should be apparent to one of ordinary skill in the art, that various ways of tracking the reliability of a data source 110, as well as various types of configuration files, are contemplated herein. An exemplary XML confidence value configuration file is shown in table 2. In the exemplary confidence value configuration file, each field of each table from each data source 110 is ranked.

TABLE 2

Sample XML Confidence Value Configuration File

```
<Table>
    <DataSource1>
        <field1> ConfidenceValue </field1>
        ...
        <fieldn) ConfidenceValue </fieldn>
    </DataSource1>
    ...
</Table>
```

Figure 7:
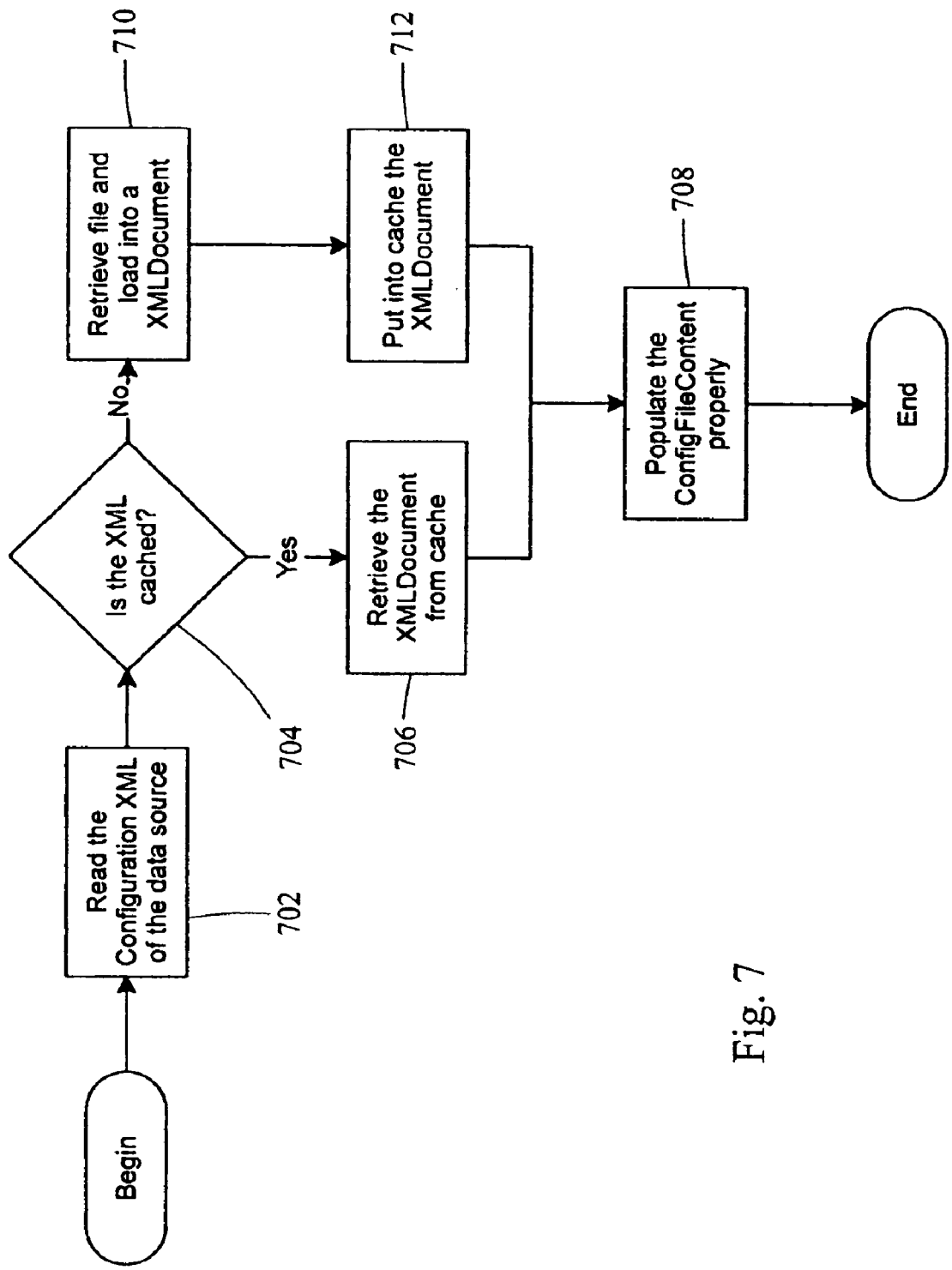
FIG. 7 is a diagram representative of an exemplary workflow for loading the information of a received message in accordance with an embodiment of the present invention.

Referring now to FIG. 7, an exemplary workflow for the loading the information from a received message into an XMLDocument object is shown. First, the integrate tool 500 reads the configuration file for the data source identified in the message at block 702. Next, a check is performed to determine if an XMLDocument object for this data source is cached at block 704. If so, the XMLDocument object is retrieved from the cache at block 706, and the information from the message is used to populate the ConfigFileContent property of the XMLDocument at block 708. If no XMLDocument object for the particular data source is in the cache, the integrate tool 500 will create a new XMLDocument object and load it with the configuration file information at block 710, put the new XMLDocument in the cache at block 712, and populate the ConfigFileContent property of the XMLDocument with the information from the message at block 708.

Returning to FIG. 6, after loading the received message into an XMLDocument object at 602, the integrate tool 500 next checks to see if the message contains a record or document 315a, 315b that needs to be integrated into the knowledge model at block 604. If the message does not contain any additional records or documents 315a, 315b that need to be integrated, the process ends at block 606. If the message does contain a record or document 315a, 315b that needs to be integrated, the integrate method retrieves that record or document 315a, 315b from the database 360 at block 608. Next, the integrate tool 500 calls the thesaurus component to perform the spelling function 510 and synonym function 520 at block 610. In the embodiment of FIG. 6, the thesaurus component includes an internal source, such as a database, with containing information on commonly misspelled words and synonyms or preferred words. In either case, the thesaurus component will replace the misspelled or non-preferred word with the proper word. Alternatively, an external source may be used by the thesaurus component.

Figure 8:
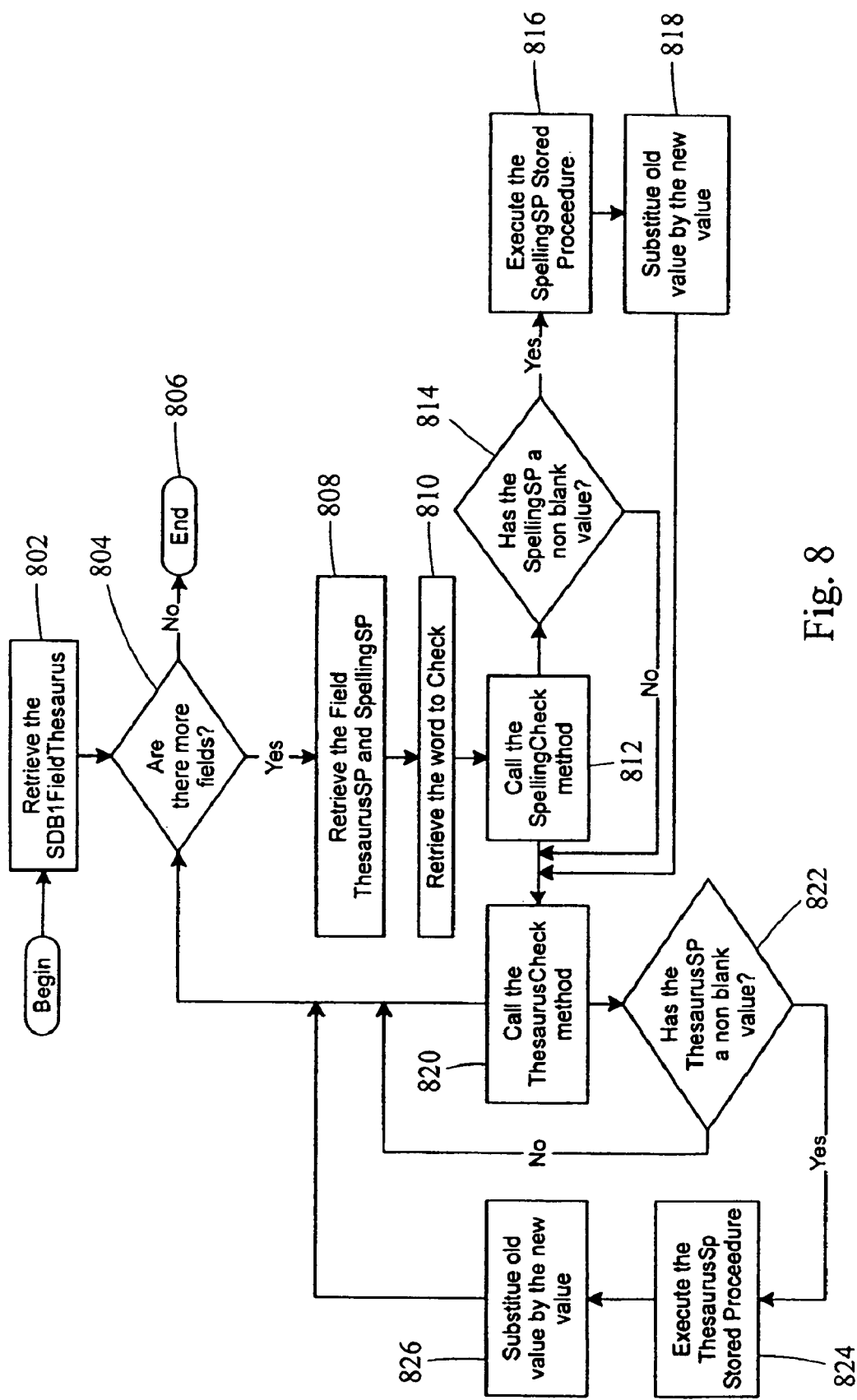
FIG. 8 is a diagram representative of an exemplary workflow for a Thesaurus component in accordance with an embodiment of the present invention.

Referring to FIG. 8, an exemplary workflow for the Thesaurus component is shown. First, the Thesaurus component retrieves the field names from the XMLDocument Thesaurus attribute at block 802. Next, the Thesaurus component will check to determine if any more fields need to be checked at block 804. If no more fields need to be checked, the Thesaurus component will exit at block 806. If a field needs processing, the Thesaurus component will retrieve the corresponding ThesaurusSP and SpellingSp values at block 808. Next, the Thesaurus component will retrieve the word to check at block 810, and call the SpellingCheck procedure at block 812. The SpellingCheck procedure first determines if the SpellingSp value is non-blank at block 814. If the SpellingSp value is non-blank, the SpellingSP procedure is executed at block 816. In one embodiment, the SpellingSp procedure checks the SpellingSp value against a spellings table that includes the correct word and various misspellings. When the correct word is found, it is substituted for the old value at block 818. At this point, or if the SpellingSp value is determined to be blank at block 814, the Thesaurus component moves on to the ThesaurusCheck procedure at block 820. Similar to the SpellingSp procedure, the ThesaurusCheck procedure first determines if the ThesaurusSP value is non-blank at block 822. If the ThesaurusSP value is non-blank, the ThesaurusSP procedure is executed at block 824. In one embodiment, the ThesaurusSP procedure checks the ThesaurusSP value against synonym table that includes a preferred word and various synonyms. When the correct word is found, it is substituted for the old value at block 824. The Thesaurus component then returns to block 804 to determine if any additional fields need to be checked, and continues to loop until all the fields have been processed.

Returning to FIG. 6, once the Thesaurus component has finished, the record or document 315*a*, 315*b* is passed to the Merge component at block 612. In order to make the knowledge model 140 a richer source of information than any one underlying data source 110, the knowledge model 140 typically includes more information on a given entity than any single data source 110. The Merge component is used to update the knowledge model 140 with the new records or documents 315*a*, 315*b* stored in the database 360 and assimilate the various pieces of information from the various data sources 110. In one embodiment, the Merge component takes a single record or document 315*a*, 315*b* and uses it to fill a single row in the database 540. First, the Merge component has to determine if the information provided by the record or document 315*a*, 315*b* complements the existing information or it represents new information. Depending on the comparison, the record or document 315*a*, 315*b* is either inserted into the database 540 as a new row or used to update the contents of an existing row. In one embodiment, four tools are used to accomplish these tasks. First, the Merge component may include a LookUp component that is used to determine if the record or document 315*a*, 315*b* can be integrated into the knowledge model and if the record or document 315*a*, 315*b* is entirely new, for example, if there is now row in the database 540 that corresponds to this record or document 315*a*, 315*b*. If a row exists that corresponds to this record or document 315*a*, 315*b*, the Merge component may utilize a Compare component to determine if the existing row in the database 540 includes null values in the fields to be modified by the record or document 315*a*, 315*b* to be processed. If not, a new row may be added to the database 540. If the row does include null values, that information must be updated with the information in the record or document 315*a*, 315*b*. Depending on the results of these tests, an Insert component may be used to add a new row or an Update component may be used to update a row.

Figure 9:
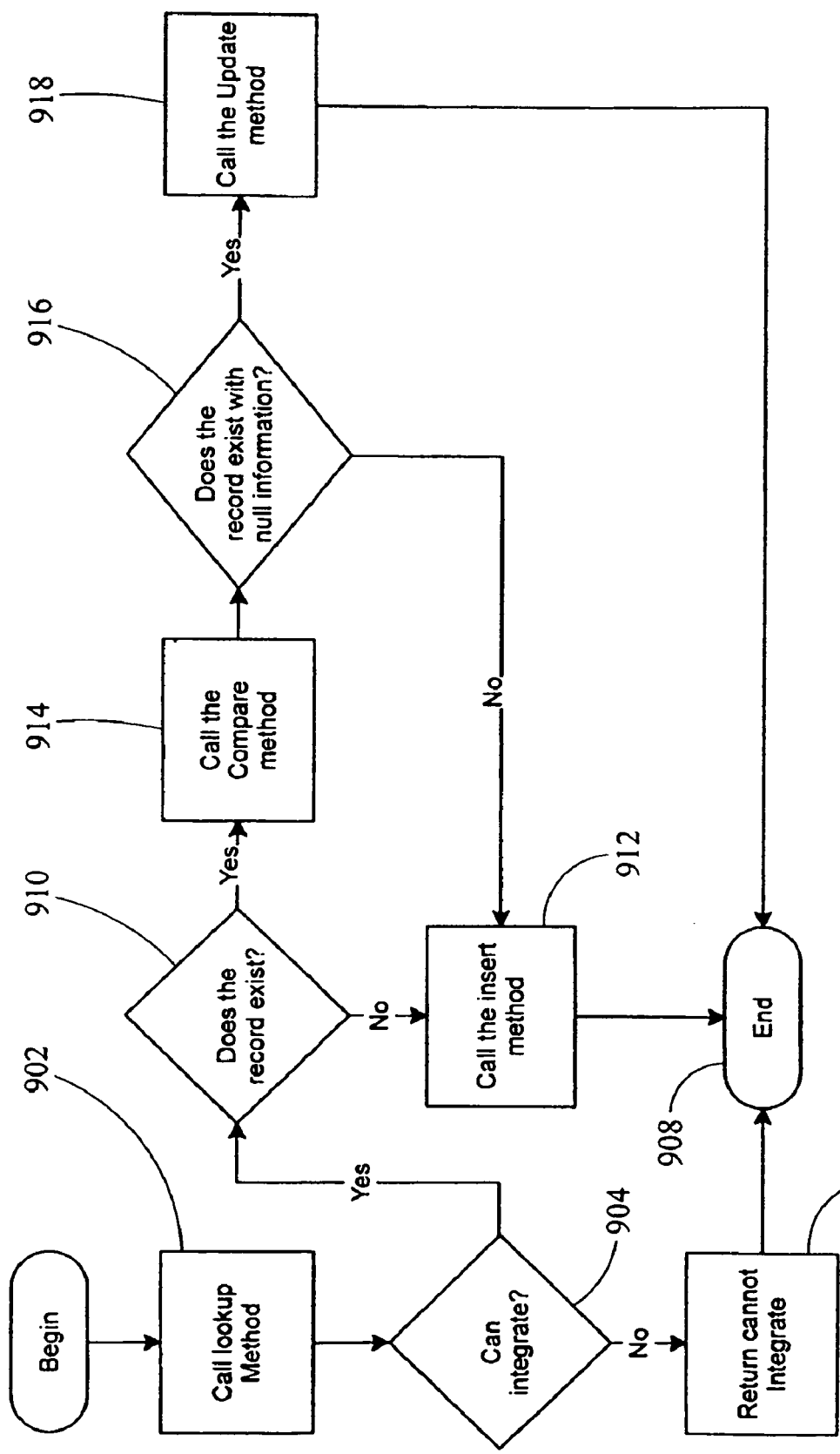
FIG. 9 is a diagram representative of an exemplary workflow for a Merge component in accordance with an embodiment of the present invention.

Referring now to FIG. 9, an exemplary workflow for an embodiment of the Merge component is shown. First, the Merge component calls the LookUp component at block 902, which determines if the record or document 315*a*, 315*b* can be integrated at block 904. If the record or document 315*a*, 315*b* cannot be integrated, the Merge component returns this information to the integrate tool 500 at block 906 and exits at block 908. If the record or document 315*a*, 315*b* can be integrated, the LookUp component then determines if the record exists at block 910. If not, the record or document 315*a*, 315*b* is then passed to the Insert component at block 912, and the Merge component ends at block 908. If the record does exist, the Compare component is called to determine if the record exists with null information at block 916. If the record does not include null information, the record or document 315*a*, 315*b* is passed to the Insert component at block 912 and the Merge component exits at block 908. If the record does not include null information, the record or document 315*a*, 315*b* is passed to the Compare component at block 918 and the Merge component exits at block 908.

Figure 10:
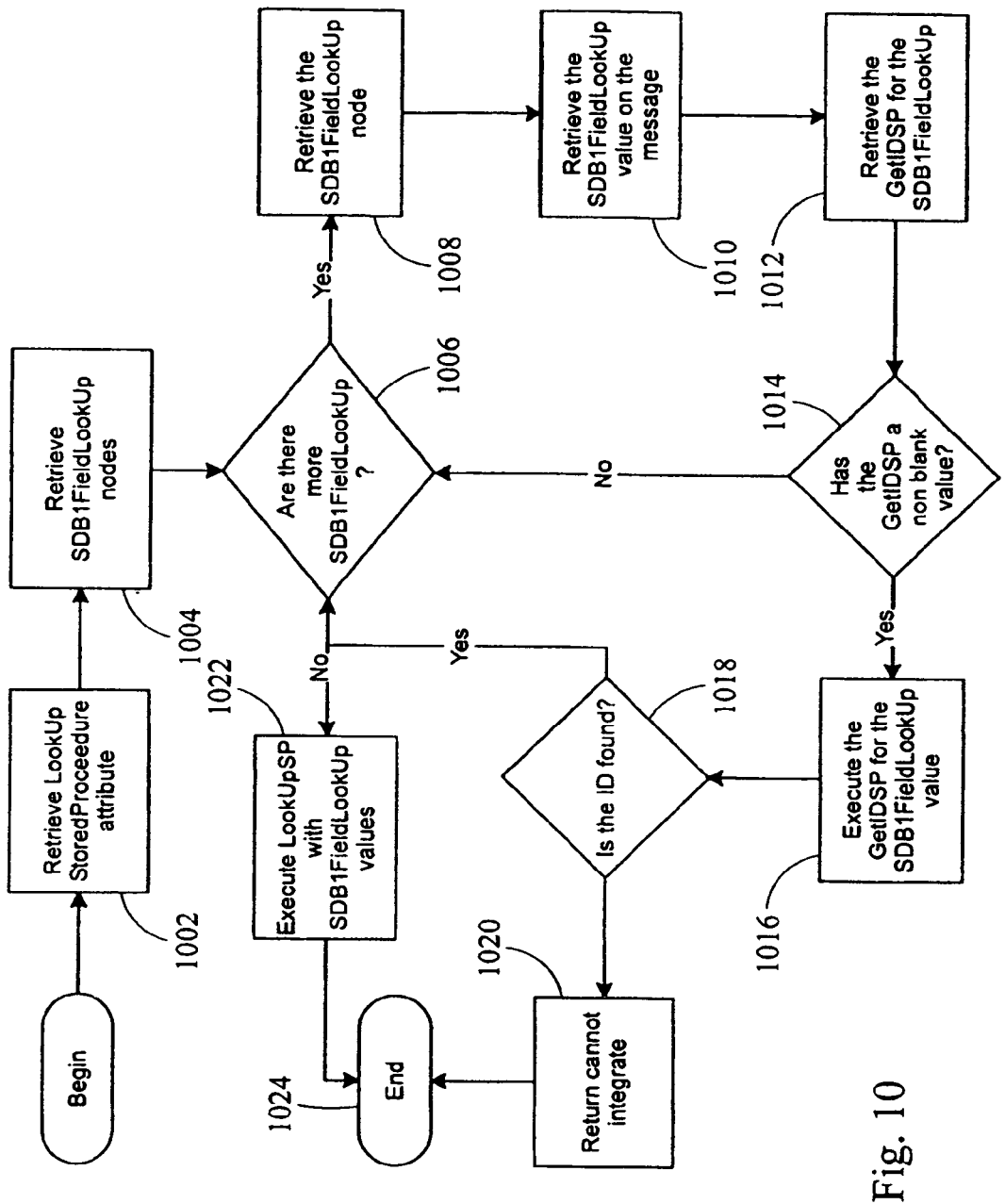
FIG. 10 is a diagram representative of an exemplary workflow for a LookUp component in accordance with an embodiment of the present invention.

Referring now to FIG. 10, an exemplary workflow for an embodiment of the LookUp component is shown. First, the LookUp component retrieves the StoredProcedure attribute from the XMLDocument object, as described above, at block 1002. Next, the LookUp component retrieves the first field information from the database 360 which need to be checked at block 1004. At block 1006, the LookUp component determines if any additional fields need to be processed. If so, the LookUp component compiles a dataset of all the values that need to be looked up. To do this, the LookUp component retrieves the additional field from the value at blocks 1008 and 1010, and determines the corresponding table in the database 540 for this field at block 1012. If the value is not found in the database 540, the LookUp component performs a lookup function on the value for the fields at block 1016 and determines if the ID for that value is found at block 1018. If the ID is not found, the LookUp component checks the record to be re-integrated later at block 1020, informs the integrate tool 500 that the record could not be integrated at block 1020, and exits at block 1024. If the ID is found, the LookUp component will return to block 1006 and continue compiling the list of fields to look up. Once there are no additional fields to look up, the LookUp component determines if the records exist at block 1022 and exits at block 1024.

Figure 11:
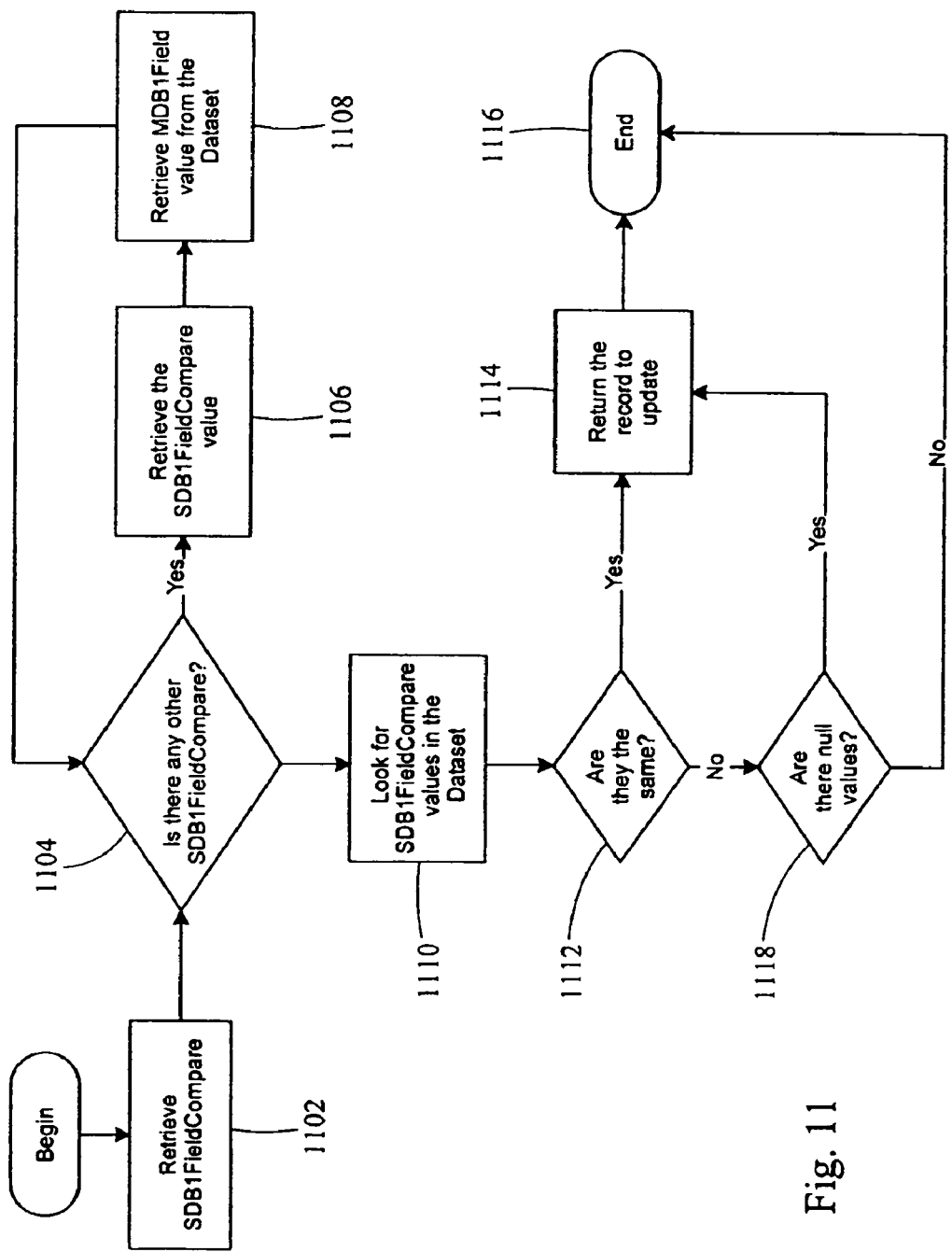
FIG. 11 is a diagram representative of an exemplary workflow for a Compare component in accordance with an embodiment of the present invention.

Referring now to FIG. 11, an exemplary workflow for the Compare component is shown. First, the Compare component retrieves the XMLDocument Compare attribute at block 1102. Next, the Compare component compiles a dataset of all the values in the record that need to be compared at blocks 1104, 1106 and 1108. Once this dataset is compiled, the Compare component determines if any values in this dataset are included in the dataset determined by the LookUp component at block 1110. If so, those records are returned to the Update component, as described above, at block 1114 and exits at block 1116. If the values are not the same, the Compare component then determines if the values are null. If so, those records are returned to the Update component, as described above, at block 1114 and exits at block 1116. If the values are not null, the Compare component exits at block 1116.

Figure 12:
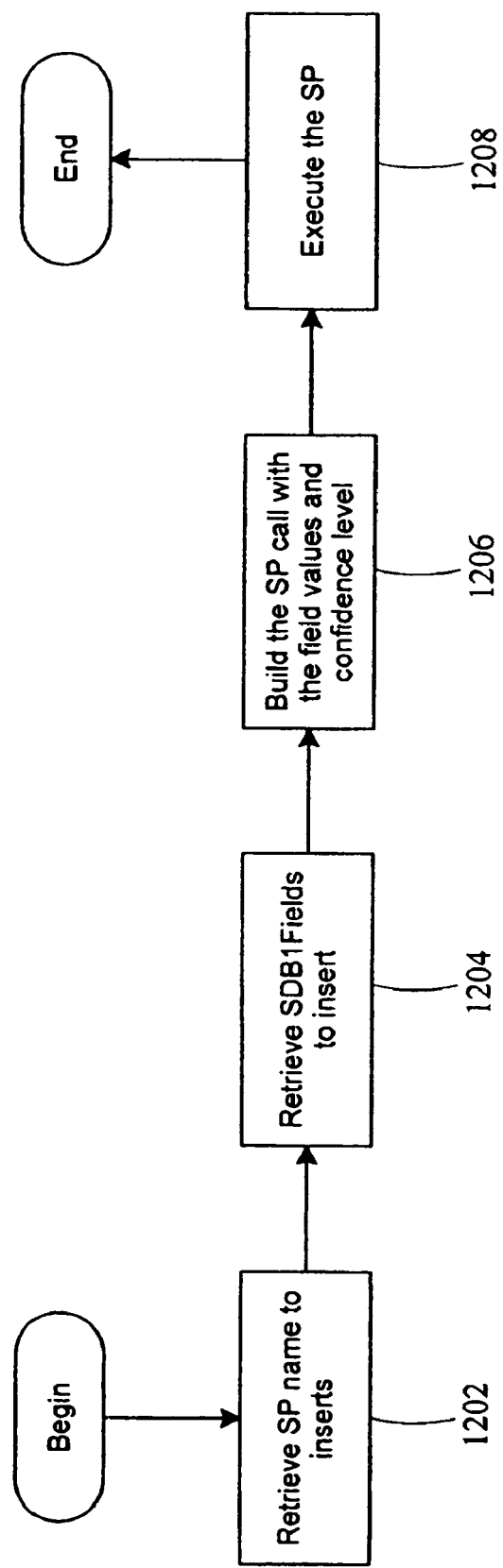
FIG. 12 is a diagram representative of an exemplary workflow for an Insert component in accordance with an embodiment of the present invention.

Referring to FIG. 12, an exemplary workflow for an Insert component is shown. First, the Insert component retrieves the stored procedure name that performs the actual inserts at block 1202. Next, the Insert component retrieves the field values and confidence levels from the XMLDocument object, as well as the values from the database 360 for the record to be inserted at block 1204. Using this information, the Insert component builds a call to the stored procedure to insert the new information at block 1206. Finally, the call is executed at block 1208.

Figure 13:
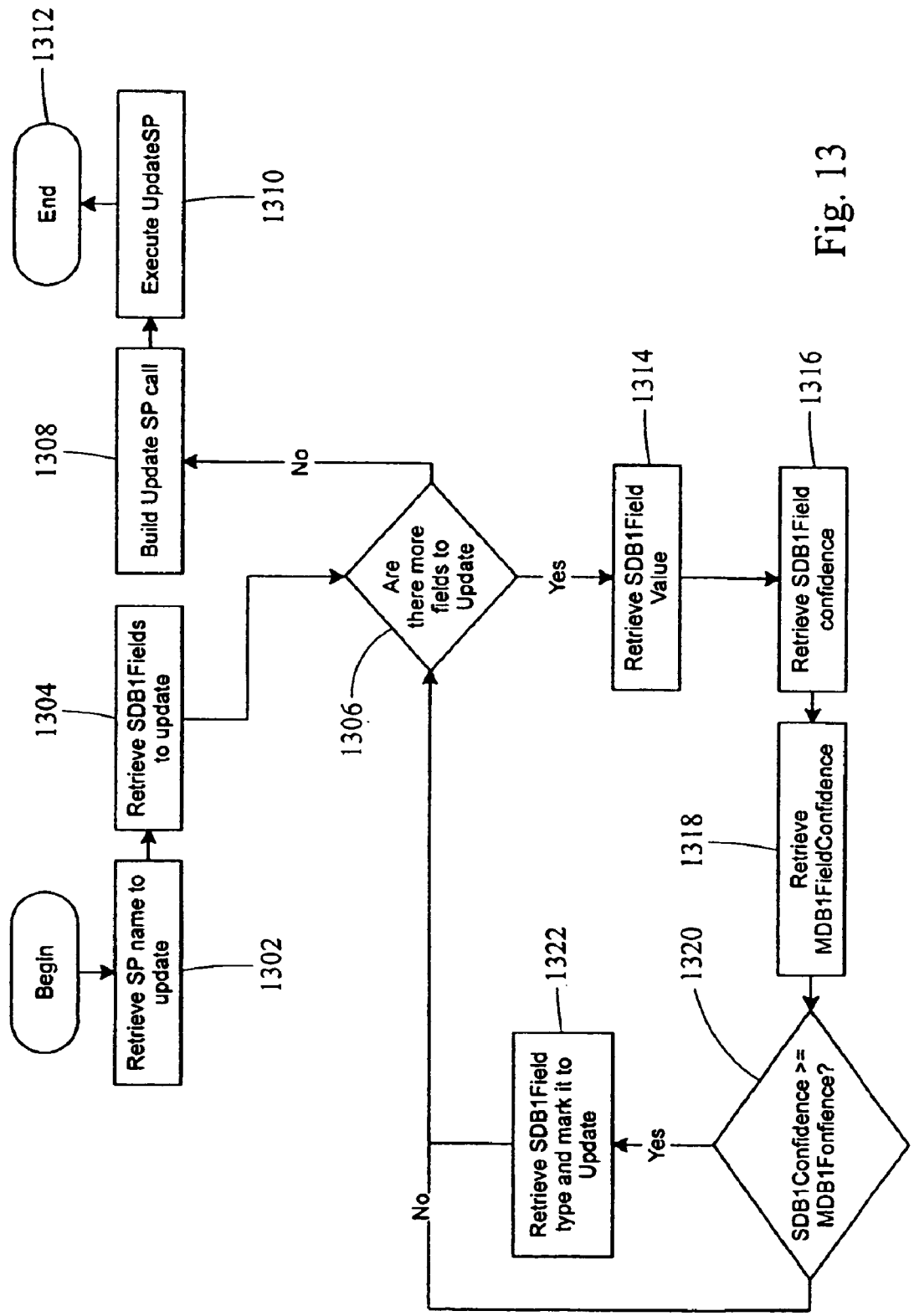
FIG. 13 is a diagram representative of an exemplary workflow for a Update component in accordance with an embodiment of the present invention.

Referring now to FIG. 13, an exemplary workflow for an Update component is shown. First, the Update component retrieves the name of the stored procedure that performs the actual update at block 1302. Next, it reads the Update attribute from the XMLDocument object at block 1304. A check is performed to determine if there any more fields in the Update attribute that need to be processed at 1306. If so, the Update component retrieves the field value and corresponding confidence level from record or document 315*a*, 315*b* at blocks 1314 and 1316, respectively. It then retrieves the confidence level of the current entry in the knowledge model 140, and compares the two confidence values at block 1320. If the confidence value for the new field is greater than the current confidence value, the new field is marked to 'Update', meaning that this new value should replace the existing value, at block 1322. If the current confidence value is greater than the new confidence value, however, the current value will not be overwritten. The Update component continues in this manner until all of the update fields have been processed. When there are no additional fields to process, the Update component builds the procedure call at block 1308, executes the call at block 1310, and exits at block 1312.

Returning to FIG. 6, once the Merge component has finished processing the records or documents 315*a*, 315*b* from the message, a check is made to determine the result at block 614. If the process was successful, the record or document is removed from the database 360 at block 616, and the integrate tool 500 returns to block 604 to process the next record in the message. Alternatively, if the Merge component was unsuccessful, the age field for the record is incremented at block 618, and the integrate tool 500 returns to block 604 to process the next record in the message. The concept of "age" appears as a result of the automatic, asynchronous nature of the integration process. For example, as described above, the merge component can be used to merge entities or relationships. A potential problem could arise if the system attempts to merge a relationship before one of entities of the relationships exists in the knowledge model 140, such as a relationship that defines a relation between entities a and b before entity b exists in the knowledge model 140. The re-integration batch process described above may be used to reintroduce these records or documents 315*a*, 315*b* at a later time. In one embodiment, the records or documents 315*a*, 315*b* may be deleted if their 'age' reaches a particular level, for example, 10. Alternatively, or in addition to, either the integration or re-integration process may determine if a record or document 315*a*, 315*b* covering the same field and from the same data source 110 has been integrated subsequently. If so, the integration of the 'old' record or document 315*a*, 315*b* is no longer necessary, and it may be deleted.

Figure 14:
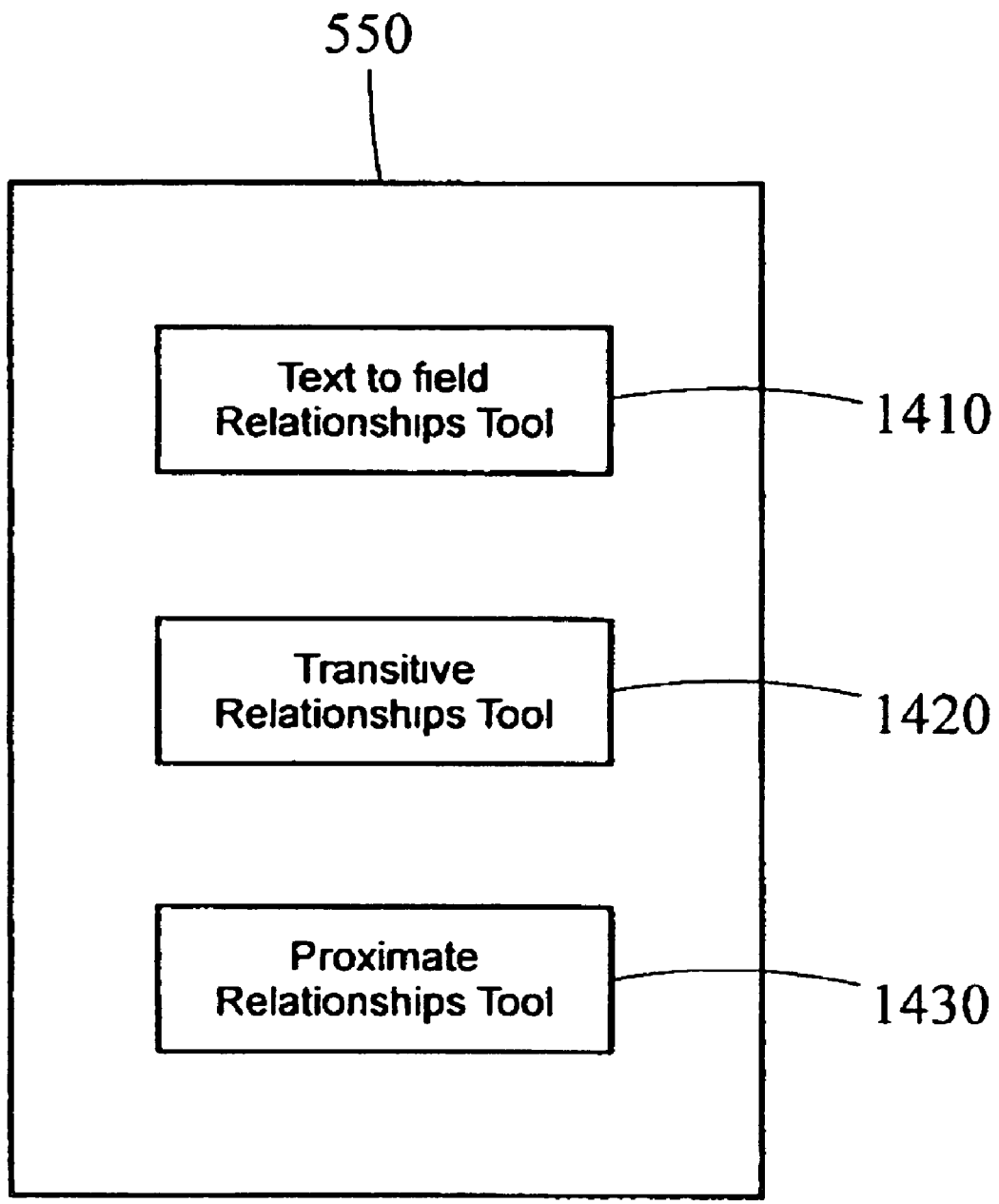
FIG. 14 is a diagram representative of an exemplary relationship generation tool in accordance with an embodiment of the present invention.
Figure 15:
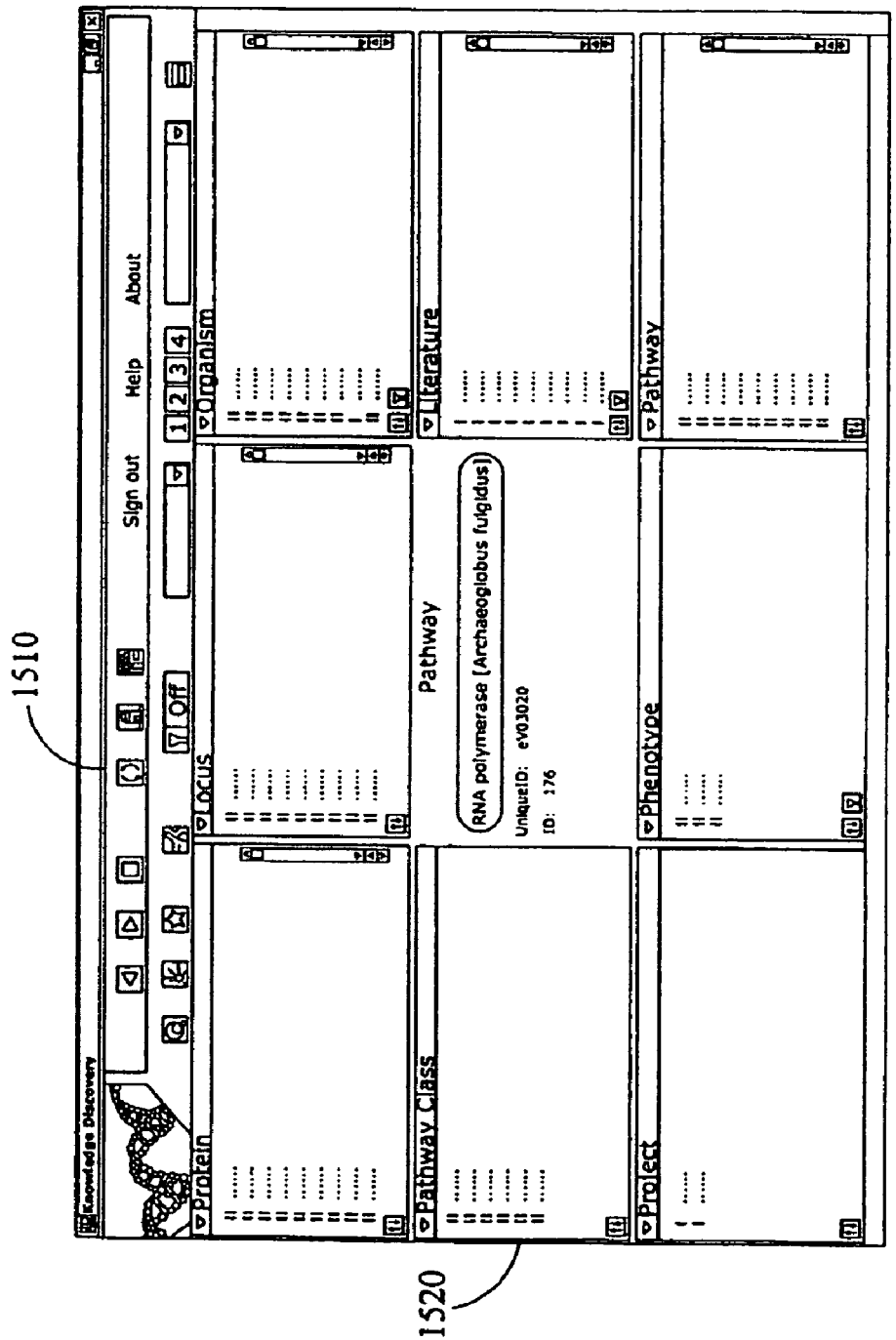
FIG. 15 is an exemplary screen shot of a navigator tool in accordance with an embodiment of the present invention.

Referring now to FIG. 14, an exemplary relationship generation tool 550 is shown. As discussed above, the relationship generation too may be used to analyze the information in the knowledge model 140 and populate various relationship tables. In the embodiment of FIG. 14, the relationship generation tool 550 includes three components. The field-to-text relationship tool 1410 generates the field-to-text relationships, as described above. In one embodiment, the field-to-text relationship tool 1410 reads each name field from every entity table. For each name field, the field-to-text relationship tool 1410 executes a stored procedure that searches for the given name in various other fields of the entity tables. For example and with reference to FIGS. 2A and 2C, the field-to-text relationship tool 1410 may select the name field from person entity table and search for that entry in the title and abstract fields of the literature entity table. If a match is found, a field-to-text relationship may be added to the field-to-text relationship table. Alternatively, or in addition to, the field-to-text relationship tool 1410 may retrieve the full text of the article referenced by the literature table (even though the article is not necessarily stored in the knowledge model 140) and perform a similar search. It should be apparent to one of ordinary skill in the art that the field-to-text relationship tool 1410 may be configured to select any set of fields from the entity tables and search any other fields in the entity tables. Additionally, the field-to-text relationship tool 1410 may be configured to search the text of unstructured data that is not referenced in any entity in the knowledge model.

The relationship generation tool 550 may also be configured to derive relationships by analyzing the data of the knowledge model 140. These types of relationships are referred to herein as derived relationships. In one embodiment, the relationship generation tool may include a transitive relationship tool 1420. The transitive relationship tool 1420 determines transitive relationships. As used herein, a transitive relationship is defined as any relationship between two entities that is based on at least two separate relationships. As discussed above, a direct relationship is a relationship that has been determined from information in a data source 110. These direct relationships may be stored in a direct relationship table. In one embodiment, the transitive relationship tool 1420 selects each row in the direct relationship table. For each field referred to in the relationship definition, the transitive relationship tool 1420 may search every other row in the direct relationship table for a match. If a match is found, a new relationship is created to reflect the commonality. For example, if a direct relationship is defined between field A and field B, the transitive relationship tool 1420 may search the other rows of the direct relationship table for a match on field A. If a match is found, for example, relating field A to field C, the transitive relationship tool 1420 may create a transitive relationship relating field B to field C. This is an example of a single hop transitive relationship. Preferably, the transitive relationship tool 1420 uses a search depth algorithm to calculate the transitive relationships across n hops. In one embodiment, the transitive relationship may be stored in a transitive relationship table. Alternatively, the transitive relationship may be stored in the same table as the direct relationships. In one embodiment, the transitive relationship definition includes information detailing each hop from the two related entities.

The relationship generation tool 550 may also include a proximity relationship tool 1430. Similar to the field-to-text relationship tool 1410, the proximity relationship tool 1430 searched the text of either fields in the knowledge model 140 or unstructured files, such as articles. The proximity relationship tool 1430 creates a proximity relationship if two entities appear in the same text. In one embodiment, indexes are created for all the text to be searched (i.e. specific field values or unstructured data items). The indexes are then used to determine if two entities appear in the same text. Alternatively, or in addition to, the proximity relationship tool 1430 may be configured to generate a proximity relationship if the entities appear within a given proximity of each other in the text, for example, within n words of each other. Other criteria, such as each field appearing at multiple instances within each document, each field appearing in the same sentence, and the like, may also be used to define a proximity relationship. It should be apparent to one of ordinary skill in the art that the determination of a proximity relationship may be dependent on the type of file being examined. For example, if a text file is be used, a proximity relationship may be generated if the words fields appear within the same paragraph. If, however, the file being searched is a spreadsheet, the proximity relationship tool 1430 may generate a proximity relationship if the two fields appear in same cell, row, or column. In one embodiment, the proximity relationship tool 1430 stores the proximity relationship definition as well as information detailing the rationale behind the generation of the relationship. For example, to define a proximity relationship between two fields, the proximity relationship tool 1430 may store each field, the criteria used to determine the relationship, and the article or reference in which the use of the fields met the given criteria.

Referring to FIGS. 15-26, an exemplary navigator tool 170 is shown. In the embodiment of FIGS. 15-26, the navigator tool 170 is a graphical user interface that allows the user to select a record or item from one of a table of the knowledge model 140 and, in response to the selection, display a set of related items or records. Preferably, and only registered users may access the knowledge model 140. It should be apparent to one of ordinary skill in the art that other implementations of the navigator tool 170 are contemplated herein. In one embodiment, the user may be initially directed to a log in to the navigator tool 170 in order to access the data stored in the knowledge model 140. To do so, the user may enter a valid username and password combination. The user may then submit this information to be validated against a database of user information, for example, the user information database 145. Optionally, the user may be allowed to select an option to store the username and password information for future log in attempts.

In the embodiment of FIGS. 15-26, the navigator tool 170 includes a toolbar 1510 and a navigation area 1520. The toolbar 1510 may provide access to a variety of functions of the navigator tool 170 via corresponding interface objects, such as a navigation functions. The toolbar and various capabilities accessible via the toolbar are described in more detail below in reference to FIGS. 19-26. In one embodiment, the navigation area 1520 includes nine visually separated panels 1530. Each panel 1530 contains information corresponding to an entity of the knowledge model 140. The information contained in each panel may be referred to as an Item. The Item in the center, or active, panel 1530 may display a single Item. Each of the remaining panels 1530 may display zero, one or more Items for a particular entity table of the knowledge model 140 that relate to the Item in active panel 1530.

Figure 16:
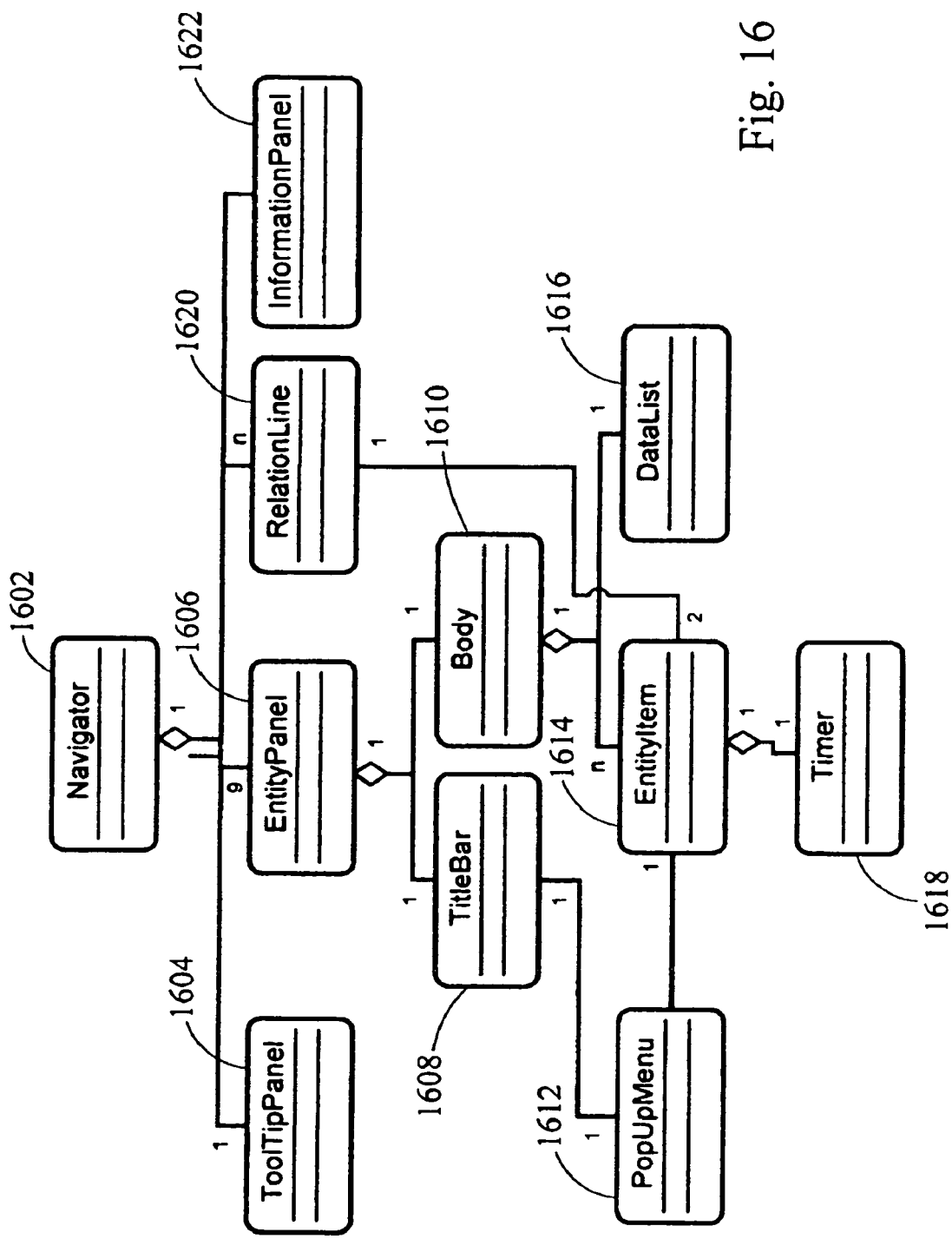
FIG. 16 is a diagram of exemplary components of a navigator tool in accordance with an embodiment of the present invention.
Figure 17:
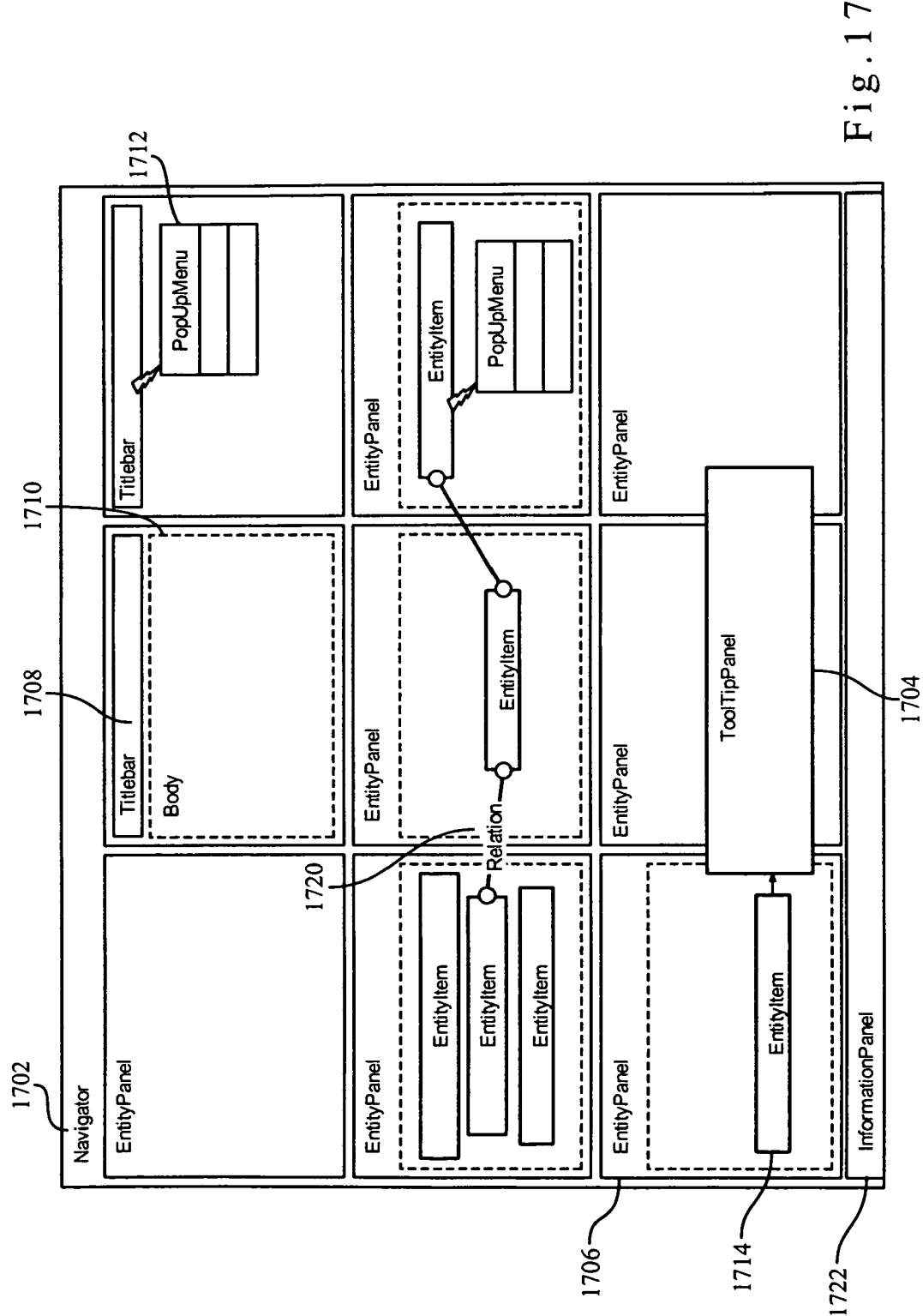
FIG. 17 is an exemplary layout for a navigation tool in accordance with an embodiment of the present invention.

Referring now to FIGS. 16 and 17, a diagram of exemplary components and an exemplary layout for one embodiment of a navigation tool 170 are shown, respectively. The Navigator component 1602, 1702 is the main component that will contain the rest of the components and manage the interface among all the other components of the navigator tool 170. In one embodiment, each Navigator component 1602, 1702 comprises a ToolTipPanel component 1604, 1704, one to nine EntityPanel components 1606, 1706, one or more RelationLine components 1620, 1720, and an Information Panel component 1622, 1722.

The ToolTipPanel component 1604, 1704 may include summary and supporting attribute information about an Item. In one embodiment, ToolTipPanel components 1604, 1704 are implemented as pop-up boxes that appear when a user mouses-over an Item. For example, a ToolTipPanel component 1604, 1704 for an Item describing a person might contain their age, level within their company, hire date, email address, and the like. In one embodiment, the ToolTipPanel component 1604, 1704 associated with the active Item may be permanently displayed below the Item name.

The EntityPanel component 1606, 1706 includes information corresponding to an entity of the knowledge model 140. In the embodiment of FIGS. 16 and 17, each EntityPanel component 1606, 1706 consists of a TitleBar component 1608, 1708 and a body component 1610, 1710. The TitleBar component 1608, 1708 may include information about the entity, such as an entity name, icon for the entity. The Body component 1610, 1710 may include information about the Items in an entity table. In one embodiment, the Body component 1610, 1710 includes one or more EntityItem components 1614 and a DataList component 1616. Each EntityItem component 1614, 1712 includes information for an item being displayed in the EntityPanel component 1606, 1706. Optionally, the TitleBar component 1608, 1708 may include node counter information that shows how many Items from the particular entity table are related to the Item in the active panel 1606, 1706 as well as which items are currently visible. In one embodiment, both the EntityItem components 1614, 1714 and TitleBar components 1608, 1708 may be associated with a PopUpMenu components 1612, 1712 which provide access to various functions associated with the EntityItem components 1614, 1714 and TitleBar components 1612, 1712, respectively.

Referring now to FIG. 18A-D, an exemplary screen shot of a navigator tool 170 is shown. The navigator tool 170 may include a toolbar 1810 and a navigator component 1820. In the embodiment of FIG. 18, the navigator component 1820 includes the elements described above in regard to FIGS. 16 and 17. As shown, the navigator component 1820 includes nine entity components 1830, each including a title component 1834 and a body component 1836. The title component 1834 includes the name of an entity table and, where applicable, a node counter that displays the total number of items 1840 included in the corresponding entity components 1830.

As described above, the navigator tool 170 may be implemented as a graphical user interface that allows the user to select a record or item from one of a table of the knowledge model 140 and, in response to the selection, display a set of related items or records. In the embodiment of FIG. 18 the center entity component 1832 represents the active or selected node 1838 and includes the name of the active node 1838. In one embodiment, the name of active node 1838 may be truncated. Optionally, the navigator tool 170 may be configured to display a pop-up window displaying various information about the active item 1838 upon a predetermined event, such as an activation of the item 1838 via a single-click, double-click, mouse-over, and the like. Optionally, the same functionality may be provided for the related nodes 1840.

The remaining entity components 1832 may be used to display those related items 1840 in the knowledge model 140 related to the active node 1838, for example, by displaying the name of the related item 1840. Optionally, indicia of the link type associating each related item 1840 to the active node 1838 may be included. In the embodiment of FIG. 18, a roman numeral indicating the type of link is used to indicate the link type. For example, direct, or field-to-field, links may be designated by the roman numeral "I", field-to-text links by the roman numeral "II", transitive links by the roman numeral "III," and proximity links by the roman numeral "IV." Other exemplary indicia may include using associated font colors, font sizes, or any other visual indicator. In one embodiment, the navigator tool 170 may query the knowledge model 140 to determine the related items 1840 in response to the selection of the active node 1838. Preferably, queries are performed via a batch process that determines all related items 1840 for each item 1830 of the knowledge model. The queries may be saved, for example in a database table, to vastly improve the performance of the navigator tool 170.

Each entity component 1832 is associated with a particular table of the knowledge model 140. In one embodiment, each entity component 1832 displays all the related items 1840 for the associated table of the knowledge model 140. Preferably, the user will be allowed to select the type of entity being displayed in any particular entity component 1832 by associating that entity component 1832 to any table in the knowledge model 140. In such an embodiment, the user may configure the entity components 1832 to display the tables of interest to that particular user. Preferably, the associations of entity components to knowledge model 140 tables may be stored.

In one embodiment, each entity component 1832 may be configured to display a set number of item 1840 at a given time. In such an embodiment, navigation tools, such as a scroll bar or navigation arrows, may be provided to allow the user to access the entire list of related items 1840. Additionally, the entity component 1832 may include node 1840 count information to inform the user of the additional though not visible items 1840. Preferably, the entity component 1832 also includes information describing which related items 1840 of the set are currently being displayed. For example, the entity component 1832 may show that items 1840 three through nine of eighty-six total items 1840 are currently being displayed. In such an embodiment, a scrollbar or other user-interface control may be included to provide access to the items 1840 not being displayed.

Figure 18A:
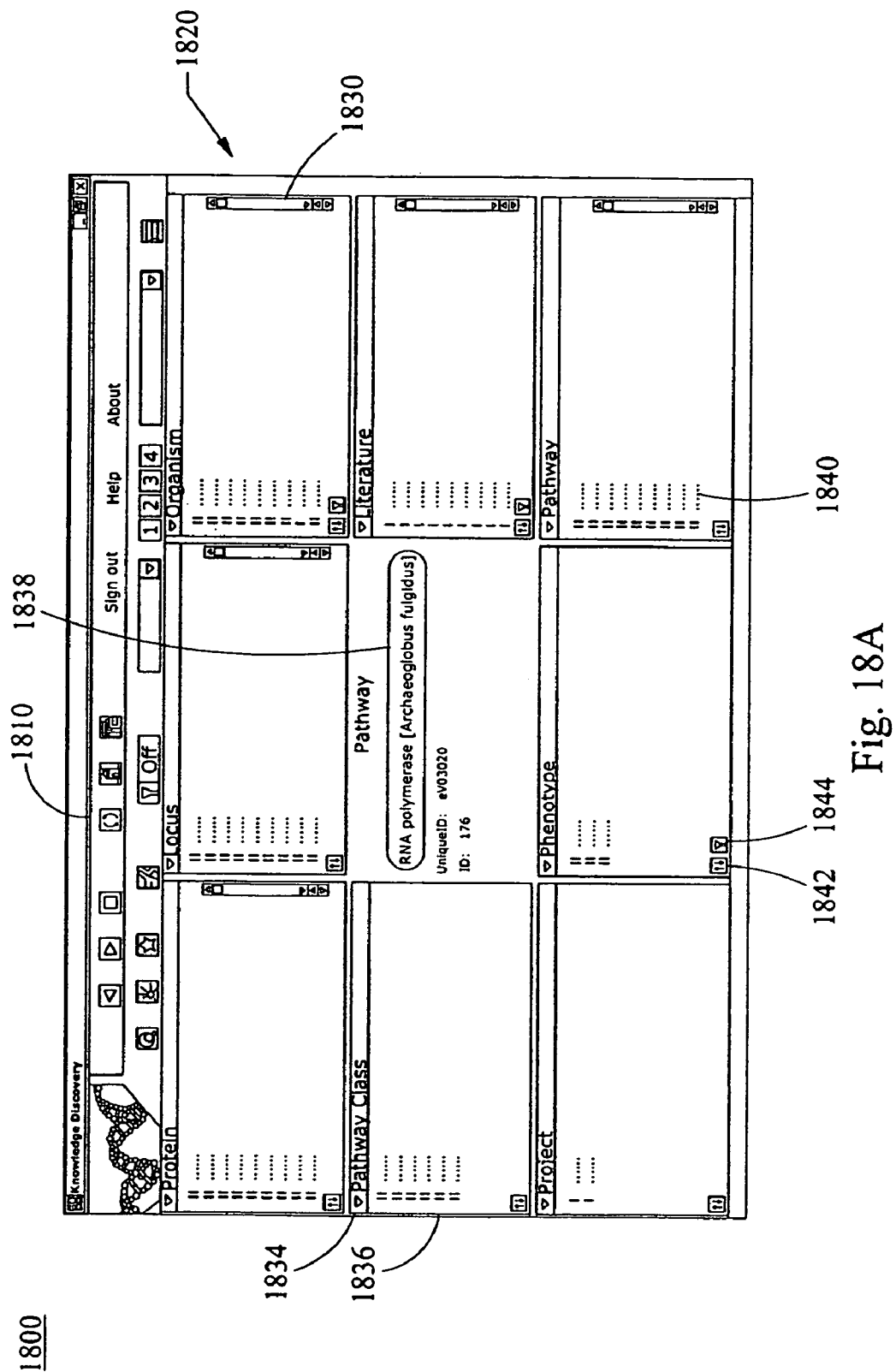
FIGS. 18A-E are exemplary screen shots of a navigator tool in accordance with an embodiment of the present invention.

Optionally, the entity component 1832 may include tools to manipulate the related items 1840 contained therein. In the embodiment of FIG. 18A, each entity component includes a sort button 1842. The user may activate the sort button 1842 to sort the list of related items 1840 alphabetically or by confidence level. Other criteria such as date restrictions and the like may also be used to sort the related items 1840. The entity component may also include a filters button 1844 which opens the master filters dialog for the corresponding entity, described in more detail below in reference to FIGS. 26A-E.

Figure 18B:
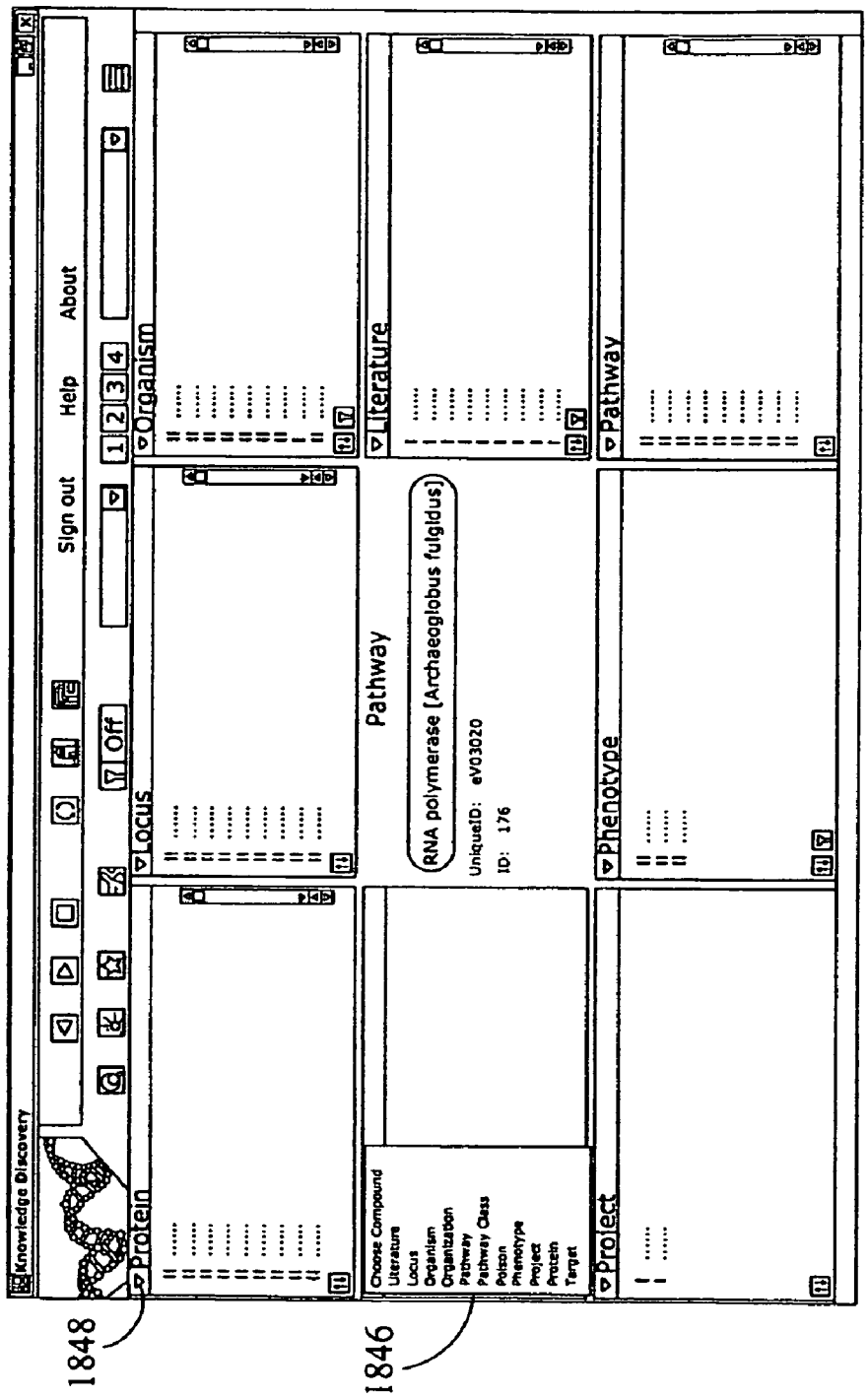

As described above, each entity component 1832 may be associated with an entity type of the knowledge model 140. In one embodiment, the user may change the entity table associated with any entity component 1832 that displays related items 1840. As shown in FIG. 18B, the user may activate a menu, that includes a list of all possible entity tables of the knowledge model 140 that may be associated with the particular entity component 1832. This menu may be activated, for example, by selecting the appropriate triangle icon 1848 on the title component 1834. Other methods of changing the associations between an entity components 1832 and entity tables of the knowledge model 140 are contemplated herein.

Figure 18C:
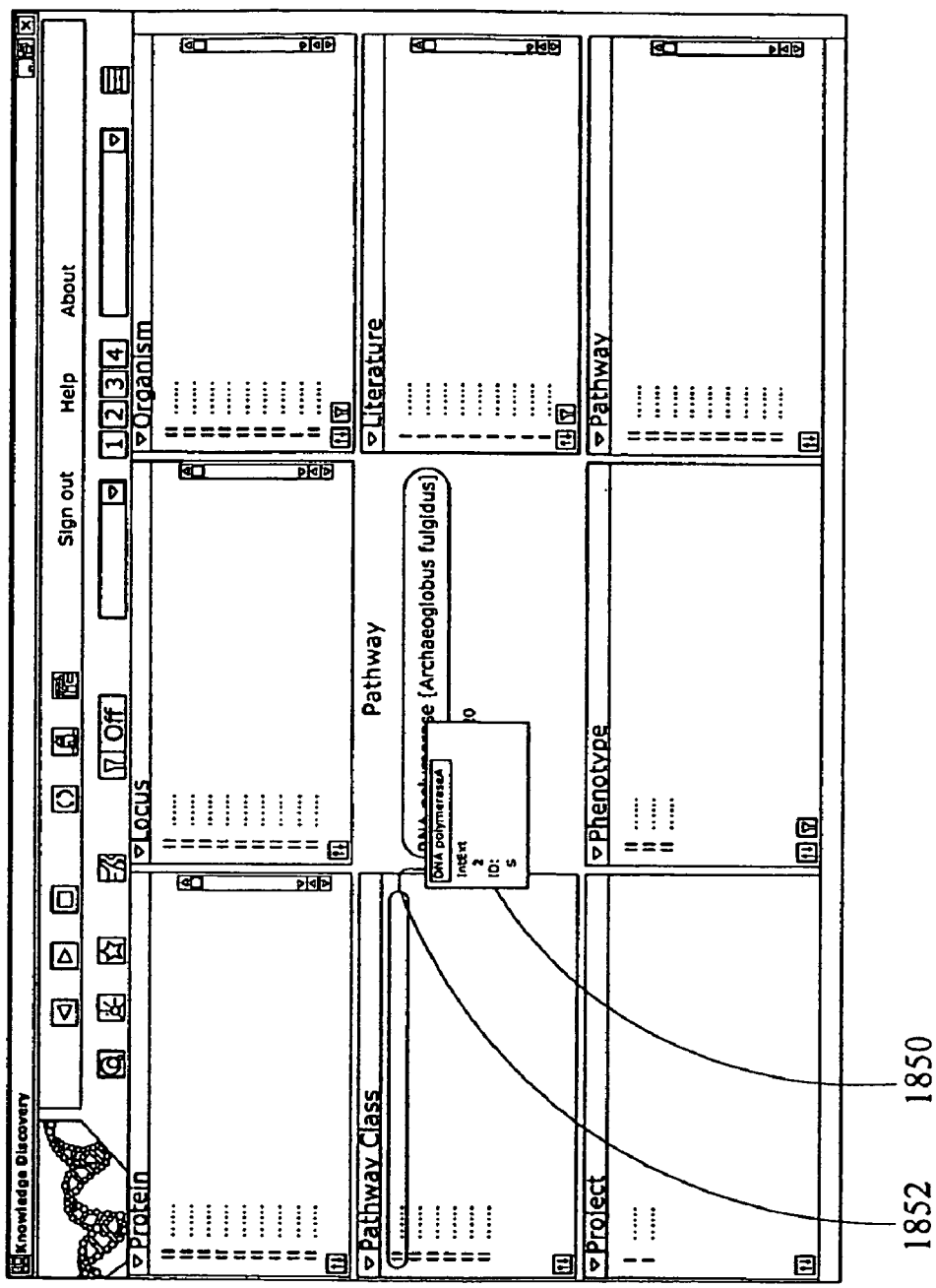

In one embodiment, the activation of a particular related item 1840 may cause additional information about that item 1840 and its relationship to the active item 1838 to be displayed. As shown in FIG. 18C, the selection of a related item 1840 may cause a ToolTipPanel component 1850 to be displayed that shows summary information for the related item 1840.

Additionally, or alternatively, a relationship line 1852 between the related item 1840 and the active item 1838 may also be displayed upon activation of the related item 1840. In the embodiment of FIG. 18C, the color and style of the relationship line 1852 indicates the type of relationship between the two items. For example, a continuous green line may indicate a field-to-field link, a dashed blue line may indicate a field-to-text link, a dashed and dotted yellow line may indicate a transitive relationship, and a dotted red line may indicate a proximity relationship. It should be readily apparent to one of ordinary skill in the art that the relationship type may be indicated using color, style, size, and the like, or any combination therein.

Figure 18D:
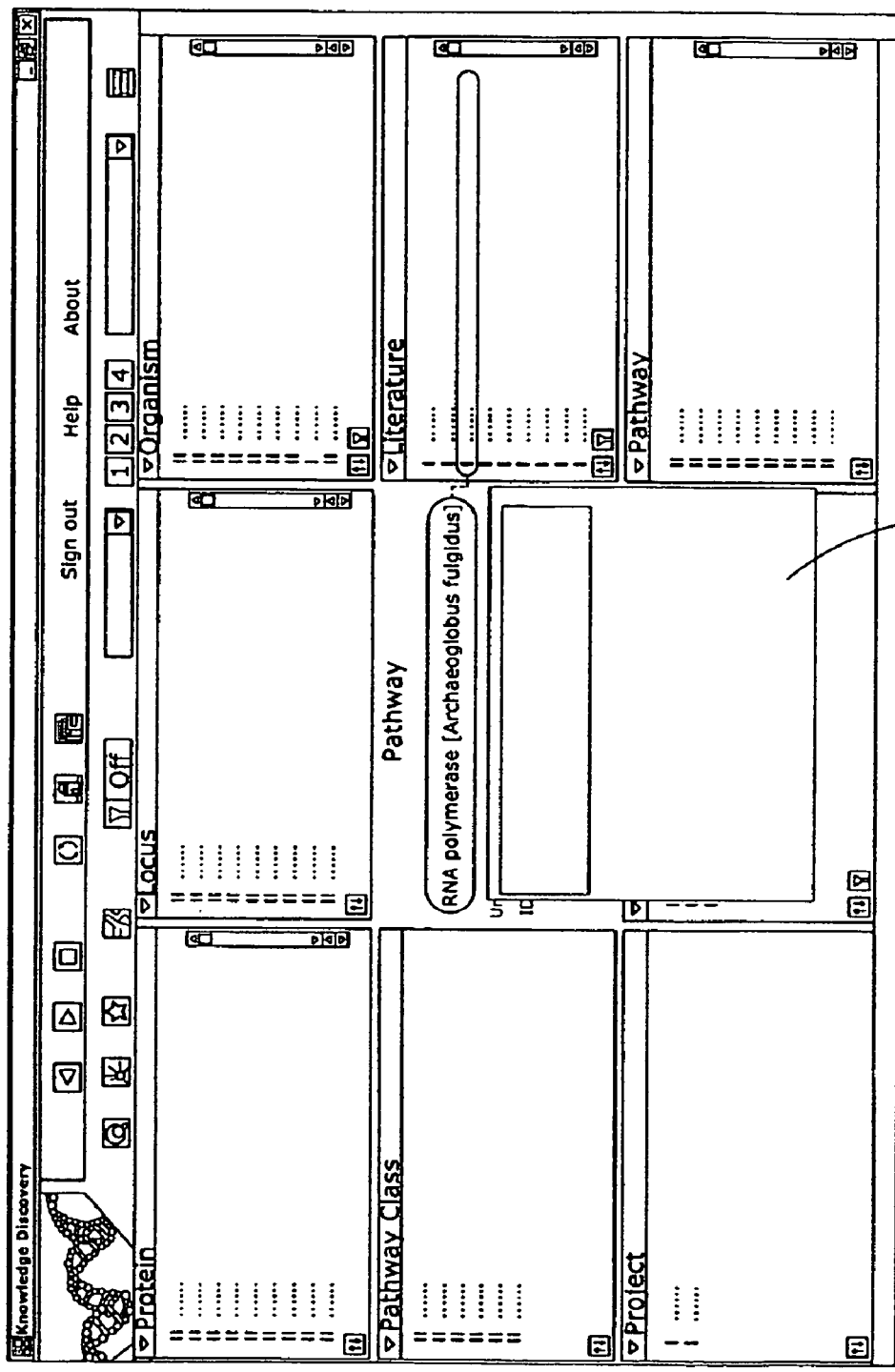

As shown in FIG. 18D, the user may select any of the related items 1840 to make that item the active node 1838. In response, the navigator tool 170 may update the display accordingly. In one embodiment, the navigator tool 170 may submit a new query or retrieve saved queries from the knowledge model 140 and display the related items 1840 to the new active item 1838. Alternatively, or in addition to, the user may drag-and-drop a related item into the center entity panel to make that item the active item 1838.

Figure 18E:
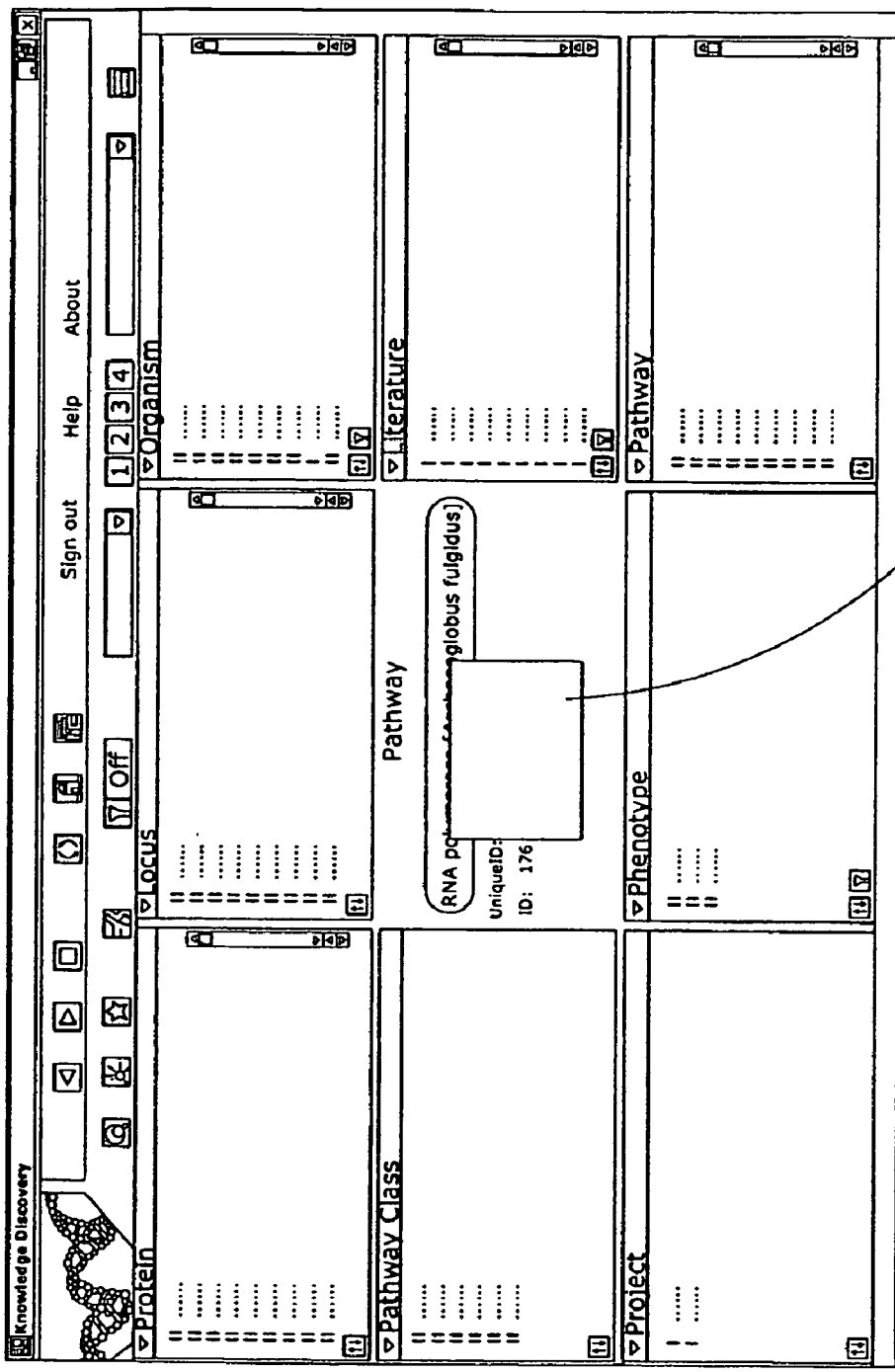

As shown in FIG. 18E, the user may access a variety of item-related options via a pop-up menu 1854, for example, by right clicking on an item. In one embodiment, the pop-up menu 1852 provides access to functions create a bookmark to an item, make an item the home item, email a link to an item, monitor an item, and show link evidence for a related item 1840. A bookmark is a link to a particular item. Bookmarks are stored in a list of bookmarks accessible via the bookmark button of the navigator toolbar 1810, described in more detail below. The home item is a special bookmark that can be loaded into the navigator tool by pressing the home button of the navigator toolbar 1810. Items may be emailed to an individual by selecting the email link option. In one embodiment, selecting the email link option launches the default mail program, creates a new e-mail with a system generated introduction, and places the link to the item into the new e-mail message. Additionally, the user may select an item to monitor via the pop-up menu. As described in more detail below, the system 100 may monitor items and notify the user of updates and/or changes to the items. When a user denotes an item to monitor, a date stamp may be created and saved with item information to be used by the system 100 for monitoring.

Finally, the user may wish to see information on why a particular related item 1840 is considered related to the active node 1838. To do so, the user may select the show link evidence option from the pop-up menu 1854. Depending on the type of link establishing a connection between the active node 1838 and the related node 1840, different link information may be shown. For example, link information for field-to-field links may include the data source from which the link was extracted. Link information for field-to-text links may include a short part or clip of the literature text that surrounds the keyword. In one embodiment, the clip length should user configurable. Preferably, the clip length may be initially set to be N words total, such that (N−1)/2 words preceding the item keyword and (N−1)/2 words following the item keyword are included. For example, if the clip is set to 31 words, the clip may include the 15 words preceding and following the item keyword. For transitive links, the link information may include each field-to-field link information for each hop included in the link. Finally, link information for proximity links may include the title of the article which mentions both items, as well as a clip for showing each item in context.

Figure 19:
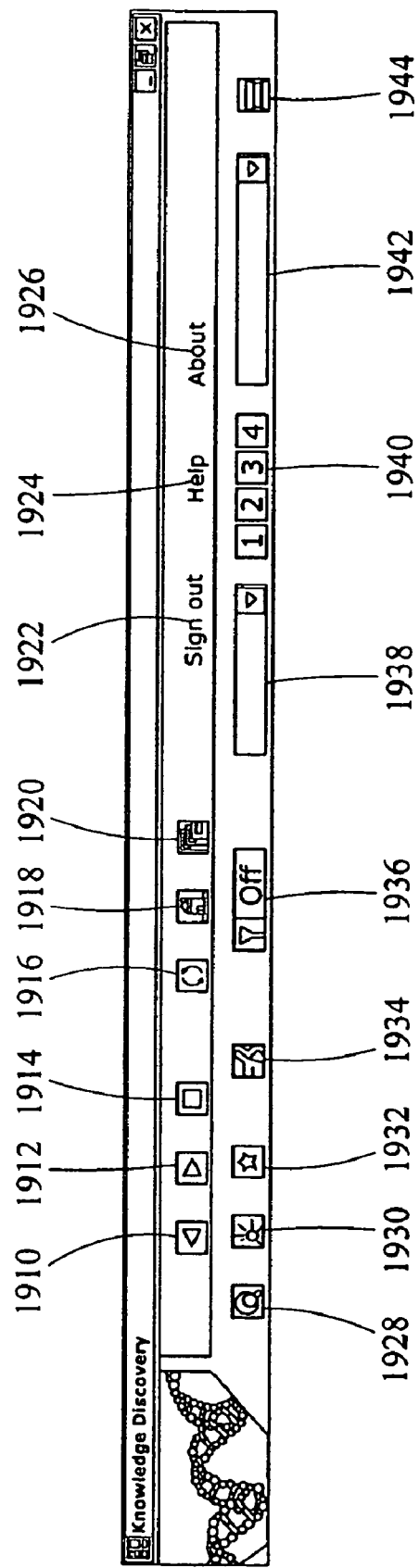
FIG. 19 is an exemplary screen shot of a navigation toolbar in accordance with an embodiment of the present invention.

As described above, the navigator tool 170 may include a navigation toolbar 1810. One embodiment of the navigation toolbar 1810 is shown in FIG. 19. The navigation toolbar 1510 may contain icons and controls which enable the user to access and configure the various services of the navigator tool 170. In one embodiment, the navigation toolbar 1510 may include a back button 1910, a forward button 1912, a stop button 1914, a refresh button 1916, a home button 1918, a history button 1920, a signoff button 1922, a help button 1924, an about button 1926, a search button 1928, a wizards button 1930, a bookmarks button 1932, a monitored items button 1934, a filters button 1936, a source filters drop-down list 1936, a confidence level tool 1940, a context drop down list 1942, and an options button 1944. It should be apparent to one of ordinary skill in the art that the various user interface components may be used provide access to the functions described below.

The navigation tool 170 provides basic navigational functions via the navigation buttons. For example, the back button 1910 and forward button 1912 may be provided to allow the user to step through their recent navigation history backwards and forwardly, respectively. Activating the stop button 1914 may cancel the submission of a query to the knowledge model 140. In one embodiment, a command is issued to the knowledge model 140 to abort query processing. Preferably, all current client and server processing activity is stopped. Activating the refresh button 1916 may allow the user to manually refresh their current view (for example, by resending a query to the knowledge model 140) and update the display of related item 1840 based on the new results. A home button 1918 may be provided that takes the user to their home view (i.e. home item). The home view is a set node. The home view may be user customizable.

Figure 20:
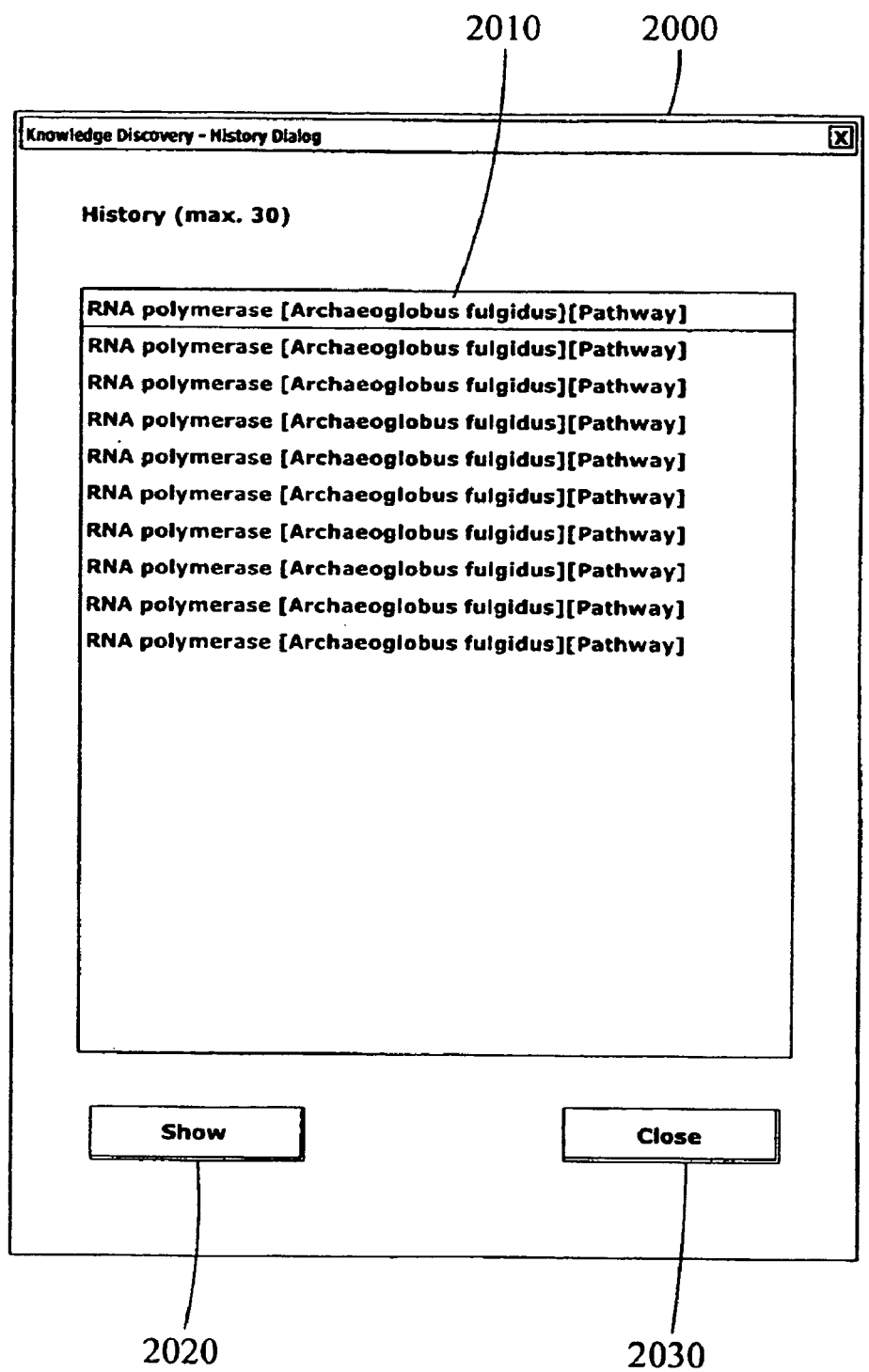
FIG. 20 is an exemplary screen shot of a history dialogue window in accordance with an embodiment of the present invention.

A history dialog button 1920 may also be provided to launch a history dialog window. One embodiment of a history dialogue window is shown in FIG. 20. The dialog window 2000 may show the user's recent navigation history, such as a list of navigation events 2010. In one embodiment, both the node name and entity name are displayed. The user may be able to highlight a navigation event and click a "show" button 2020 to refocus the navigator 170 on that item by making that item the active node 1838. Alternatively, or in addition to, the user may be able to double-click on a history item and refocus the navigator on that item. The user may close the history dialogue window 2000 by selecting the close button 2030. In one embodiment, the navigator tool 170 may save a set number of history events. This number may be user-configurable. Preferably, the history events may be stored in the user information database 145 to make the history events session independent and persistent.

Upon selection of the signoff button 1922, the user may be logged out of the navigator tool 170. Upon selection of the help button 1924, the user may be provided access to a help system, as known in the art. In one embodiment, selection of the help button 1924 may cause an html based help system to be launched in a separate window. A window containing information about the knowledge discovery tool 100 or navigator tool 170 may be opened upon selection of the about button 1926. This information may include version information, such as a revision number, intellectual property information, such as copyright, patent and/or licensing information, and the like.

Figure 21:
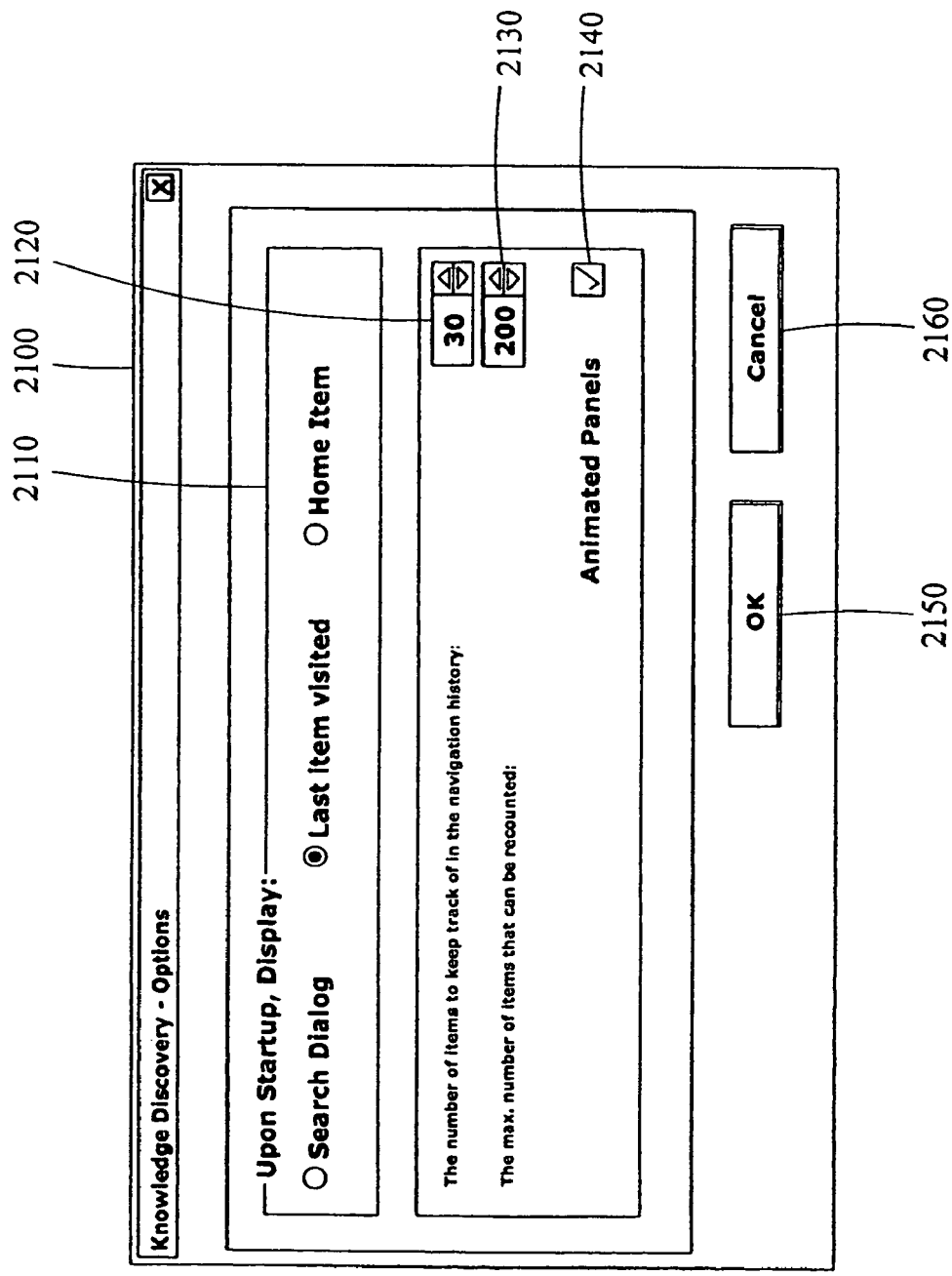
FIG. 21 is an exemplary screen shot of a master options dialog in accordance with an embodiment of the present invention.

The options button 1944 may launch the master options dialog. One embodiment of the master options dialog 2100 is shown in FIG. 21. In the embodiment of FIG. 21, the master preferences dialog 2100 includes a startup view preference 2110, a navigation history preference 2120, a related items limit preference 2130, an animations preference 2140, a reset button (not shown), an ok button 2150, and a cancel button 2160.

The startup view preference 2110 allows the user to select what they want to see upon starting the navigator tool 170. In one embodiment, three options are provided: search, last item visited and home item. If the search option is selected, the navigator tools 170 opens with a search dialog, discussed below in more detail. If the last item visited option is selected, the navigator tool 170 opens with the active node 1838 from when the navigator was last closed. In one embodiment, all filter, confidence, and entity component 1832 association settings may also be preserved. Filter and confidence settings are described in more detail below. Finally, if the home item option is selected, the navigator tool 170 will open with the home item as the active node 1838. Preferably, the home item startup option is the default option and the home view is set to a standard node.

The navigation history preference 2120 defines the number of navigation events stored for the navigation session. In one embodiment, the default value is set to 10. Alternatively, or in addition to, the navigation history preference 2120 may have a maximum value, for example, 30 events. Preferably, the navigation history preference 2120 is implemented as a drop down box.

The related items limit preference 2130 controls the number of records which can be returned to each entity panel 1932 in the navigator tool 170 from a query. In one embodiment, a default value is selected to optimally balance performance and quality of the results returned.

The animations preference 2140 may allow the user to enable or disable animation rendering effects in the user interface. Preferably, the animations preference 2140 is implemented as a checkbox and is selected by default. An ok button 2150 may be provided to accept the currently selected preferences, and a cancel button 2160 may be provided to close the dialog 2100 without changing preferences.

Figure 22:
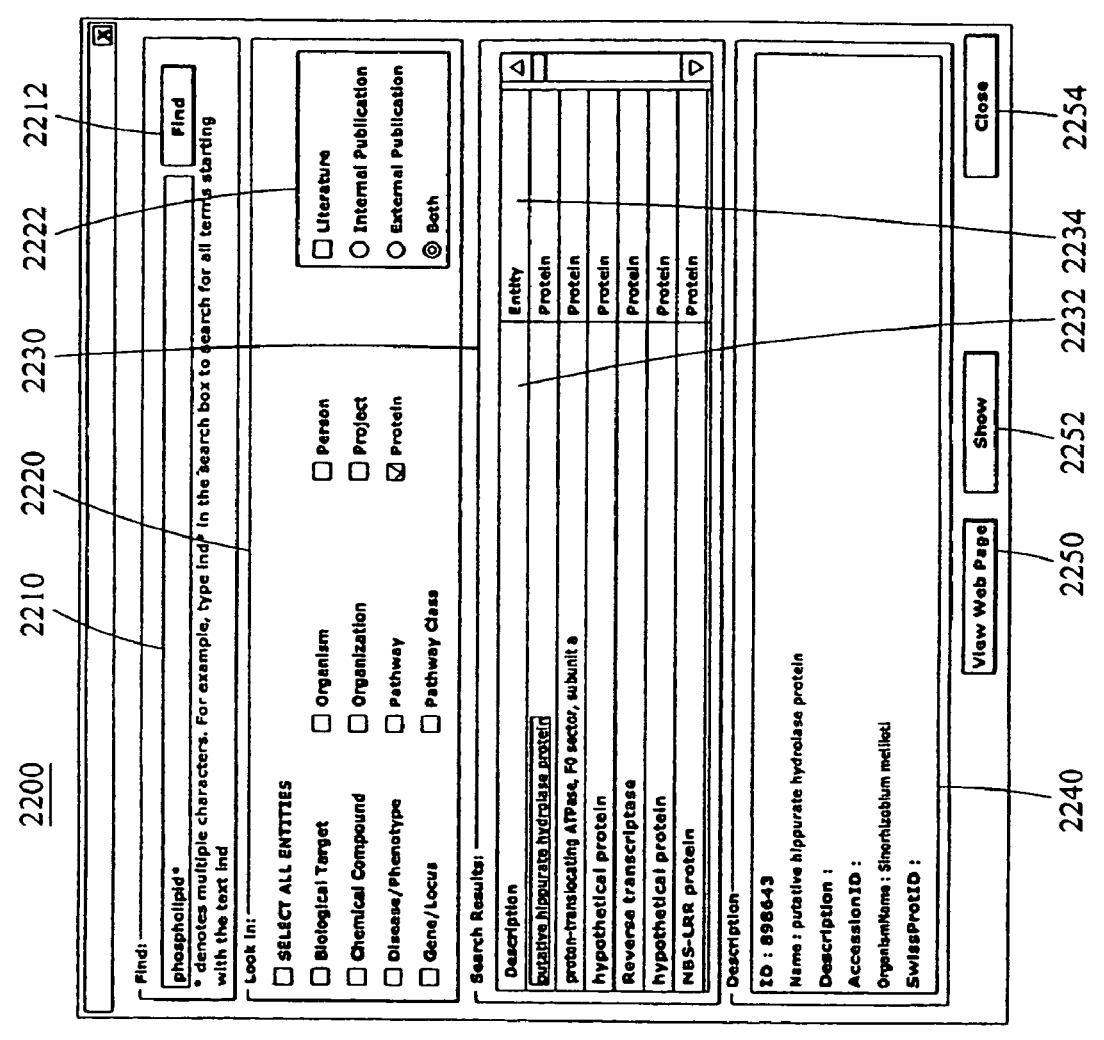

Referring again to FIG. 19, the search button 1928 may launch a search tool that allows the user to perform a keyword search of the knowledge model 140. The search dialog may include the appropriate user interface tools to allow the user to specify a search term(s) for querying the knowledge model 140. One embodiment of a search tool 2200 is shown in FIG. 22. To perform a search, a user may enter one or more keywords of interest in the search term field 2210. The search will perform a literal search for the entered search terms. In one embodiment, a '*' character acts as a wildcard identifier and denotes multiple characters. For example, a search for the keyword "ind*" may cause the knowledge model 140 to search for all terms starting with the text "ind." The user may also be able to select the type of information they are looking for by checking an entity type from those listed in the menu 2220 of checkboxes below the search field 2210. For example, one may restrict the results of a search to diseases, genes or literature by selecting the appropriate items in the menu. In one embodiment, the user may further refine a search target by selecting "Internal, External, or Both" under the literature entity. Preferably, the navigator tool 170 searches against all entities by default.

To begin a search, the user may click the find button 2212. In response, the system 100 performs a free-text search against the information stored in the knowledge model 140. When the search is complete, the results are shown in the Search Results field 2230. In one embodiment, the search results include a description 2232 of the item and the entity table 2234 to which it belongs. The user may also be able to view more detailed information in the description field 2240 by selecting the item from the list. In one embodiment, the selection of an item is made via a single click on any of the search results. The results may be sorted by name or by type by clicking on the header of the appropriate fields 2232 and 2234. The user may be able to view the source of a particular search result by clicking the View Web Page button 2250. The Show button 2252 shows the selected item in the navigation window, making it the active node 1838. Alternatively, or in addition to, the user may double-click a particular search result to make that item the active item 1838. The Close button 2254 will close the search dialog box.

Figure 23A:
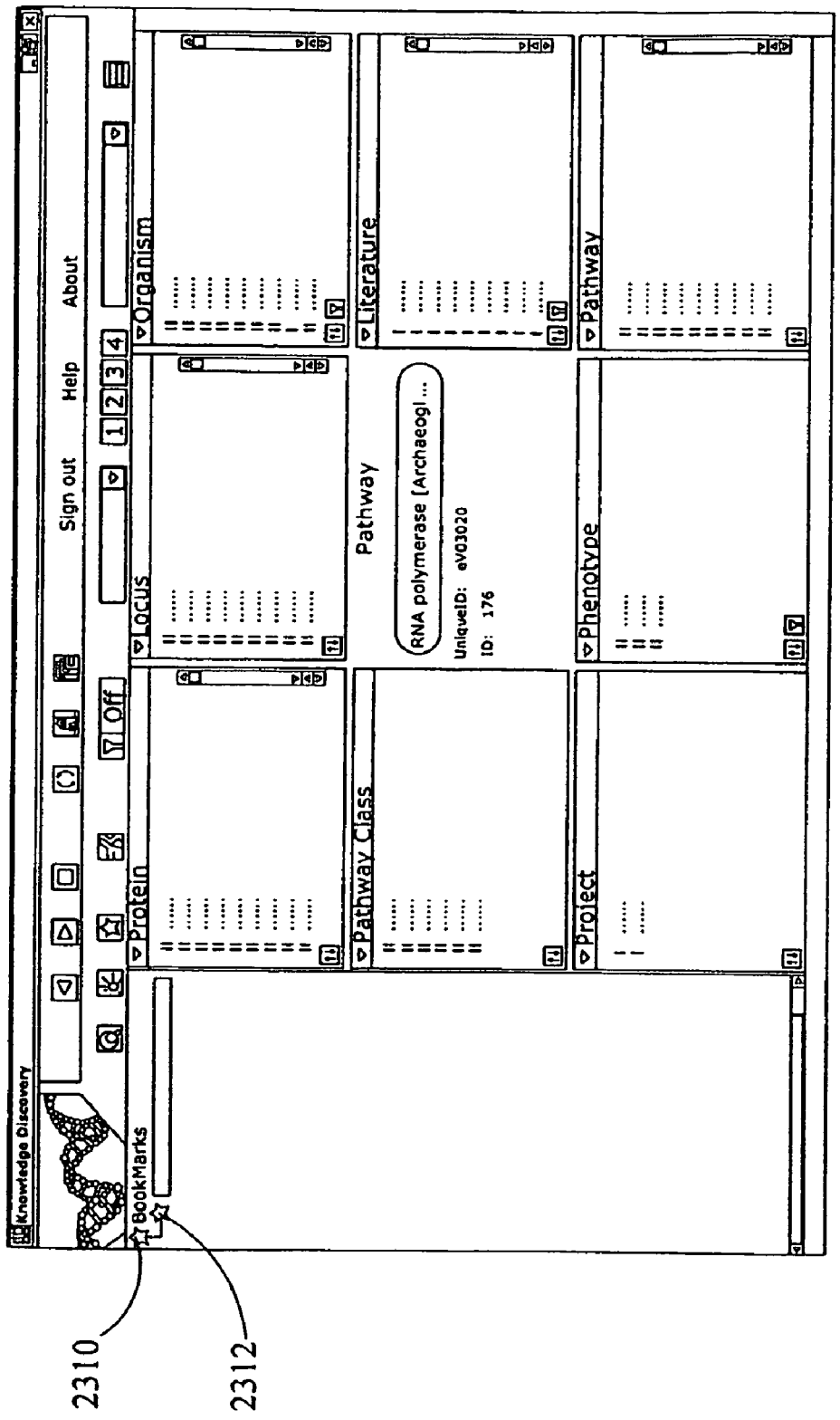
FIG. 23A-B are exemplary screen shots of a navigator with a bookmark list in accordance with an embodiment of the present invention.

Referring again to FIG. 19, a bookmarks button 1930 may also be provided on the navigator toolbar 1510. As described above, bookmarking an item allows the user to save links to previously viewed items to enable their quick retrieval later. Clicking the Bookmark button 1930 may cause a list of saved bookmarks to be displayed. An exemplary screen shot of the navigator tool 170 with a bookmark list 2310 is shown in FIG. 23A. As shown, the bookmark list 2310 includes a list of bookmarks 2312. Selection of a bookmark 2312 may cause the item that is bookmarked to become the active item 1838 of the navigator tool 170. In one embodiment, bookmarks 2312 include a name. When a bookmark 2312 is created, the bookmark 2312 may have the same name as the item that is being bookmarked. Optionally, the user may rename the bookmark 2312, for example, by clicking the right mouse button over the bookmark 2312 and selecting "Rename" from a popup menu and typing the new name. Bookmarks 2312 may also be deleted from the list, for example, by clicking the right mouse button over the bookmark and selecting "Delete" from a popup menu.

Optionally, bookmarks 2312 may be organized into folders much like computer files or internet bookmarks are managed. In one embodiment, the user may create a folder by clicking the right mouse button over the folder under which you want to create your new folder and selecting a "Create folder" option from a popup menu. Folders may also be renamed using a similar procedure as renaming bookmarks 2312 described above. A folder may also be deleted in a similar manner. Once a folder has been created, the user may organize bookmarks 2312 by dragging the bookmark 2312 (i.e., hold the left mouse button over the bookmark and move your mouse) to the folder. Folders may also be hierarchically arranged in a similar manner. In one embodiment, clicking a folder will alternatively show or hide the contents of that folder.

Figure 23B:
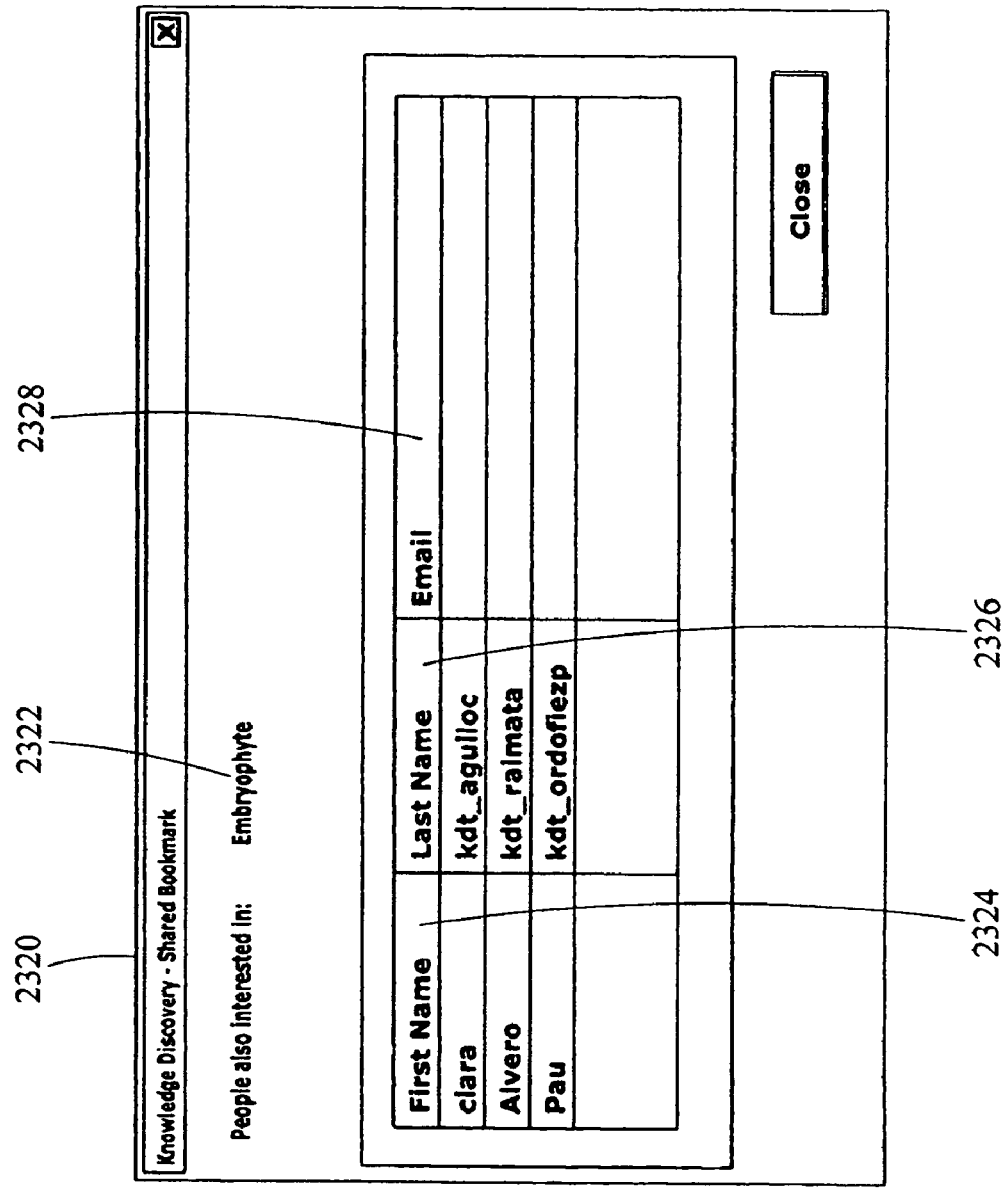

Optionally, bookmarks 2312 may be shared among users. In one embodiment, the system 100 may notify users of a common interest in particular item if one or more colleagues have the same bookmark 2312 by creating a special bookmark that is added to each users list 2310. Selection of this special bookmark may open a shared bookmarks tool. One embodiment of a shared bookmarks tool 2320 is shown in FIG. 23B. The shared bookmark tool includes information about the subject item 2322, such as an item name, as well as information about each user sharing the interest. In one embodiment, each users' first name 2324, last name 2326, and email address 2326 are displayed. It should be apparent to one of ordinary skill in the art that other information may be displayed. Optionally, the user may elect not to share a bookmark with colleagues. Alternatively, or in addition to, users may be notified of common bookmarks by other methods, such as via email, instant messages, pop-up windows, and the like.

Referring again to FIG. 19, a wizards button 1930 may be provided to allow the user to launch a wizard service. In one embodiment, the wizard service may guide the user through a series of screens to formulate a search. For example, the wizard service may assist with the process of identifying existing assets that have indication in a specified area. An exemplary area may be a particular disease. Exemplary assets may be compounds into which research efforts have been invested. For a knowledge model 140 for pharmaceutical research, the wizard may take user selected diseases and targets as inputs, allow the user to also specify genes, proteins, or pathways, and then and return a list of possibly relevant projects, literature and compounds, as related by the knowledge model 140.

Figure 24A:
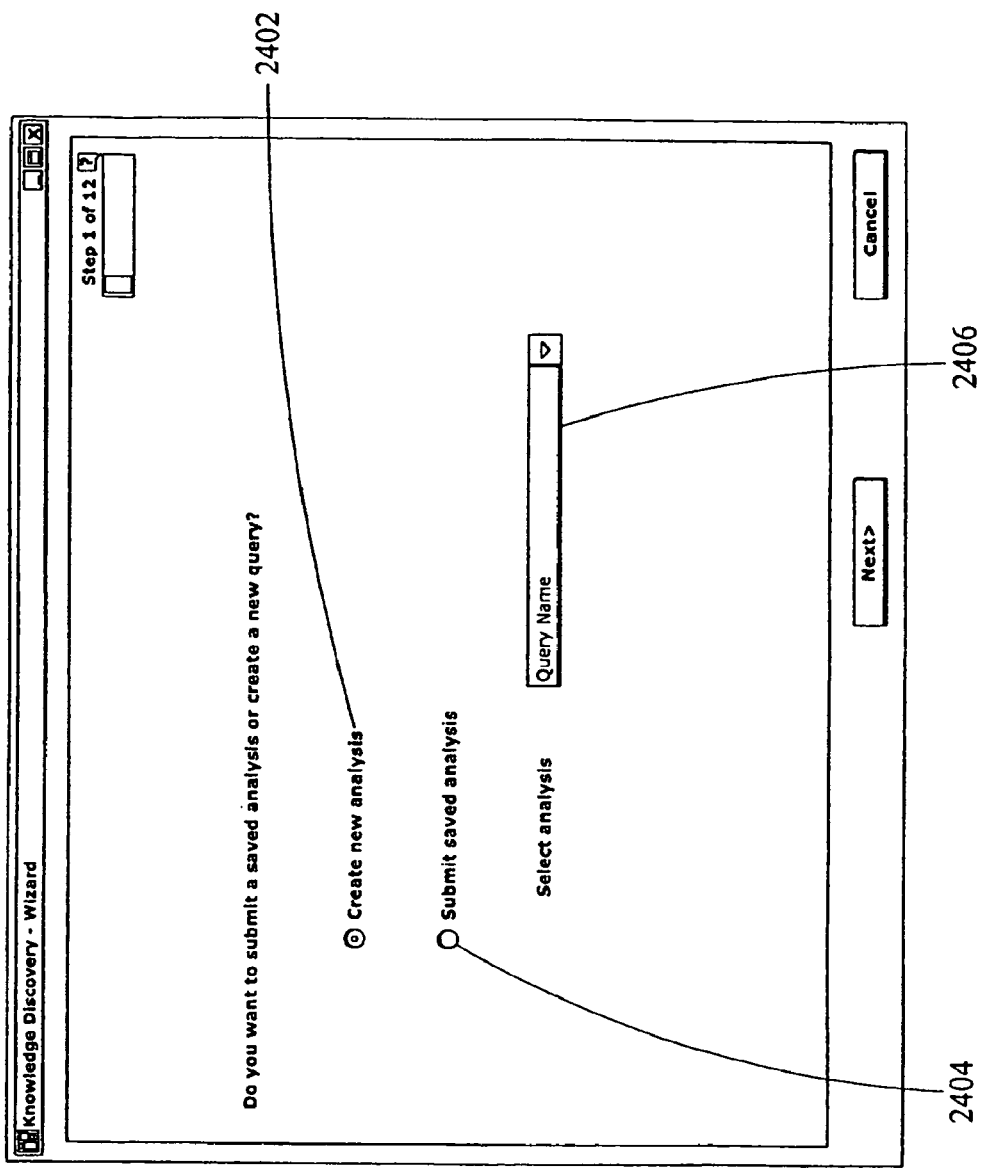
Figure 24B:
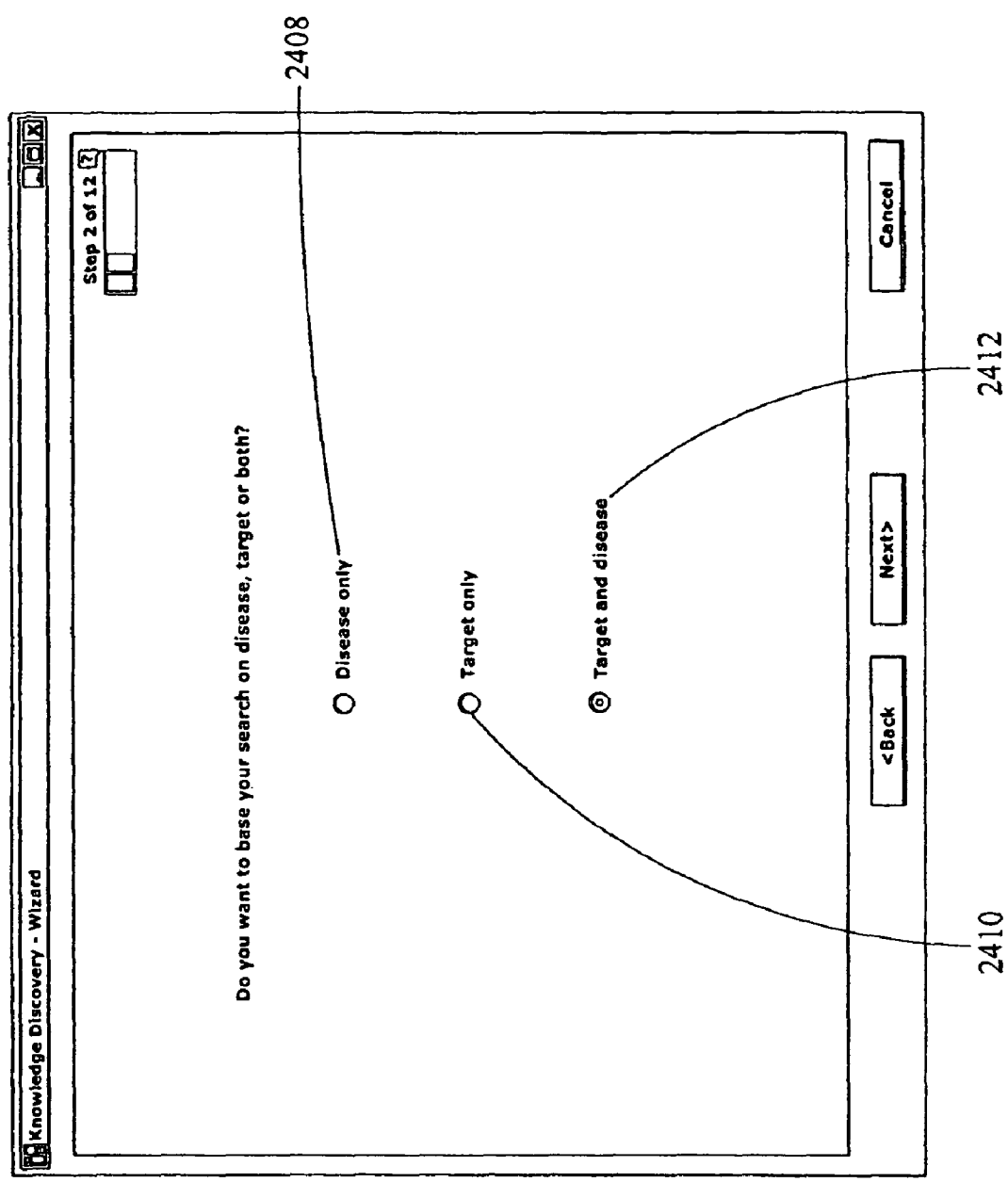

Exemplary screen shots of a wizard service are shown in FIGS. 24A-L. In one embodiment, there are three stages to the workflow of the wizard service. As shown in FIG. 24A, the user may initially choose to create a new search 2402 or load a previously saved search 2404. Saved searches may be retrieved via a drop-down list 2406. Next, the user may define the scope of the analysis. For example, diseases experts and target class representatives identify their initial area of interest such as a disease 2408 or a target 2410, or both 2412, through the use of the wizard, as shown in FIG. 24B. Depending on their selection, the wizard service will guide the user through a series of screens to further define the scope of the search.

Figure 24D:
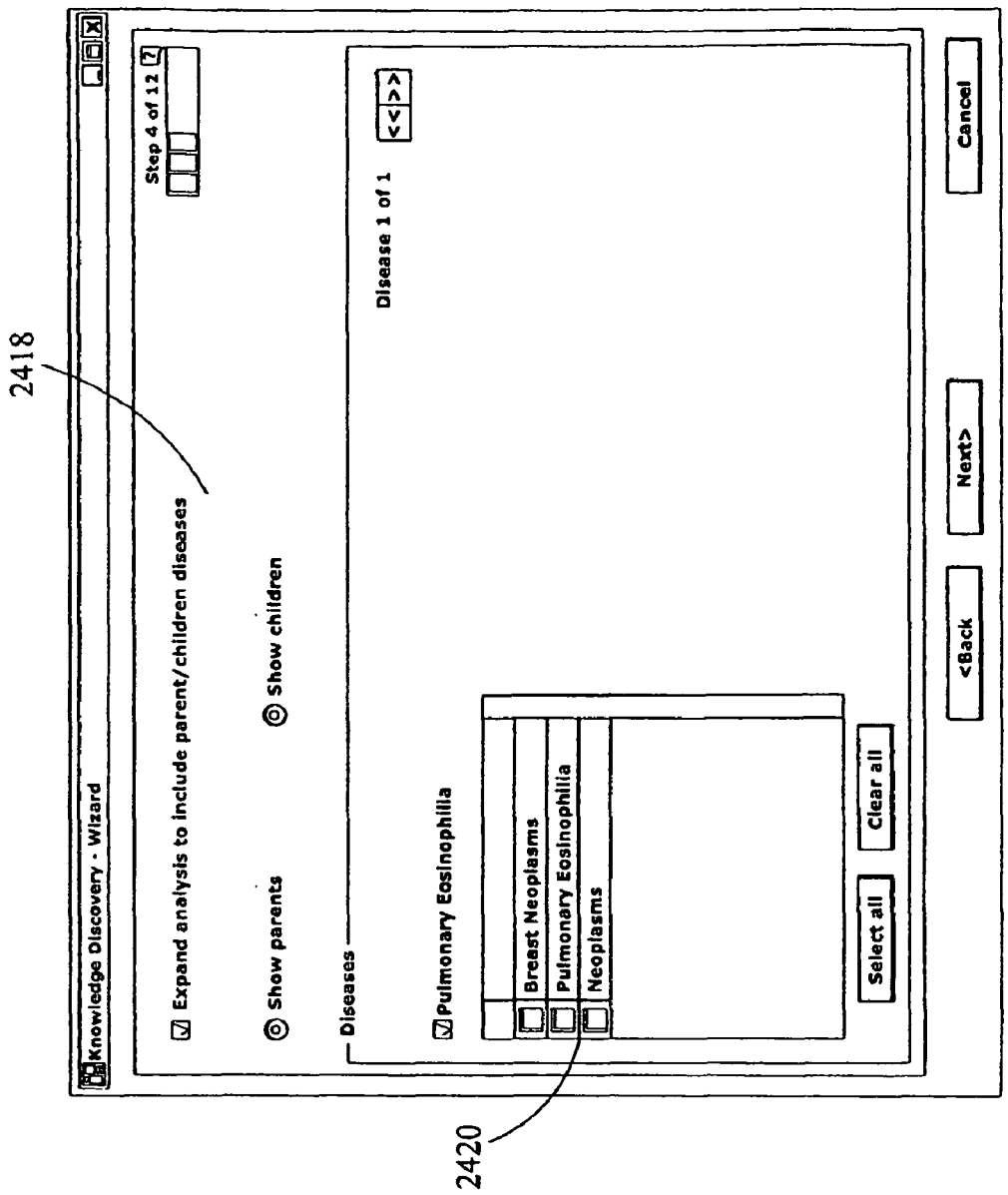
Figure 24E:
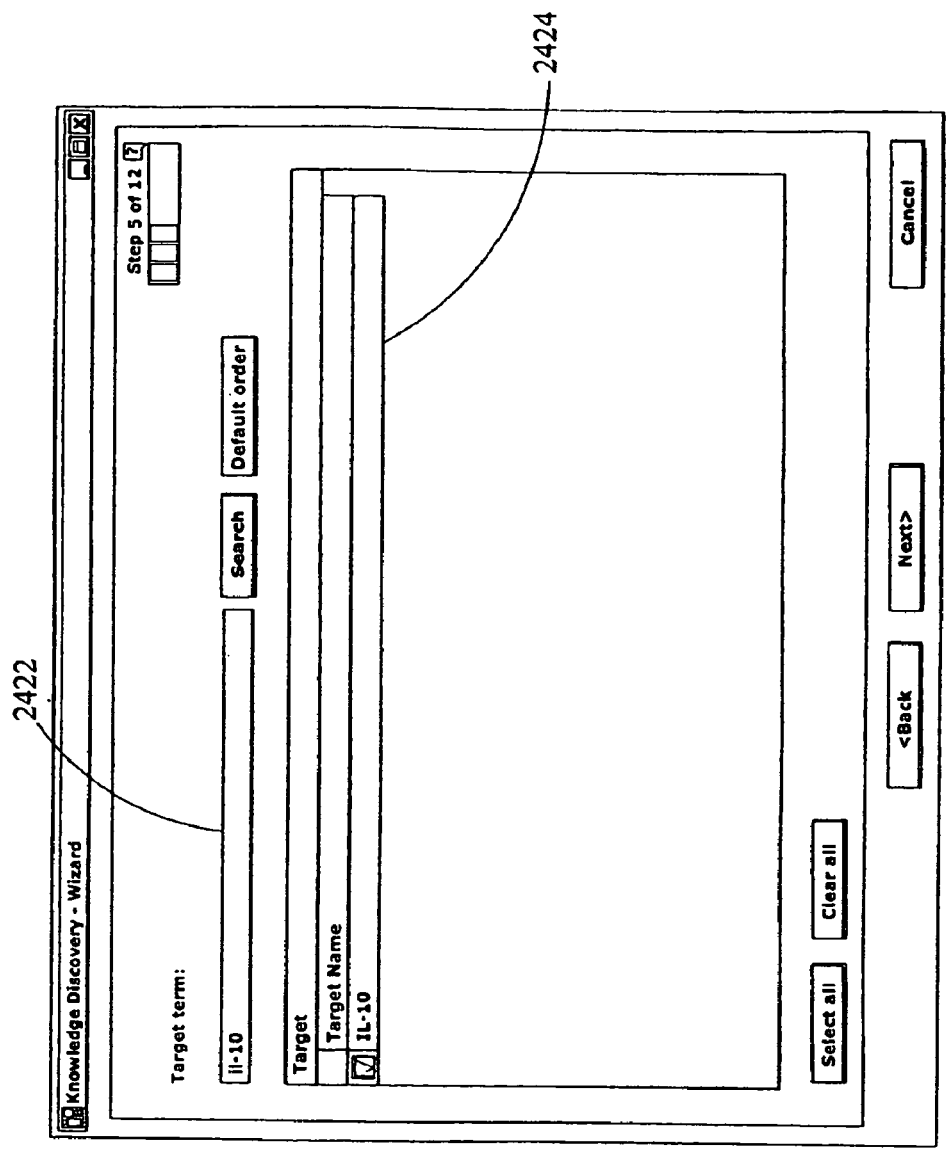
Figure 24F:
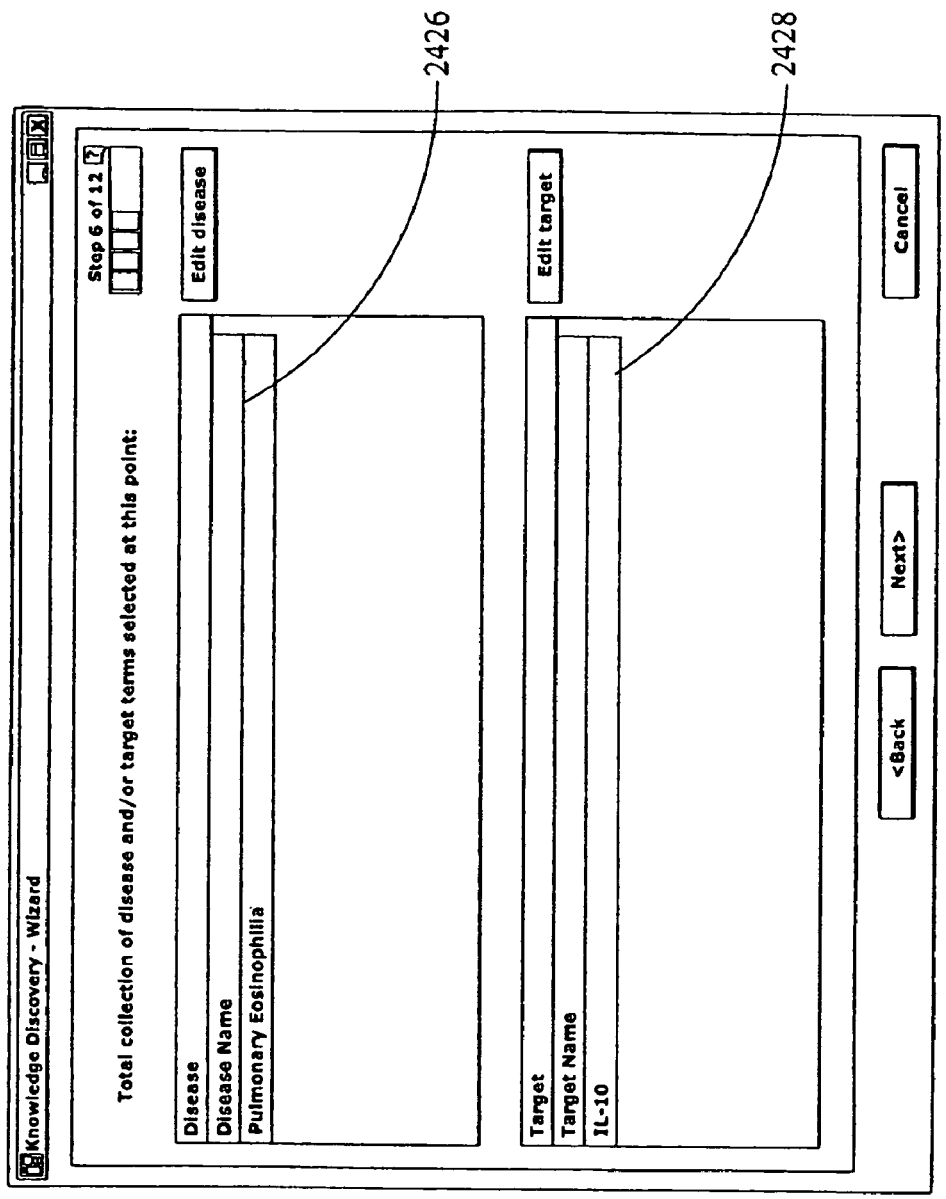

Next, matching terms are searched and allow user to select one or more matching terms to augment or refine search parameters. An exemplary process for determining additional keywords for diseases is shown in FIGS. 24C-D. Based on the input keyword 2414, the wizard service may assist the user to enhance the list of terms 2416 by providing them with a list of diseases including the keyword 2414, as shown in FIG. 24C. Additionally, the user may choose 2418 to include known related diseases, such as parent and/or child diseases, as shown in FIG. 24D. If the user so chooses 2418, a list of known related diseases 2420 may be displayed. The may choose to include any or all of the related diseases in the search. Similarly, the user may select targets by entering a target keyword 2422 and selecting targets that include the keyword 2424, as shown in FIG. 24E. Once the user has defined the diseases and/or targets to include in the search, the user may be be provided with a list of current diseases 2426 and/or targets 2428 and prompted to validate the selections, as shown in FIG. 24F. At this point, the user may edit the search parameters associated with each of the diseases 2426 and/or targets 2428.

Figure 24G:
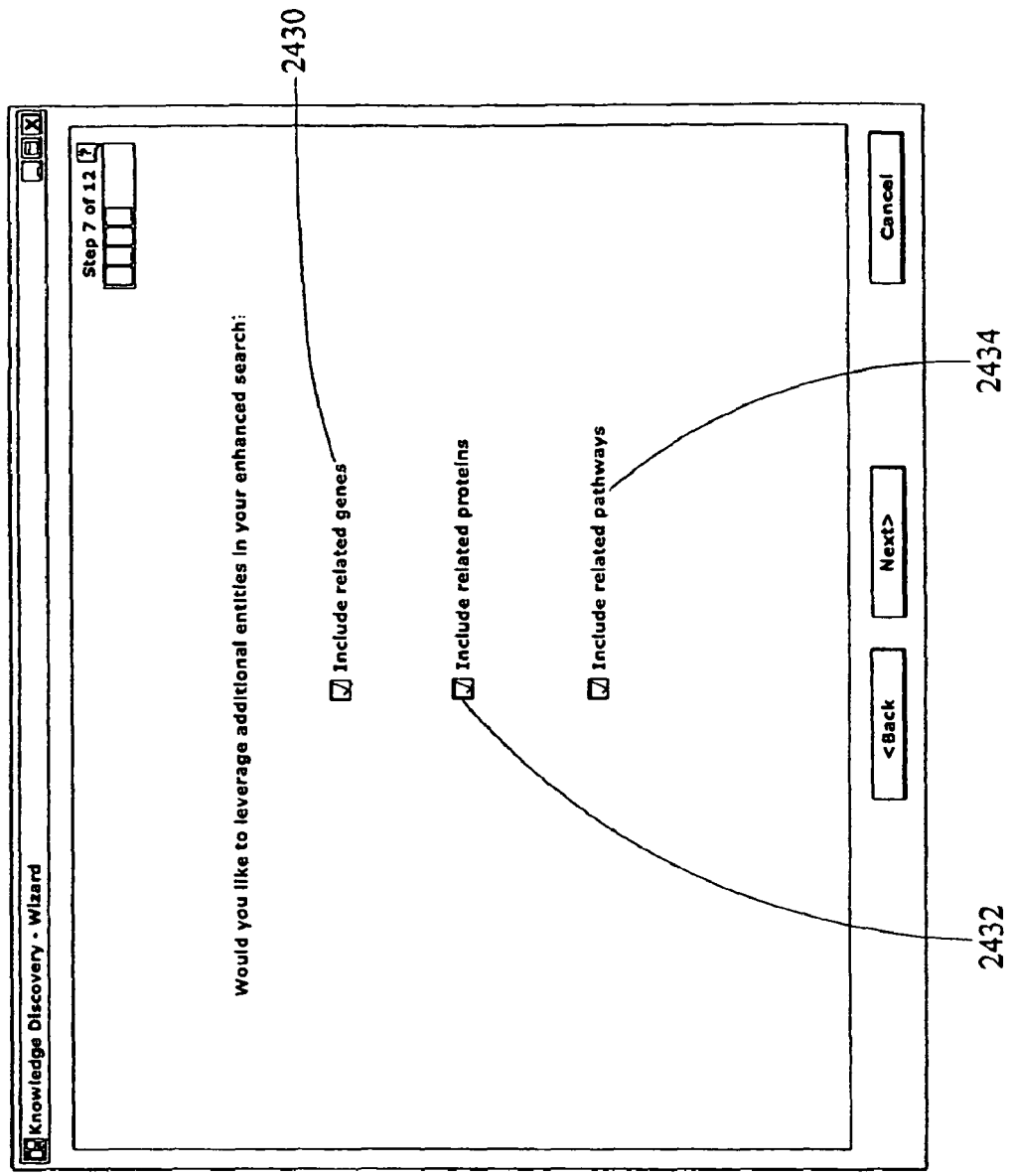
Figure 24H:
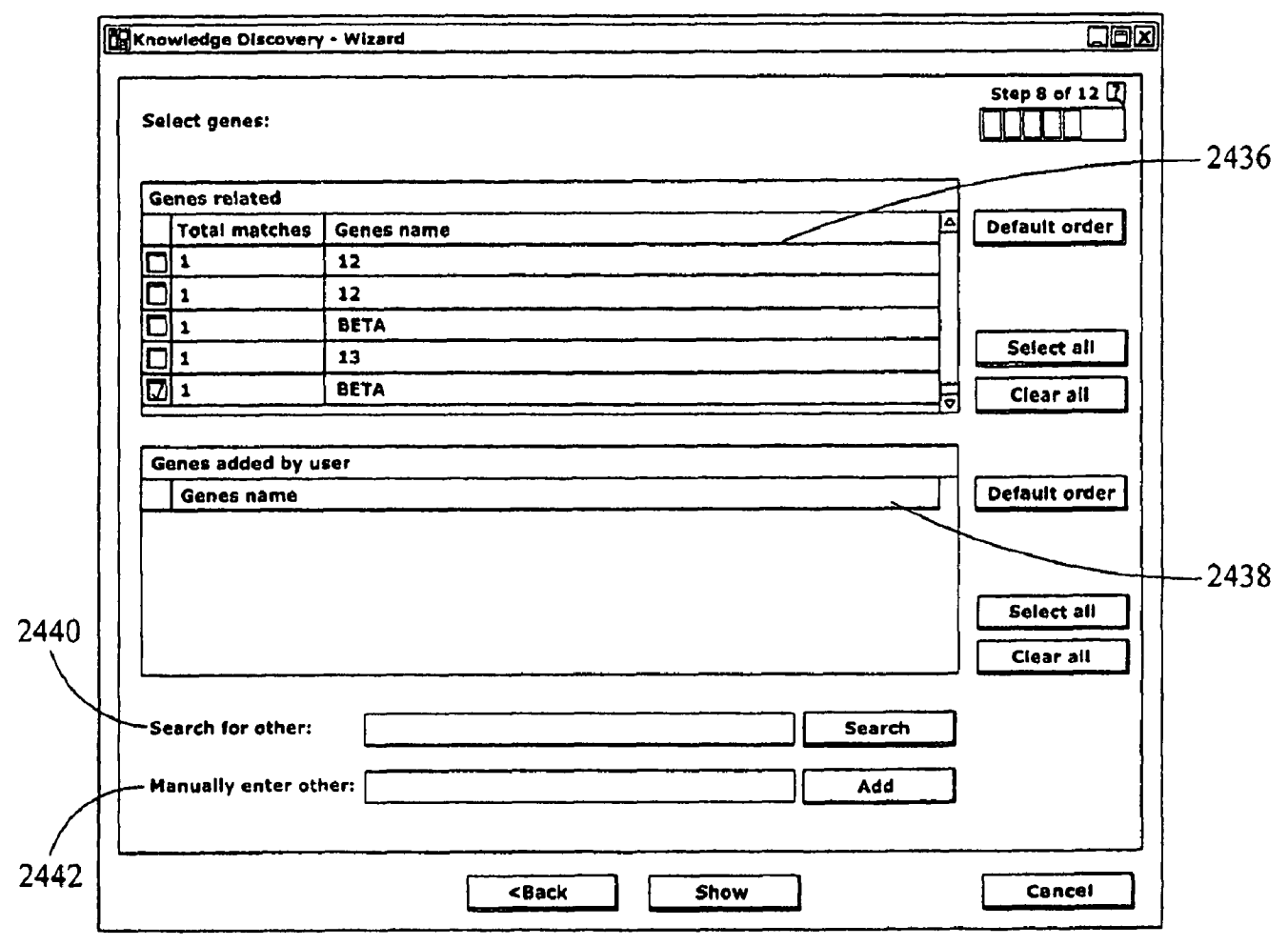
Figure 24I:
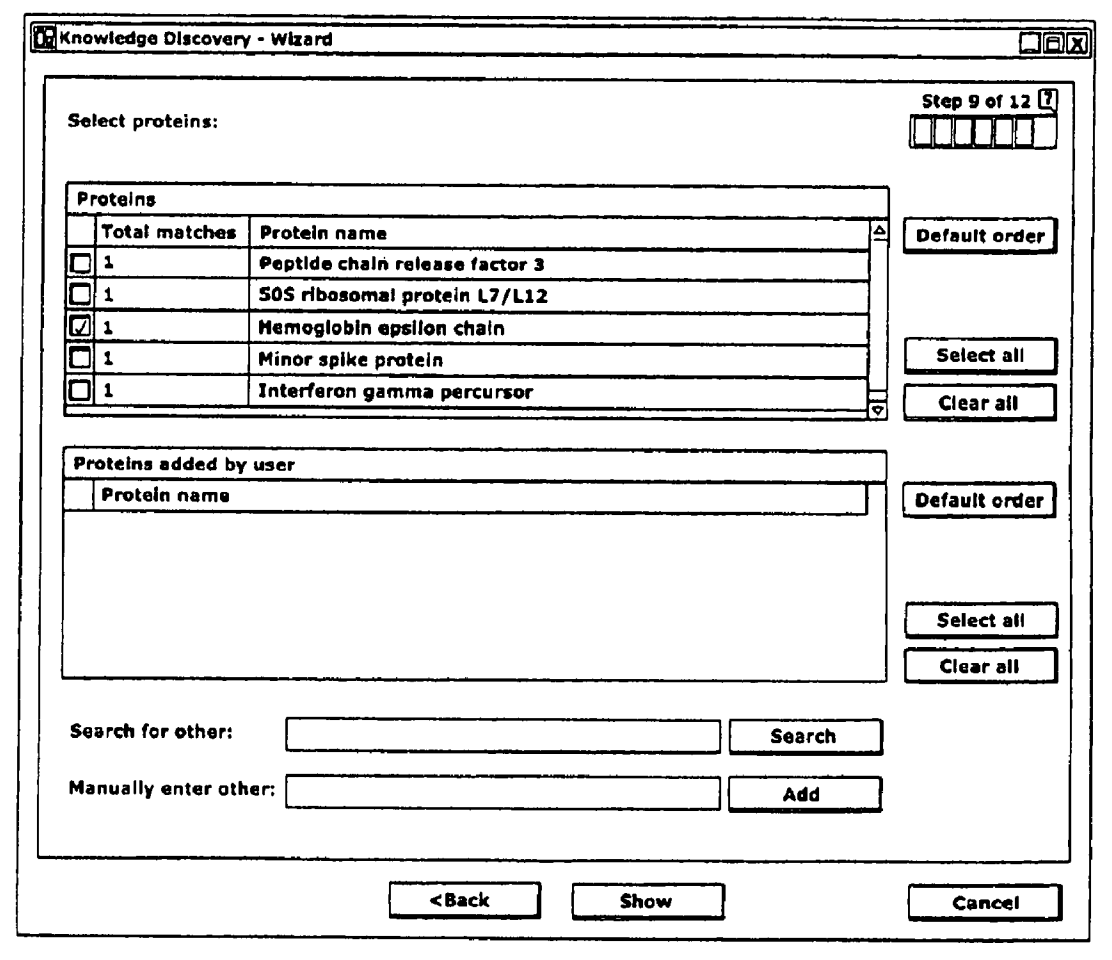
Figure 24J:
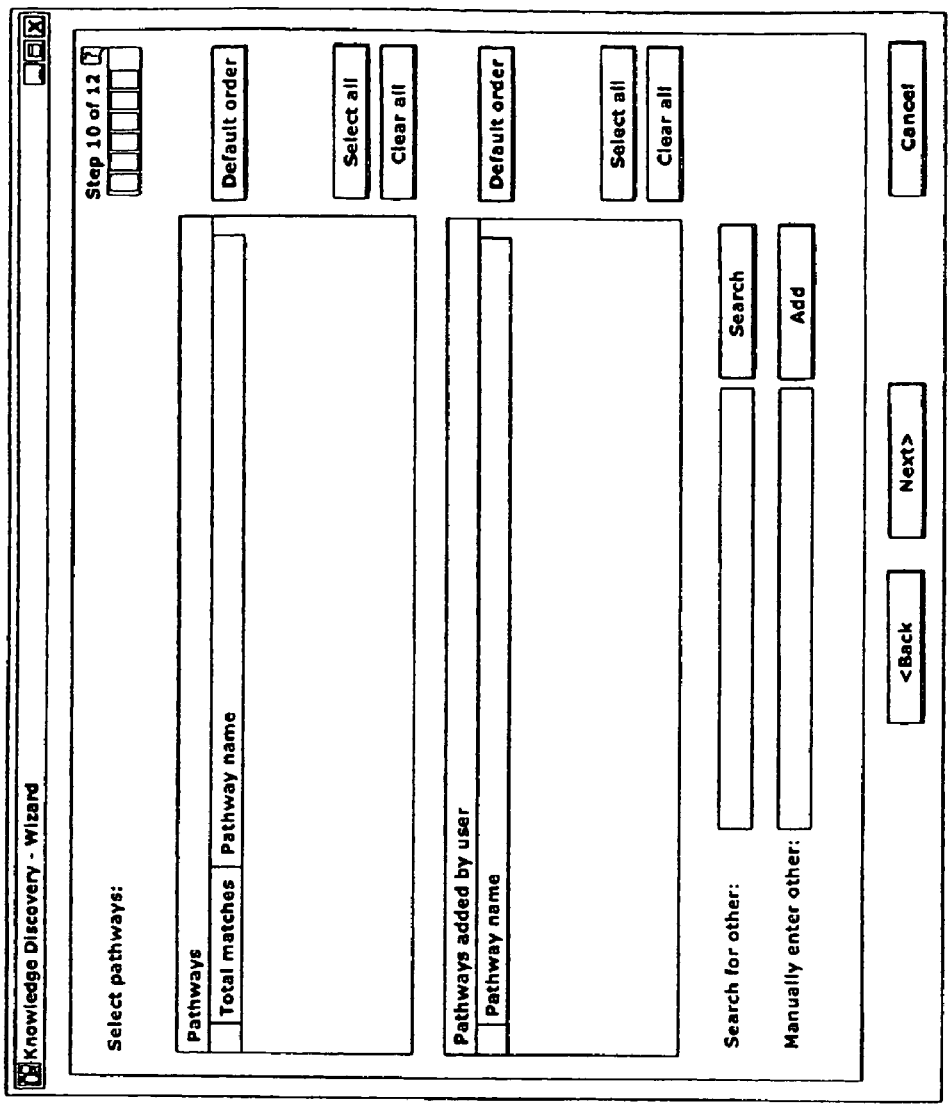

Next, the user may choose to augment the search to include additional keywords from topics such as genes 2430, proteins 2432, and pathways 2434, as shown in FIG. 24G. In each case, the user may be presented with a list of additional keywords and have the ability to select any keywords from the list to include them in the search. As shown in FIG. 24H, the user may be presented with a list 2436 of genes related to the selected diseases and/or targets. The user may then select any of the genes to add them in the search. Optionally, the user may also provide keywords 2440 to search for additional genes including the keyword 2440. Genes including the keyword 2440 may be displayed in the corresponding field 2438, and the user may select any gene from the list to include it in the search. Additionally, or alternatively, the user may also be able to directly add a known gene to the scope of a search by manually entering the gene into the appropriate field 2442. Similar processes may be included for adding protein and pathway related keywords to the search, as shown in FIGS. 24I and 24J.

Figure 24K:
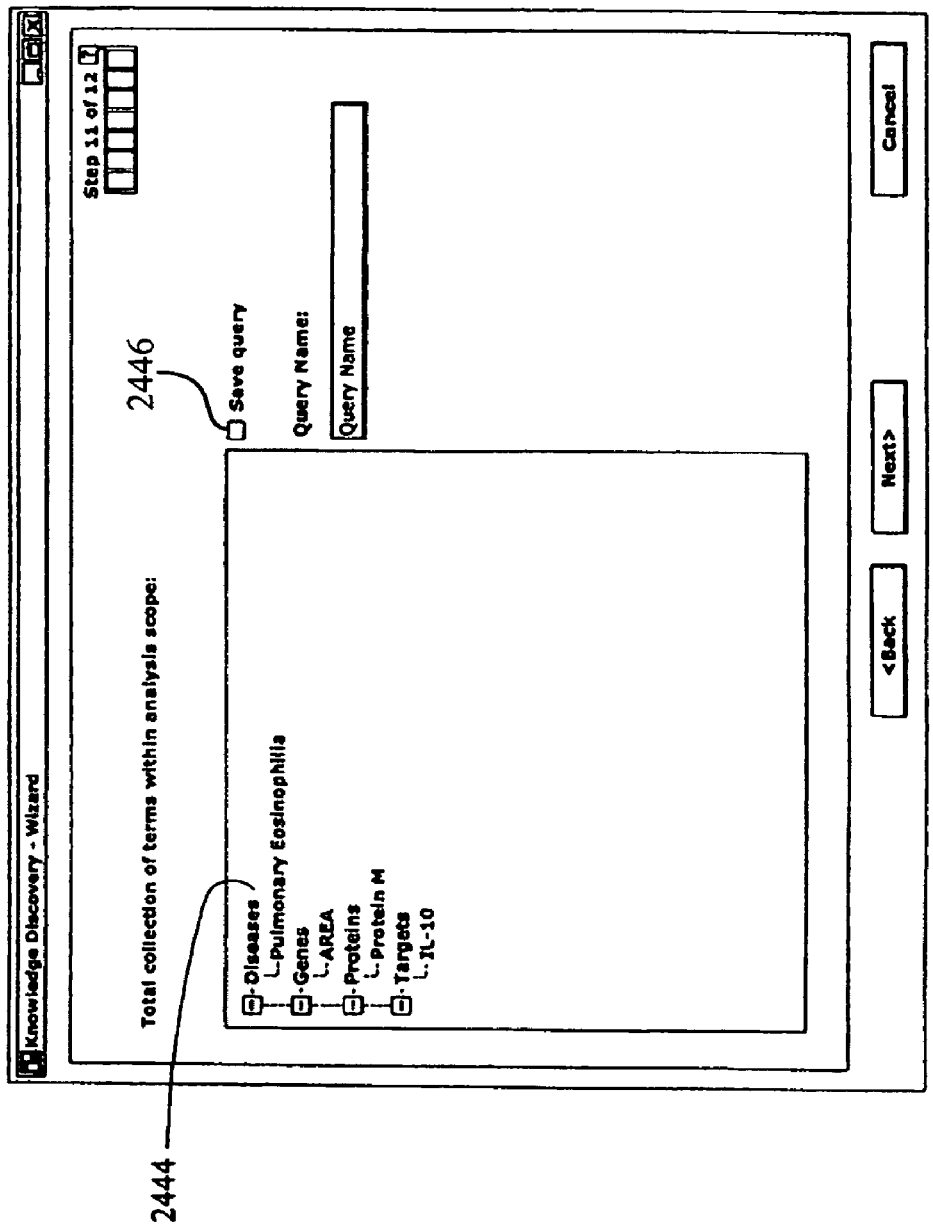

The result of this first stage is a collection of keywords that are related by the knowledge model 140. At this point, the user may be prompted to validate the scope of the search, as shown in FIG. 24K. A list of all keywords 2444 may be displayed. In one embodiment, the user may then choose to go back to any of the previous steps and further refine the scope of the search. The user also have the option to save 2446 the query at this point. In one embodiment, the user may save the query by entering a query name.

Once all the terms have been finalized, the wizard submits the query and collates the results. In one embodiment, these keywords may be searched against project and literature databases, for example, by submitting search strings to the database search indices to find, for example, projects and literature that match the list of relevant terms. The wizard service may return a set of projects/literature that match the set of query terms. Preferably, the query terms may be ranked and organized by the number of relevant search terms that were found in each search result. Thus, a results list of pointers to projects, and literature that mention the keyword combinations within the analysis scope may be created.

Finally, the user reviews the results identified to review potentially applicable projects and literature and compounds, as shown in FIG. 24L. In one embodiment, selecting an item on the results lists 2448 and 2450 causes that item to become the active node 1838. When an item of the results list is selected, that item takes centrals focus in navigator tool 170, allowing the user to rapidly build an understanding of the item selected and to explore the knowledge model 140 around the project/asset to add context and explore related literature and topics.

Figure 25:
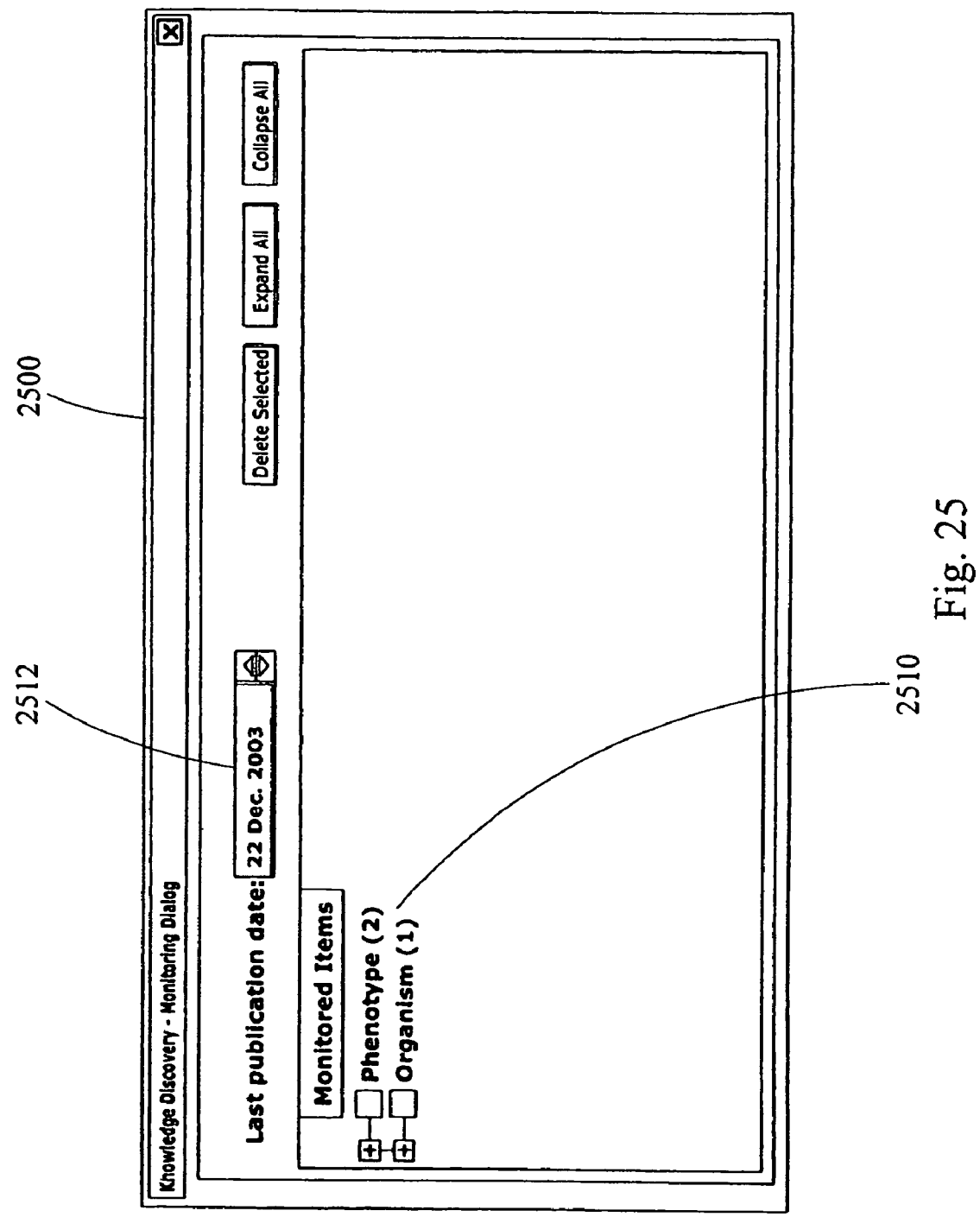
FIG. 25 is an exemplary screen shot of a monitored items dialog in accordance with an embodiment of the present invention.

Referring again to FIG. 19, a monitored items button 1934 may be provided to launch a monitored items dialog that allows the user to select to be notified when new relationships or literature are discovered for a particular item. An exemplary monitored items dialog 2500 is shown in FIG. 25. The monitored items dialog 2500 includes a last publication date 2510 which represents the most recent date on which new information was integrated into the knowledge model 140. The dialog also includes a list 2512 of all monitored items that have changed since the items associated monitoring date and the last publication date 2510.

Referring again to FIG. 19, a filters button 1936 may be provided to launch a filters dialog that allow the user to establish filter settings that filter the related items 1940 being displayed in an entity component 1932. In general, filters are a mechanism for focusing the results displayed in the navigator tool 170. Preferably, the filters are implemented as client-side applications. It should be apparent to one of ordinary skill in the art that the number of filters available for an entity component may vary based on the data stored in the associated knowledge model 140 table. Preferably, several types of filters are accessible directly from the Navigator panels. The entity component 1832 should display a filter icon 1844 if one or more filters exist for that pane. Clicking on the filter icon may also launch the filters dialog.

An exemplary filters dialog 2600 is shown in FIGS. 26A-E. The filters dialog 2600 may include several tabbed filter options pages in which the user may specify various filtering options, such as general filter options, entity filtering options, journal filtering options, publication filtering options, and the like. In one embodiment, general filtering options include filter persistence 2602 and internal/external filtering 2604. If the user selects persistent filtering 2602, the navigator tool 170 will filter the results of each navigation event. Otherwise, the navigator tool will only filter the current navigation event. Toggling the internal/external filtering option 2604 allows the user to limit results to data source that are internal or external to their enterprise.

FIG. 26B shows an exemplary screen shot of a entity filter options page. Entity filtering allows the user to specify parameters to filter the display to show only those related items 1840 that relate to specific entities. Exemplary entity filter entities for a pharmaceutical research navigation tool include organisms and phenotypes. In one embodiment, the user may specify a list of phenotypes 2610 and/or organisms 2612 to display. The user may edit the list of displayable organisms by selecting the edit list button 2614, which may launch a dialog 2620 as shown in FIG. 26C. The user may then view a list of available organisms 2622 by entering a keyword or selecting the appropriate first letter of the organism name from the alpha-bar 2626. The user may then select organisms to add or remove from the list of displayable organisms 2628. A similar dialog may be used to edit the phenotype list.

Figure 26A:
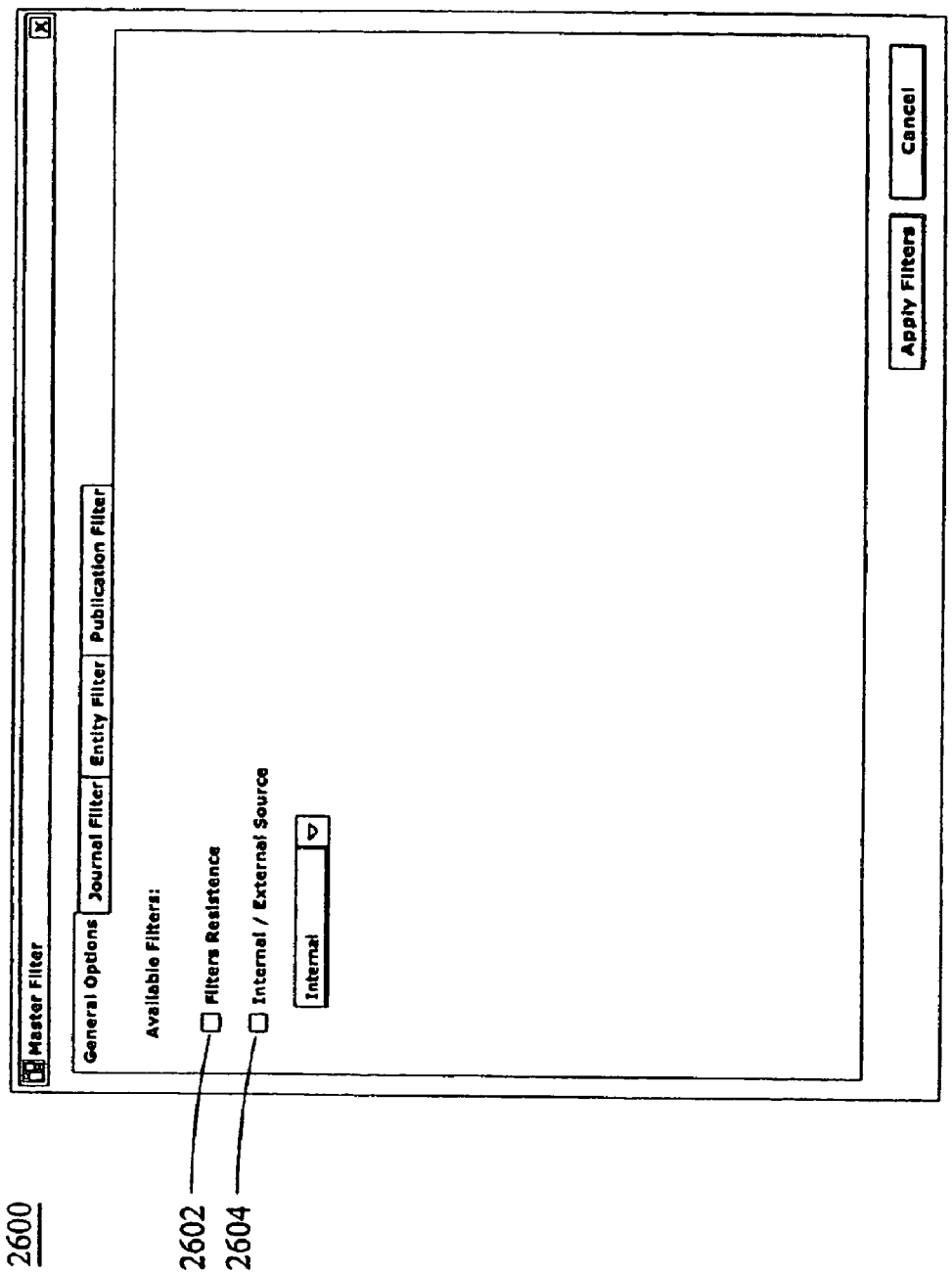
Figure 26C:
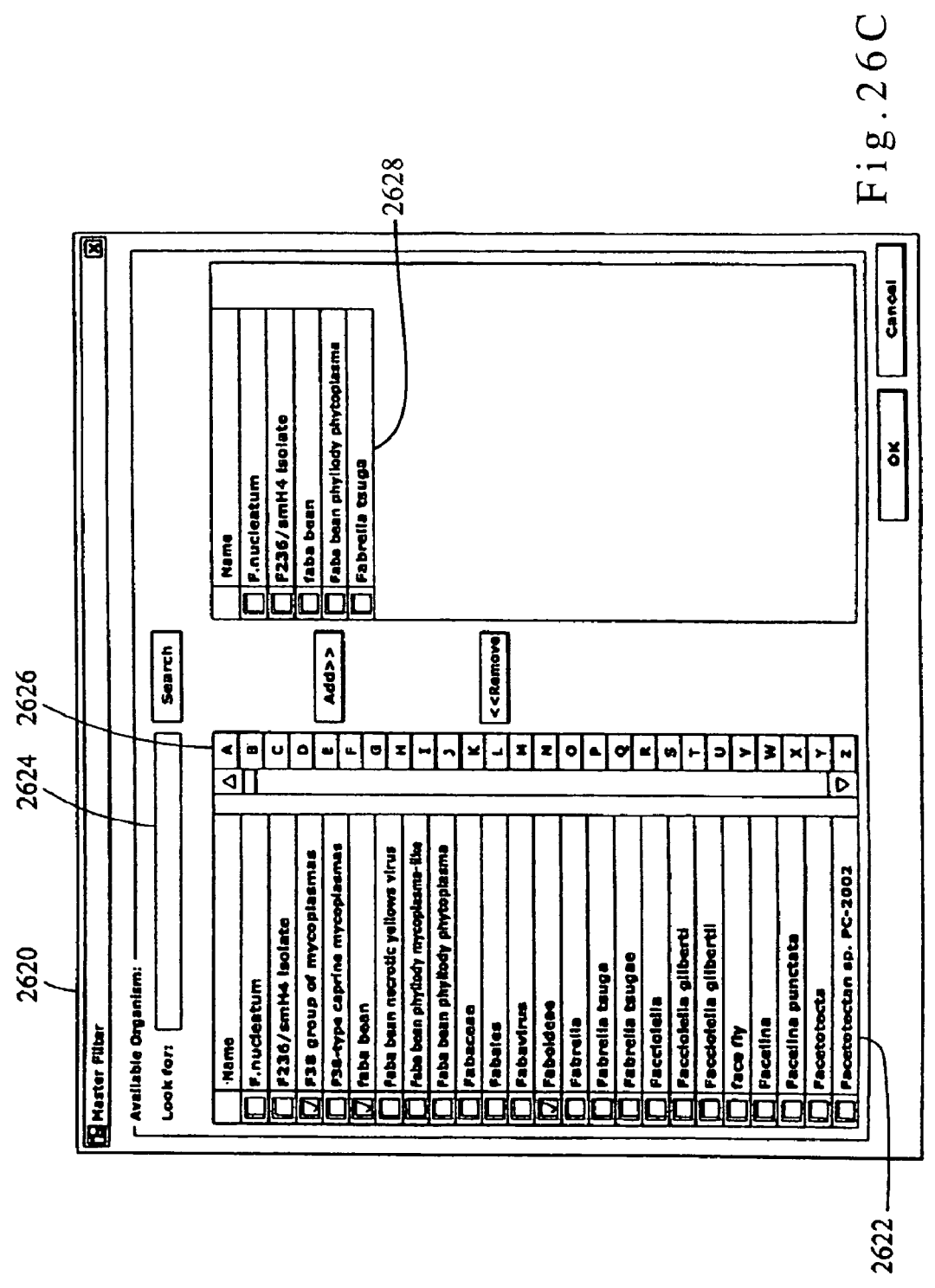
Figure 26D:
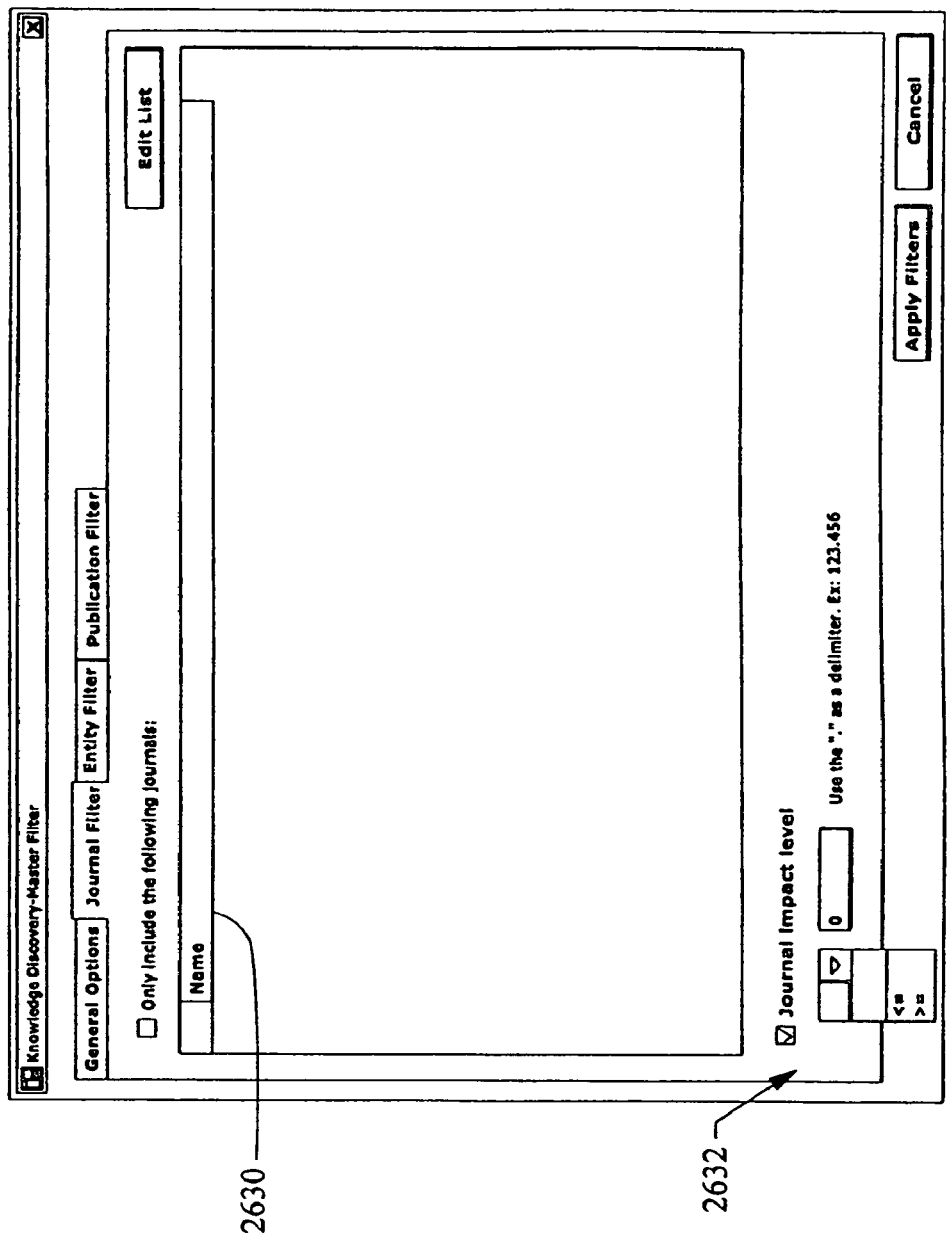
Figure 26E:
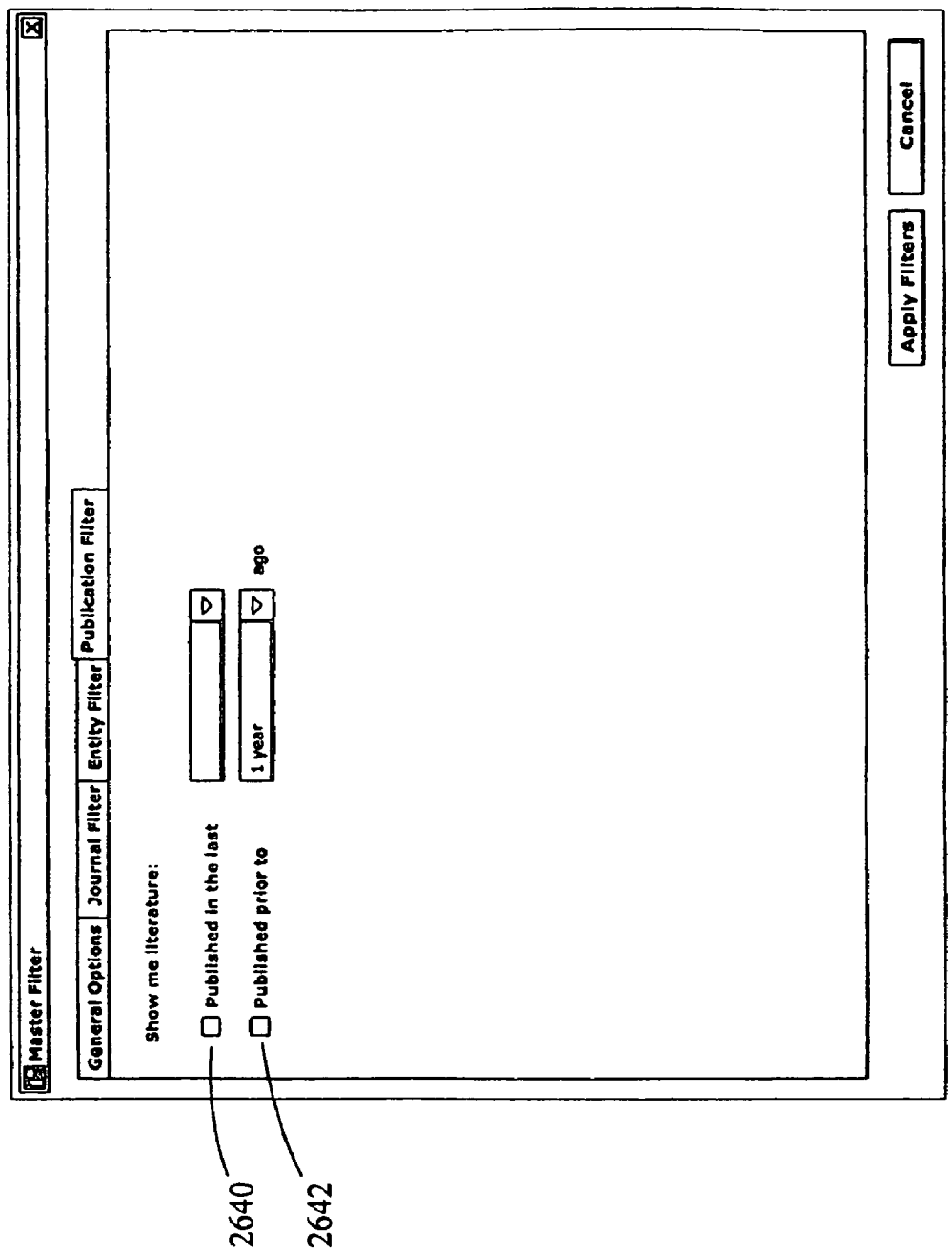

The user may also be able to filter displayed literature items to those items found in particular journals. An exemplary screen shot of a journal filter options page is shown in FIG. 26D. The user may specify a list of displayable journals 2630 in a similar manner to the organism and phenotype lists described above. Additionally, the user may specify a threshold journal impact level via the corresponding controls 2632. In one embodiment, the journal impact level corresponds to an ISI journal impact ranking. Finally, the user may also be able to filter items based on their publication date, as shown in FIG. 26E. In one embodiment, the user may limit the results to items published within a set amount of time 2640, or to those items published before a certain date 2642.

Referring again to FIG. 19, an internal/external filter button 1938 may be provided to allow the user to select related items 1940 based on the source from which they were obtained, as describe above. A confidence box 1940 may also be provided to allow the user to filter the items 1940 displayed in all entity components 1930 based on confidence values. These filters are referred to as confidence filters. In one embodiment, the confidence box 1940 is implemented a button associated with each confidence value may be provided to allow the user to display/hide links of the corresponding confidence value. Alternatively, the confidence button 1940 may be implemented as a list of confidence values wherein the navigator tool only displays those items 1940 meeting the selected threshold confidence value. In yet another embodiment, the confidence button 1940 may be implemented as a text box that establishes a threshold confidence value and only those related items 1940 meeting the threshold value may be displayed. The threshold confidence value may be indicative of the relationship type, as described above. For example, a threshold value of one may correspond to a direct relationship.

A context drop down list 1942 may be included to provide the user with a list of previously saved, or system provided, stored sets of context. A context represents a set of navigator tool settings. In one embodiment, a context includes filter settings, confidence filter settings, and panel layouts. Alternatively, or in addition to, the context drop down list 1942 may also provide access to personal and group default preferences sets associated with login information. Upon selection of a context set, the navigator tool 170 will update the current display to reflect the newly selected context. Alternate context sets containing various sets of information should be readily apparent to one of ordinary skill in the art. For example, master context information may also be stored in a context set. The context drop down list 1942 may display a list of stored preference sets by name. In one embodiment, a user may save a new context by selecting a "save new" option from the context drop-down list 1942.

It is therefore intended that the foregoing detailed description be regarded as illustrative rather than limiting, and that it be understood that it is the following claims, including all equivalents, that are intended to define the spirit and scope of this invention.

The invention claimed is:
1. A computer system comprising:
 a processor; and memory coupled to the processor and having stored therein instructions that, if executed by the computer system, cause the computer system to perform operations comprising:
 providing, in a database, a plurality of entity table types relevant to a domain type, wherein each entity table type includes a respective entity table name field and at least one respective data item field;

populating the respective entity table name fields and the respective data item fields by automatically:

extracting a plurality of data items from a plurality of data sources;

determining respective confidence values for the extracted data items based on a plurality of pre-determined confidence values, wherein the pre-determined confidence values, wherein a respective predetermined confidence value is provided for each respective entity table name and each respective data item according to which data source of the plurality of data sources provided the respective entity table name and the respective data item; and integrating the extracted data items into respective entity table name fields and data item fields based on the respective confidence values for the extracted data items;

determining relationship types between at least some data items of the plurality of data items that are integrated into a plurality of tables in the database, wherein the relationship types are based on respective data sources from which the data items have been extracted, the relationship types including at least two of the following: a first relationship type, a second relationship type, a third relationship type, and a fourth relationship type, wherein:

the first relationship type is between first and second data items extracted from a first structured data source, the second relationship type is between data items extracted from different structured data sources, wherein the second relationship type is based on a plurality of respective first relationship types, the third relationship type is between a data item extracted from a second structured data source, and an entity table including, as entity table data items, attributes about a first unstructured data source, and wherein the data item extracted from the second structured data source is mentioned in the first unstructured data source, and the fourth relationship type is between two data items that:

have been integrated from different structured data sources, and are both mentioned in a second unstructured data source; and storing the relationship types in a computer system memory.

2. The computer system of claim 1 wherein the operations further comprise:

updating the database if a previously integrated data item has been modified in a data source;

determining whether a previously integrated data item has been modified by automatically:

determining a first data item value for the previously integrated data item;

determining a second data item value based on the data item in the data source; and comparing the first data item value to the second data item value, wherein the first and second data item values are respective hash values based on, respectively, the previously integrated data item and the data item in the data source.

3. The computer system of claim 1 wherein the operations further comprise automatically establishing a field-to-field link in the database, wherein the field-to-field link is selected from the group consisting of: a field-to-filed link between two respective data items if both respective data items were integrated from a single structured data source; a field-to-field link between a first entity table name field and a second entity table name field if both the first and second entity table name fields were integrated with data items from a single structured data source; and a field-to-field link between a first entity table name field of a first entity table and a data item field of a second entity table if both the first entity table name field and the data item field of the second entity table were integrated with data items from a single structured data source.

4. The computer system of claim 1 wherein the operations further comprise establishing a transitive link within the database, wherein the transitive link is selected from the group consisting of: a one-hop transitive link between a first integrated data item and a second integrated data item if the first integrated data item and a third integrated data item were both integrated from a first structured data source, and the second integrated data item and the third integrated data item were both integrated from a second structured data source; and a multi-hop transitive link between a first integrated data item and a second integrated data item based on a plurality of data items integrated from a plurality of structured data sources.

5. The computer system of claim 1 wherein the operations further comprise:

establishing in the database an entity table that contains attributes about an unstructured data source, including a title of the unstructured data source, wherein the unstructured data source is one of: an article, a document, a web page, an HTML file, and a spreadsheet; and establishing in the database a field-to-text link between an integrated data item from a structured data source and the entity table if the integrated data item is mentioned in the unstructured data source.

6. The computer system of claim 1 wherein the operations further comprise:

establishing an entity table that contains attributes about an unstructured data source, including a title of the unstructured data source; and establishing a proximity link between two data items integrated from respective structured data sources if the two data items are both mentioned in the unstructured data source, wherein the proximity link is further based upon a proximity definition selected from the group consisting of: proximity within a paragraph, proximity within a sentence, proximity within a predetermined number of words, and proximity within a spreadsheet.

7. The computer system of claim 1 wherein the operations further comprise assigning confidence levels between links in the database, wherein a first confidence level is assigned to each field-to-field link within the database, a second confidence level is assigned to each field-to-text link within the database, a third confidence level is assigned to each transitive link in the database, and a fourth confidence level is assigned to each proximity link in the database.

8. The computer system of claim 1 wherein the operations further comprise:

determining a synonym for a first extracted data item; and integrating the first extracted data item into the database based on the synonym, wherein the synonym is integrated into the database.

9. The computer system of claim 1 wherein the operations further comprise:

displaying an active panel data item in an active panel of a multiple panel user display;

displaying in other panels of the multiple panel user display, simultaneously with the display of the active panel data item, entity tables having data items that have a relationship to the active panel data item, wherein respective relationships between the active panel data item and respective data items displayed in the other panels are each one of: a field-to-field link, a field-to-text link, a transitive link, and a proximity link; and displaying, on a user interface, relationship type indicia to indicate relationship types between displayed data items.

10. The computer system of claim 1, wherein the pre-determined confidence values indicate reliability of each of the data sources based on at least one of an internal review of the data sources and an external review of the data sources, wherein the internal review is performed by reviewers selected from the group consisting of: reviewers comprising users of a system implementing the operations, and reviewers comprising developers of a system implementing the operations; wherein the external review is performed using a third party reliability standard; and wherein the operations further comprise:

comparing a first confidence value indicating reliability of a third data item stored in a data item field to a second confidence value indicating reliability of a data source having a fourth data item for the data item field;

updating the database by integrating the fourth data item into the data item field if the second confidence value is greater than the first confidence value;

associating time stamps with the extracted data items; and using the time stamps for the third and fourth data items to determine which of the third and fourth items is more recent if the first and second confidence values are the same, wherein the more recent of the third and fourth data items is integrated into the data item field in the database if the first and second confidence values are the same.

11. A computer system comprising:

a processor; and memory coupled to the processor and having stored therein instructions that, if executed by the computer system, cause the computer system to perform operations comprising:

providing, in a database, a plurality of entity table types relevant to a domain type, wherein each entity table type includes a respective entity table name field and at least one respective data item field;

populating the respective entity table name fields and the respective data item fields by automatically:

extracting a plurality of data items from a plurality of data sources;

determining respective confidence values for the extracted data items based on a plurality of pre-determined confidence values, wherein a respective predetermined confidence value is provided for each respective entity table name and each respective data item according to which data source of the plurality of data sources provided the respective entity table name and the respective data item;

integrating the extracted data items into respective entity table name fields and data item fields based on the respective confidence values for the extracted data items;

storing a first data item extracted from a first data source in a first data item field and storing a second data item extracted from the first data source in a second data item field;

populating a first row of a direct relationship table having a plurality of rows with a first direct relationship definition indicating that the first data item field and the second data item field store respective data items that have been extracted from the first data source;

searching the direct relationship table for a second row having a second direct relationship definition indicating that a third data item field stores a third data item that has been extracted from a second data source from which the first data item has also been extracted, wherein the second data source is different than the first data source;

determining a transitive relationship definition, based on the first direct and second direct relationship definitions from the direct relationship table, indicating that the second data item field is related to the third data item field, wherein the transitive relationship definition is based on at least two separate relationships between data item fields; and storing the third relationship definition in a transitive relationship table.

12. The computer system of claim 11 wherein the operations further comprise:

updating the database if a previously integrated data item has been modified in a data source;

determining whether a previously integrated data item has been modified by automatically:

determining a first data item value for the previously integrated data item;

determining a second data item value based on the data item in the data source; and comparing the first data item value to the second data item value, wherein the first and second data item values are respective hash values based on, respectively, the previously integrated data item and the data item in the data source.

13. The computer system of claim 11 wherein the operations further comprise automatically establishing a field-to-field link in the database, wherein the field-to-field link is selected from the group consisting of: a field-to-filed link between two respective data items if both respective data items were integrated from a single structured data source; a field-to-field link between a first entity table name field and a second entity table name field if both the first and second entity table name fields were integrated with data items from a single structured data source; and a field-to-field link between a first entity table name field of a first entity table and a data item field of a second entity table if both the first entity table name field and the data item field of the second entity table were integrated with data items from a single structured data source.

14. The computer system of claim 11 wherein the operations further comprise establishing a transitive link within the database, wherein the transitive link is selected from the group consisting of: a one-hop transitive link between a first integrated data item and a second integrated data item if the first integrated data item and a third integrated data item were both integrated from a first structured data source, and the second integrated data item and the third integrated data item were both integrated from a second structured data source; and a multi-hop transitive link between a first integrated data item and a second integrated data item based on a plurality of data items integrated from a plurality of structured data sources.

15. The computer system of claim 11 wherein the operations further comprise:

establishing in the database an entity table that contains attributes about an unstructured data source, including a title of the unstructured data source, wherein the unstructured data source is one of: an article, a document, a web page, an HTML file, and a spreadsheet; and establishing in the database a field-to-text link between an integrated data item from a structured data source and the entity table if the integrated data item is mentioned in the unstructured data source.

16. The computer system of claim 11 wherein the operations further comprise:

establishing an entity table that contains attributes about an unstructured data source, including a title of the unstructured data source; and establishing a proximity link between two data items integrated from respective structured data sources if the two data items are both mentioned in the unstructured data source, wherein the proximity link is further based upon a proximity definition selected from the group consisting of: proximity within a paragraph, proximity within a sentence, proximity within a predetermined number of words, and proximity within a spreadsheet.

17. The computer system of claim 11 wherein the operations further comprise assigning confidence levels between links in the database, wherein a first confidence level is assigned to each field-to-field link within the database, a second confidence level is assigned to each field-to-text link within the database, a third confidence level is assigned to each transitive link in the database, and a fourth confidence level is assigned to each proximity link in the database.

18. The computer system of claim 11 wherein the operations further comprise:

determining a synonym for a first extracted data item; and integrating the first extracted data item into the database based on the synonym, wherein the synonym is integrated into the database.

19. The computer system of claim 11 wherein the operations further comprise:

displaying an active panel data item in an active panel of a multiple panel user display;

displaying in other panels of the multiple panel user display, simultaneously with the display of the active panel data item, entity tables having data items that have a relationship to the active panel data item, wherein respective relationships between the active panel data item and respective data items displayed in the other panels are each one of: a field-to-field link, a field-to-text link, a transitive link, and a proximity link; and displaying, on a user interface, relationship type indicia to indicate relationship types between displayed data items.

20. The computer system of claim 11, wherein the predetermined confidence values indicate reliability of each of the data sources based on at least one of an internal review of the data sources and an external review of the data sources, wherein the internal review is performed by reviewers selected from the group consisting of: reviewers comprising users of a system implementing the operations, and reviewers comprising developers of a system implementing the operations; wherein the external review is performed using a third party reliability standard; and wherein the operations further comprise:

comparing a first confidence value indicating reliability of a third data item stored in a data item field to a second confidence value indicating reliability of a data source having a fourth data item for the data item field;

updating the database by integrating the fourth data item into the data item field if the second confidence value is greater than the first confidence value;

associating time stamps with the extracted data items; and using the time stamps for the third and fourth data items to determine which of the third and fourth items is more recent if the first and second confidence values are the same, wherein the more recent of the third and fourth data items is integrated into the data item field in the database if the first and second confidence values are the same.

* * * * *